US012310999B2

(12) United States Patent
Gansert et al.

(10) Patent No.: US 12,310,999 B2
(45) Date of Patent: May 27, 2025

(54) BIOMARKERS FOR CANCER THERAPEUTICS

(71) Applicants: MERCK SHARP & DOHME CORP., Rahway, NJ (US); AMGEN INC., Thousand Oaks, CA (US)

(72) Inventors: Jennifer Lorraine Gansert, Simi Valley, CA (US); Abraham Antonio Anderson, Sherman Oaks, CA (US); Kevin Gorski, Novato, CA (US)

(73) Assignees: MERCK SHARP & DOHME CORP., Rahway, NJ (US); AMGEN INC., Thousand Oaks, CA (US)

( * ) Notice: Subject to any disclaimer, the term of this patent is extended or adjusted under 35 U.S.C. 154(b) by 616 days.

(21) Appl. No.: 16/499,095

(22) PCT Filed: Apr. 27, 2018

(86) PCT No.: PCT/US2018/029915
§ 371 (c)(1),
(2) Date: Sep. 27, 2019

(87) PCT Pub. No.: WO2018/201028
PCT Pub. Date: Nov. 1, 2018

(65) Prior Publication Data
US 2021/0008135 A1    Jan. 14, 2021

Related U.S. Application Data

(60) Provisional application No. 62/491,746, filed on Apr. 28, 2017.

(51) Int. Cl.
| A61K 35/763 | (2015.01) |
| A61P 35/00 | (2006.01) |
| A61P 35/04 | (2006.01) |
| C07K 14/705 | (2006.01) |
| C07K 16/28 | (2006.01) |
| G01N 33/574 | (2006.01) |

(52) U.S. Cl.
CPC ............ *A61K 35/763* (2013.01); *A61P 35/00* (2018.01); *A61P 35/04* (2018.01); *C07K 14/70596* (2013.01); *C07K 16/2818* (2013.01); *G01N 33/5743* (2013.01)

(58) Field of Classification Search
CPC . A61P 35/04; A61K 35/763; C07K 14/70596; C07K 16/2818
See application file for complete search history.

(56) References Cited

U.S. PATENT DOCUMENTS

| 4,275,149 A | 6/1981 | Litman |
| 4,318,980 A | 3/1982 | Boguslaski |
| 4,522,811 A | 6/1985 | Eppstein |
| 4,737,456 A | 4/1988 | Weng |
| 4,816,567 A | 3/1989 | Cabilly |
| 5,143,854 A | 9/1992 | Pirrung |
| 5,242,974 A | 9/1993 | Holmes |
| 5,288,644 A | 2/1994 | Beavis |
| 5,324,633 A | 6/1994 | Fodor |
| 5,384,261 A | 1/1995 | Winkler |
| 5,405,783 A | 4/1995 | Pirrung |
| 5,412,087 A | 5/1995 | McGall |
| 5,424,186 A | 6/1995 | Fodor |
| 5,429,807 A | 7/1995 | Matson |
| 5,432,049 A | 7/1995 | Fischer |
| 5,436,327 A | 7/1995 | Southern |
| 5,445,934 A | 8/1995 | Fodor |
| 5,470,710 A | 11/1995 | Weiss |
| 5,472,672 A | 12/1995 | Brennan |
| 5,492,806 A | 2/1996 | Drmanac |
| 5,503,980 A | 4/1996 | Cantor |
| 5,510,270 A | 4/1996 | Fodor |
| 5,525,464 A | 6/1996 | Drmanac |
| 5,527,681 A | 6/1996 | Holmes |
| 5,529,756 A | 6/1996 | Brennan |
| 5,545,531 A | 8/1996 | Rava |
| 5,547,839 A | 8/1996 | Dower |
| 5,556,752 A | 9/1996 | Lockhart |

(Continued)

FOREIGN PATENT DOCUMENTS

| CN | 1425073 A | 6/2003 |
| EP | 2591796 A1 | 5/2013 |

(Continued)

OTHER PUBLICATIONS

ClinicalTrial.gov Archive, NCT02965716, History of Changes, first posted Apr. 23, 2017 (Year: 2017).*
Ott et al., Talimogene Laherparepvec for the Treatment of Advanced Melanoma, Clin Cancer Res; 22(13); 3127-3131, Publication Date:May 4, 2016 (Year: 2016).*
Long et al., Effi cacy analysis of Masterkey-265 phase 1b study of talimogenelaherparepvec (T-VEC) andpembrolizumab (pembro) forunresectable stage IIIB-IVmelanoma, Meeting Abstract, 2016 ASCO Annual Meeting I, Publication Date: May 20, 2016 (Year: 2016).*

(Continued)

*Primary Examiner* — Peter J Reddig
*Assistant Examiner* — Cheng Lu
(74) *Attorney, Agent, or Firm* — LATHROP GPM LLP; James H. Velema, Esq.; Judith L. Stone-Hulslander

(57) ABSTRACT

Biomarkers useful for identifying a variety of cancers that are responsive to treatment with a combination therapy comprising pembrolizumab, a pembrolizumab variant or an antigen-binding fragment thereof and talimogene laherparepvec are provided. Methods of treating cancers that are resistant to monotherapy with pembrolizumab, a pembrolizumab variant or an antigen-binding fragment thereof are provided. Methods of treating a cancer in a subject having a tumor with a low CD8+ density, a low or negative interferon gamma signature, and/or a low or negative PD-L1 status are also provided.

18 Claims, 29 Drawing Sheets
Specification includes a Sequence Listing.

(56) References Cited

U.S. PATENT DOCUMENTS

| | | | |
|---|---|---|---|
| 5,561,071 A | 10/1996 | Hollenberg | |
| 5,571,639 A | 11/1996 | Hubbell | |
| 5,580,732 A | 12/1996 | Grossman | |
| 5,593,839 A | 1/1997 | Hubbell | |
| 5,624,711 A | 4/1997 | Sundberg | |
| 5,631,734 A | 5/1997 | Stern | |
| 5,661,028 A | 8/1997 | Foote | |
| 5,700,637 A | 12/1997 | Southern | |
| 5,744,305 A | 4/1998 | Fodor | |
| 5,770,456 A | 6/1998 | Holmes | |
| 5,770,722 A | 6/1998 | Lockhart | |
| 5,811,097 A | 9/1998 | Allison et al. | |
| 5,824,318 A | 10/1998 | Mohr et al. | |
| 5,837,832 A | 11/1998 | Chee | |
| 5,848,659 A | 12/1998 | Karg | |
| 5,855,887 A | 1/1999 | Allison et al. | |
| 5,856,101 A | 1/1999 | Hubbell | |
| 5,874,219 A | 2/1999 | Rava | |
| 5,885,837 A | 3/1999 | Winkler | |
| 5,919,523 A | 7/1999 | Sundberg | |
| 6,022,963 A | 2/2000 | McGall | |
| 6,051,227 A | 4/2000 | Allison et al. | |
| 6,077,674 A | 6/2000 | Schleifer | |
| 6,156,501 A | 12/2000 | McGall | |
| 6,207,157 B1 | 3/2001 | Gu et al. | |
| 6,682,736 B1 | 1/2004 | Hanson et al. | |
| 6,764,675 B1 | 7/2004 | Whitley et al. | |
| 6,770,274 B1 | 8/2004 | Martuza et al. | |
| 6,984,720 B1 | 1/2006 | Korman et al. | |
| 7,063,835 B2 | 6/2006 | Coffin | |
| 7,223,593 B2 | 5/2007 | Coffin | |
| 7,488,802 B2 | 2/2009 | Collins et al. | |
| 7,537,924 B2 | 5/2009 | Coffin | |
| 7,605,238 B2 | 10/2009 | Korman et al. | |
| 7,744,899 B2 | 6/2010 | Whitley et al. | |
| 7,749,745 B2 | 7/2010 | Johnson et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 8,273,568 B2 | 9/2012 | Martuza et al. | |
| 8,277,818 B2 | 10/2012 | Coffin | |
| 8,354,509 B2 | 1/2013 | Carven | |
| 8,420,071 B2 | 4/2013 | Whitley et al. | |
| 8,470,577 B2 | 6/2013 | Johnson et al. | |
| 8,680,068 B2 | 3/2014 | Coffin | |
| 8,900,587 B2 | 12/2014 | Carven | |
| 9,464,139 B2 | 10/2016 | Beers et al. | |
| 10,034,938 B2 | 7/2018 | Vandermalde et al. | |
| 10,105,404 B2 | 10/2018 | Mohr et al. | |
| 2009/0220460 A1 | 9/2009 | Coffin | |
| 2011/0118464 A1 | 5/2011 | Chen | |
| 2012/0263677 A1 | 10/2012 | Eagle et al. | |
| 2014/0154215 A1 | 6/2014 | Coffin | |
| 2014/0377221 A1 | 12/2014 | Tufaro et al. | |
| 2019/0070233 A1 | 3/2019 | Yeung et al. | |
| 2020/0000861 A1 | 1/2020 | Conner et al. | |
| 2020/0149067 A1 | 5/2020 | Li et al. | |
| 2020/0353022 A1* | 11/2020 | Gansert | C07K 16/2818 |
| 2021/0138008 A1 | 5/2021 | Tian et al. | |

FOREIGN PATENT DOCUMENTS

| | | |
|---|---|---|
| EP | 2890714 A2 | 7/2015 |
| EP | 3225253 A1 | 10/2017 |
| WO | WO 1996/000007 A1 | 1/1996 |
| WO | WO 1996/039841 A1 | 12/1996 |
| WO | WO 1998/020019 A1 | 5/1998 |
| WO | WO 1998/020020 A2 | 5/1998 |
| WO | WO 1999/007394 A1 | 2/1999 |
| WO | WO 2000/054795 A1 | 9/2000 |
| WO | WO 2001/053506 A2 | 7/2001 |
| WO | WO 2003/042402 A2 | 5/2003 |
| WO | WO 2006/002394 A2 | 1/2006 |
| WO | WO 2008/156712 A1 | 12/2008 |
| WO | WO 2010/036959 A2 | 4/2010 |
| WO | WO 2010/089411 A2 | 8/2010 |
| WO | WO 2011/066342 A2 | 6/2011 |
| WO | WO 2011/082400 A2 | 7/2011 |
| WO | WO 2011/159877 A2 | 12/2011 |
| WO | WO 2011/161699 A2 | 12/2011 |
| WO | WO 2012/135408 A1 | 10/2012 |
| WO | WO 2013/006795 A2 | 1/2013 |
| WO | WO 2014/036412 A2 | 3/2014 |
| WO | WO 2015/031667 A2 | 3/2015 |
| WO | WO 2015/094992 A1 | 6/2015 |
| WO | WO 2015/187835 A2 | 12/2015 |
| WO | WO 2016/009017 A1 | 1/2016 |
| WO | WO 2016/100364 A1 | 6/2016 |
| WO | WO 2016/168133 A1 | 10/2016 |
| WO | WO 2016/196173 A1 | 12/2016 |
| WO | WO 2017/013419 A1 | 1/2017 |
| WO | WO 2017/013421 A1 | 1/2017 |
| WO | WO 2017/118864 A1 | 7/2017 |
| WO | WO 2017/118865 A1 | 7/2017 |
| WO | WO 2017/118866 A1 | 7/2017 |
| WO | WO 2017/118867 A1 | 7/2017 |
| WO | WO 2017/120670 A1 | 7/2017 |
| WO | WO 2017/181420 A1 | 10/2017 |
| WO | WO 2018/006005 A1 | 1/2018 |
| WO | WO 2018/026872 A1 | 2/2018 |
| WO | WO 2018/127713 A1 | 7/2018 |
| WO | WO 2018/201028 A1 | 11/2018 |

OTHER PUBLICATIONS

Gura, T., Systems for Identifying New Drugs Are Often Faulty, Science, 1997, 278:1041-1042 (Year: 1997).*

Kaiser, J., First pass at cancer genoome reveals complex landscape, Science, 2006, 313:1370 (Year: 2006).*

Gerdes et al. Emerging understanding of multiscale tumor heterogeneity, Front. Oncol. Dec. 18, 2014 doi: 10.3389/fonc.2014.00366, pp. 1-12 (Year: 2014).*

NCT02263508 (downloaded from ClinicalTrials.gov, Publication Date: Apr. 26, 2017) (Year: 2017).*

Long et al., "Efficacy analysis of MASTERKEY-265 phase 1b study of talimogene laherparepvec (T-VEC) and pembrolizumab (pembro) for unresectable stage IIIB-IV melanoma", Journal of Clinical Oncology, May 20, 2016, vol. 34, No. 15, Suppl.

U.S. Appl. No. 16/759,476 2020/0353022, filed Apr. 27, 2020, Jennifer Lorraine Gansert.

U.S. Appl. No. 16/648,568 2020/0262919, filed Mar. 18, 2020, Zachary Zimmerman.

Clinicaltrials.gov, "Talimogene Laherparepvec With Pembrolizumab for Recurrent Metastatic Squamous Cell Carcinoma of the Head and Neck (MASTERKEY232 / KEYNOTE-137) (MASTERKEY232)", ClinicalTrials.gov Identifier: NCT02626000, Dec. 10, 2015, obtained from url: https://clinicaltrials.gov/ct2/show/NCT02626000.

Clinicaltrials.gov, "Talimogene Laherparepvec and Pembrolizumab in Treating Patients With Stage III-IV Melanoma", ClinicalTrials. gov Identifier: NCT02965716, Nov. 17, 2016, obtained from url: https://clinicaltrials.gov/ct2/show/NCT02965716.

Erdag et al., "Immunotype and Immunohistologic Characteristics of Tumor-Infiltrating Immune Cells are Associated with Clinical Outcome in Metastatic Melanoma", Cancer Research, 72(5):1070-1080, DOI: 10.1158/0008-5472.CAN-11-3218, 2012.

Harrington et al., "Talimogene Laherparepvec With Pembrolizumab for Recurrent Metastatic Squamous Cell Carcinoma of the Head and Neck (MASTERKEY-232): A Multicenter, Phase 1b Study", Clinical Cancer Research, 26(19):5153-5161, DOI: 10.1158/1078-0432. CCR-20-1170, 2020.

Shah et al., "In Vivo Autofluorescence Imaging of Tumor Heterogeneity in Response to Treatment", Neoplasia, 17(12):862-870, DOI: 10.1016/j.neo.2015,11.006, 2015.

Al-Lazikani et al., "Standard conformations for the canonical structures of immunoglobulins", J Mol Biol., 1997, 273(4): 927-948.

Altschul, "A protein alignment scoring system sensitive at all evolutionary distances", J Mol Evol., 1993, 36(3): 290-300.

(56) References Cited

OTHER PUBLICATIONS

Altschul, "Amino acid substitution matrices from an information theoretic perspective", J Mol Biol., 1991, 219(3): 555-565.
Altschul, "Evaluating the statistical significance of multiple distinct local alignments", Theoretical and Computational Methods in Genome Research, 1997, pp. 1-14.
Altschul, et al., "Basic Local Alignment Search Tool", Journal of Molecular Biology, 1990, vol. 215, No. 3, pp. 403-410.
Altschul, et al., "Gapped BLAST and PSI-BLAST: A New Generation of Protein Database Search Programs", Nucleic Acids Research, 1997, vol. 25, No. 17, pp. 3389-3402.
Ameratunga et al., "PD/L1 and Tumor Infiltrating Lymphocytes as Prognostic Markers in Resected NSCLC", PLoS One, 2016, 11(4): e0153954.
Andtbacka et al., "Talimogene Laherparepvec Improves Durable Response Rate in Patients with Advanced Melanoma", J Clin Oncol., 2015, 33(25): 2780-2788.
Au et al., "Abstract 4146: MultiOmyx multiplexed tumor infiltrating lymphocyte panel provides comprehensive immunophenotyping from a single FFPE slide", Paper presented at: Proceedings of the 107th Annual Meeting of the American Association for Cancer Research (New Orleans, LA: AACR), 2016.
Ayers et al., "IFN-γ-related mRNA profile predicts clinical response to PD-1 blockade", J Clin Invest., 2017, 127(8): 2930-2940.
Ayers et al., "Relationship between immune gene signatures and clinical response to PD/1 blockade with pembrolizumab (MK/3475) in patients with advanced solid tumors", J. Immunotherapy Cancer, 2015, 3(Suppl. 2): P80.
Baert et al., "Influence of immunogenicity on the long-term efficacy of infliximab in Crohn's disease", New Engl J Med., 2003, 348(7): 601-608.
Balar er al., "PD/1 and PD/L1 antibodies in cancer: current status and future directions", Cancer Immunol Immunother., 2017, 66(5): 551/564.
Beniaminovitz et al., "Prevention of rejection in cardiac transplantation by blockade of the interleukin-2 receptor with a monoclonal antibody", New Engl J Med., 2000, 342(9): 613-619.
Blake et al., "Complete intracranial response to talimogene laherparepvec (T/Vec), pembrolizumab and whole brain radiotherapy in a patient with melanoma brain metastases refractory to dual checkpoint/inhibition", J Immunother Cancer, 2018, 6(1): 25.
Blanchard et al., "High-density oligonucleotide arrays", Biosens. Bioelectron., 1996, 11(6/7): 687-690.
Bowtell, "Options available—from start to finish—for obtaining expression data by microarray", Nat Genet., 1999, 21(1 Suppl): 25-32 [published correction appears in Nat Genet., Feb. 1999, 21(2): 241].
Carteron, "Anti-L3T4 Antibody Therapy in Systemic Lupus Erythematosus", Monoclonal Antibodies: Cytokines and Arthritis, Mediators of Inflammation and Therapy, 1991, Chapter 14, pp. 289-312.
Chen et al., "Analysis of Immune Signatures in Longitudinal Tumor Samples Yields Insight into Biomarkers of Response and Mechanisms of Resistance to Immune Checkpoint Blockade", Cancer Discov., 2016, 6(8): 827-837.
Chesney et al., "Melanoma and Other Skin Tumors, Interim safety and efficacy of a randomized (1:1), open-label phase 2 study of talimogene laherparepvec (T) and ipilimumab (I) vs I alone in unresected, stage IIIB-IV melanoma", Ann Oncol, 2016, 27(6): 379-400.
Chothia et al., "Canonical structures for the hypervariable regions of immunoglobulins", J Mol Biol., 1987, 196(4): 901-917.
Chothia et al., "Conformations of immunoglobulin hypervariable regions", Nature, 1989, 342(21/28), 877-883.
Clackson et al., "Making antibody fragments using phage display libraries", Nature, 1991, 352(6336): 624-628.
Clinical Trial / NCT01848834, "Study of Pembrolizumab (MK-3475) in Participants with Advanced Solid Tumors (MK-3475-012/KEYNOTE-012)", University of Chicago Medicine, obtained from url: <https://www.uchicagomedicine.org/find-a-clinical-trial/clinical-trial/0/irb130311>.

Compton, "Nucleic acid sequence/based amplification", Nature, 1991, 350(6313): 91-92.
D'Angelo et al., "Prevalence of tumor/infiltrating lymphocytes and PD/L1 expression in the soft tissue sarcoma microenvironment", Hum Pathol., 2015, 46(3): 357-365.
Daud et al., "Programmed Death/Ligand 1 Expression and Response to the Anti/Programmed Death 1 Antibody Pembrolizumab in Melanoma", J Clin Oncol., 2016, 34, 4102-4109.
David et al., "Protein iodination with solid state lactoperoxidase", Biochemistry, 1974, 13(5): 1014-1021.
Dayhoff et al., "A model of evolutionary change in proteins", Atlas of protein sequence and structure, 1978, 5(3): 345-352.
Dembo et al., "Limit distribution of maximal non-aligned two-sequence segmental score", Ann. Prob., 1994, 22: 2022-2039.
Doi et al., "Pembrolizumab Active in Advanced Esophageal Carcinoma", GCS 2016 (2016 Gastrointestinal Cancers Symposium).
Doi et al., "Updated results for the advanced esophageal carcinoma cohort of the phase 1b KEYNOTE/028 study of pembrolizumab", J Clin Oncol., 2016, 34(15 Suppl): 4046.
Duggan et al., "Expression profiling using cDNA microarrays", Nat Genet., 1999, 21(1 Suppl): 10-14.
Dummer et al., "Combining talimogene laherparepvec with immunotherapies in melanoma and other solid tumors", Cancer Immunol Immunother., 2017, 66(6): 683-695.
Eisenhauer et al., "New response evaluation criteria in solid tumours: revised RECIST guideline (version 1.1)", Eur J Cancer, 2009, 45(2): 228-247.
Galon et al., "Type, density, and location of immune cells within human colorectal tumors predict clinical outcome", Science, 2006, 313(5795): 1960-1964.
Gao et al., "Intratumoral balance of regulatory and cytotoxic T cells is associated with prognosis of hepatocellular carcinoma after resection", J Clin Oncol., 2007, 25(18): 2586-2593.
Garon et al., "Pembrolizumab for the treatment of non/small/cell lung cancer", N Engl J Med., 2015, 372(21): 2018-2028.
Gartrell et al., "Establishing a model for successful immunotherapy with T/vec combined with BRAF inhibition and anti/PD/1 in genetically engineered murine melanoma", Journal for Immunotherapy of Cancer, 2016, 4(1): 109-110.
Geiss et al., "Direct multiplexed measurement of gene expression with color/coded probe pairs", Nat Biotechnol., 2008, 26(3): 317-325.
Gerdes et al., "Highly multiplexed single/cell analysis of formalin/fixed, paraffin/embedded cancer tissue", Proc Natl Acad Sci USA, 2013, 110(29): 11982-11987.
Ghosh et al., "Natalizumab for active Crohn's disease", N Engl J Med., 2003, 348(1): 24-32.
Gish et al., "Identification of protein coding regions by database similarity search", Nat Genet., 1993, 3(3): 266-272.
Gooden et al., "The prognostic influence of tumour/infiltrating lymphocytes in cancer: a systematic review with meta/analysis", Br J Cancer, 2011, 105(1): 93-103.
Hamanishi et al., "PD-1/PD-L1 blockade in cancer treatment: perspectives and issues", Int J Clin Oncol., 2016, 21(3): 462-473.
Hamanishi et al., "Safety and Antitumor Activity of Anti/PD/1 Antibody, Nivolumab, in Patients with Platinum-Resistant Ovarian Cancer", J Clin Oncol., 2015, 33(34): 4015-4022.
Hancock et al., "SIMPLE34: an improved and enhanced implementation for VAX and Sun computers of the SIMPLE algorithm for analysis of clustered repetitive motifs in nucleotide sequences", Comput Appl Biosci., 1994, 10(1): 67-70.
Harrington et al., "Activity and tolerability of BLU-667, a highly potent and selective RET inhibitor, in patients with advances RET-altered thyroid cancers", J Clin Oncol., 2009, vol. 37, No. 15, supplement.
Henikoff et al., "Amino acid substitution matrices from protein blocks", Proc Natl Acad Sci U S A., 1992, 89(22): 10915-10919.
Herbst et al., "Predictive correlates of response to the anti/PD/L1 antibody MPDL3280A in cancer patients", Nature, 2014, 515(7528): 563-567.
Herold et al., "Anti-CD3 monoclonal antibody in new-onset type 1 diabetes mellitus", N Engl J Med., 2002, 346(22): 1692-1698.

(56) References Cited

OTHER PUBLICATIONS

Hoffner et al., "Administration and Handling of Talimogene Laherparepvec: An Intralesional Oncolytic Immunotherapy for Melanoma", Oncol Nurs Forum, 2016, 43(2): 219-226.
Hu et al., "A phase I study of OncoVEXGM-CSF, a second-generation oncolytic herpes simplex virus expressing granulocyte macrophage colony-stimulating factor", Clin Cancer Res., 2006, 12(22): 6737-6747.
Hughes et al., "Expression profiling using microarrays fabricated by an ink-jet oligonucleotide synthesizer", Nat Biotechnol., 2001, 19(4): 342-347.
Hunter et al., "Attenuated, replication-competent herpes simplex virus type 1 mutant G207: safety evaluation of intracerebral injection in nonhuman primates", J Virol., 1999, 73(8): 6319-6326.
Hunter et al., "Preparation of iodine/131 labelled human growth hormone of high specific activity", Nature, 1962, 194: 495-496.
International Preliminary Report on Patentability for PCT International Patent Application No. PCT/US2018/029915, 14 pages.
International Search Report and Written Opinion for PCT International Patent Application No. PCT/US2018/029915, dated Sep. 11, 2018, 19 pages.
Jhawar et al., "Talimogene laherparepvec (T/VEC) as cancer immunotherapy", Pers Med Oncol., 2017, 6(1): 1-17.
Kabat et al., "Unusual distributions of amino acids in complementarity/determining (hypervariable) segments of heavy and light chains of immunoglobulins and their possible roles in specificity of antibody/combining sites", J Biol Chem., 1977, 252(19): 6609-6616.
Kabat, "The structural basis of antibody complementarity", Adv Protein Chem., 1978, 32: 71-75.
Kapadia et al., "CTLA/4 blockade: autoimmunity as treatment", J Clin Oncol., 2005, 23(35): 8926-8928.
Karlin et al., "Applications and statistics for multiple high/scoring segments in molecular sequences", Proc Natl Acad Sci USA, 1993, 90(12): 5873-5877.
Karlin et al., "Methods for assessing the statistical significance of molecular sequence features by using general scoring schemes", Proc Natl Acad Sci USA, 1990, 87(6): 2264-2268.
Kaufman et al., "Local and distant immunity induced by intralesional vaccination with an oncolytic herpes virus encoding GM-CSF in patients with stage IIIc and IV melanoma", Ann Surg Oncol., 2010, 17(3): 718-730.
Kaufman et al., "OPTIM trial: a Phase III trial of an oncolytic herpes virus encoding GM-CSF for unresectable stage III or IV melanoma", Future Oncol., 2010, 6(6): 941-949.
Kim, "Immune checkpoint blockade therapy for bladder cancer treatment", Investig Clin Urol., 2016, 57(Suppl 1): S98-S105.
Köhler et al., "Continuous cultures of fused cells secreting antibody of predefined specificity", vNature, 1975, 256(5517): 495-497.
Le et al., "PD/1 Blockade in Tumors with Mismatch/Repair Deficiency", N Engl J Med., 2015, 372(26): 2509-2520.
Lipshutz et al., "High density synthetic oligonucleotide arrays", Nat Genet., 1999, 21(1 Suppl): 20-24.
Lipsky et al., "Infliximab and methotrexate in the treatment of rheumatoid arthritis. Anti-Tumor Necrosis Factor Trial in Rheumatoid Arthritis with Concomitant Therapy Study Group", N Engl J Med., 2000, 343(22): 1594-1602.
Liu et al., "ICP34.5 deleted herpes simplex virus with enhanced oncolytic, immune stimulating, and anti-tumour properties", Gene Ther., 2003, 10(4): 292-303.
Liu et al., "Randomised, double blind, placebo controlled study of interferon beta-1a in relapsing-remitting multiple sclerosis analysed by area under disability/time curves", J Neurol Neurosurg Psychiatry, 1999, 67(4): 451-456.
Lyford-Pike et al., "Evidence for a role of the PD/1: PD/L1 pathway in immune resistance of HPV/associated head and neck squamous cell carcinoma", Cancer Res., 2013, 73(6): 1733-1741.
Mackie RM et al., "Intralesional injection of herpes simplex virus 1716 in metastatic melanoma", Lancet, 2001, 357(9255): 525-526.
Madden et al., "[9] Applications of network BLAST server", Methods Enzymol., 1996, 266: 131-141.
Malm et al., "Expression profile and in vitro blockade of programmed death/1 in human papillomavirus/negative head and neck squamous cell carcinoma", Head Neck, 2015, 37(8): 1088-1095.
Mandal et al., "The head and neck cancer immune landscape and its immunotherapeutic implications", JCI Insight., 2016, 1(17): e89829.
Markert et al., "Conditionally replicating herpes simplex virus mutant, G207 for the treatment of malignant glioma: results of a phase I trial", Gene Ther., 2000, 7(10): 867-874.
Marks et al., "By-passing immunization. Human antibodies from V-gene libraries displayed on phage", J Mol Biol., 1991, 222(3): 581-597.
Martel et al., "Multiplexed screening assay for mRNA combining nuclease protection with luminescent array detection", Assay Drug Dev Technol., 2002, 1(1 Pt 1):61/71. (2002).
Martin et al., "Paucity of PD/L1 expression in prostate cancer: innate and adaptive immune resistance", Prostate Cancer Prostatic Dis., 2015, 18(4): 325-332.
Maskos et al., "A study of oligonucleotide reassociation using large arrays of oligonucleotides synthesised on a glass support", Nucleic Acids Res., 1993, 21(20): 4663-4669.
Milgrom et al., "Treatment of allergic asthma with monoclonal anti-IgE antibody. rhuMAb-E25 Study Group", N Engl J Med., 1999, 341(26): 1966-1973.
Moy et al., "Biological mechanisms of immune escape and implications for immunotherapy in head and neck squamous cell carcinoma", Eur J Cancer, 2017, 76: 152-166.
National Cancer Institute, "Biomarker", NCI dictionary of cancer terms, obtained from: http://www.cancer.gov/publications/dictionaries/cancer-terms?CdrID=45618, Accessed on Nov. 4, 2020.
Nicolaou et al., "Calicheamicin θ1I: A Rationally Designed Molecule with Extremely Potent and Selective DNA Cleaving Properties and Apoptosis Inducing Activity", Angew. Chem. Int. Ed. Engl., 1994, 33(2): 183-186.
Nygren, "Conjugation of horseradish peroxidase to Fab fragments with different homobifunctional and heterobifunctional cross/linking reagents. A comparative study", J Histochem Cytochem., 1982, 30(5): 407-412.
O'Sullivan et al., "Methods for the Preparation of Enzyme-Antibody Conjugates for use in Enzyme Immunoassay", Methods in Enzymology, 1981, 73: 147-166.
Pain et al., "Preparation of protein A/peroxidase monoconjugate using a heterobifunctional reagent, and its use in enzyme immunoassays", J Immunol Methods, 1981, 40(2): 219-230.
Pardoll, "The blockade of immune checkpoints in cancer immunotherapy", Nat Rev Cancer, 2012, 12(4): 252-264.
Piperno-Neumann et al., "Activity of anti/PD1 drugs in uveal melanoma patients", Journal of Clinical Oncology, 2016, 34(15 Suppl): 9588.
Portielje et al., "IL-12: a promising adjuvant for cancer vaccination", Cancer Immunol Immunother., 2003, 52(3): 133-144.
Powles et al., "MPDL3280A (anti/PD/L1) treatment leads to clinical activity in metastatic bladder cancer", Nature, 2014, 515(7528): 558-562.
Presta, "Selection, design, and engineering of therapeutic antibodies", J Allergy Clin Immunol., 2005, 116(4): 731-737.
Puzanov et al., "Talimogene laherparepvec in combination with ipilimumab in previously untreated, unresectable stage IIIB-IV melanoma", J Clin Oncol, 2016, 34(22): 2619-2626.
Rampling et al., "Toxicity evaluation of replication-competent herpes simplex virus (ICP 34.5 null mutant 1716) in patients with recurrent malignant glioma", Gene Ther., 2000, 7(10): 859-866.
Reese, "Abstract IA24: New frontiers in oncolytic virus therapy", Proceedings of the Second CRI/CIMT/EATI/AACR International Cancer Immunotherapy Conference: Translating Science into Survival, Sep. 25-28, 2016, New York, NY.
Ribas et al., "Association of Pembrolizumab With Tumor Response and Survival Among Patients with Advanced Melanoma", JAMA, 2016, 315(15): 1600-1609 [published correction appears in JAMA, Jun. 14, 2016, 315(22): 2472].
Ribas et al., "Association of response to programmed death receptor 1 (PD/1) blockade with pembrolizumab (MK/3475) with an interferon/inflammatory immune gene signature", J Clin Oncol., 2015, 33(15 Suppl): 3001.

(56) References Cited

OTHER PUBLICATIONS

Ribas et al., "Oncolytic Virotherapy Promotes Intratumoral T Cell Infiltration and Improves Anti-PD-1 Immunotherapy", Cell, 2018, 170(6): 1109-1119.
Ribas, "Adaptive Immune Resistance: How Cancer Protects from Immune Attack", Cancer Discov., 2015, 5(9): 915-919.
Robert et al., "Nivolumab in previously untreated melanoma without BRAF mutation", N Engl J Med., 2015, 372(4): 320-330.
Robert et al., "Pembrolizumab versus Ipilimumab in Advanced Melanoma", N Engl J Med.,2015, 372(26): 2521-2532.
Rojo et al., "Review of imaging solutions for integrated quantitative immunohistochemistry in the Pathology daily practice", Folia Histochem Cytobiol., 2009, 47(3): 349-354.
Schena et al., "Microarrays: biotechnology's discovery platform for functional genomics", Trends Biotechnol., 1998, 16(7):301-306.
Schena, "Genome analysis with gene expression microarrays", Bioessays, 1996, 18(5): 427-431.
Sharma et al., "The future of immune checkpoint therapy", Science, 2015, 348(6230): 56-61.
Slamon et al., "Use of chemotherapy plus a monoclonal antibody against HER2 for metastatic breast cancer that overexpresses HER2", N Engl J Med., 2001, 344(11): 783-792.
Stanton et al., "Variation in the Incidence and Magnitude of Tumor/Infiltrating Lymphocytes in Breast Cancer Subtypes: A Systematic Review", JAMA Oncol., 2016, 2(10): 1354-1360.
States et al., "Improved sensitivity of nucleic acid database searches using application-specific scoring matrices", Methods: A Companion to Meth. in Enzymol., 1991, 3(1): 66-70.
Sundaresan et al., "Attenuated, replication-competent herpes simplex virus type 1 mutant G207: safety evaluation in mice", J Virol., 2000, 74(8): 3832-3841.
Taube et al., "Association of PD/1, PD/1 ligands, and other features of the tumor immune microenvironment with response to anti/PD/1 therapy", Clin Cancer Res., 2014, 20(19): 5064-5074.
Topalian et al., "Safety, activity, and immune correlates of anti/PD/1 antibody in cancer", N Engl J Med., 2012. 366(26): 2443-2454.
Tumeh et al., "PD/1 blockade induces responses by inhibiting adaptive immune resistance", Nature, 2014, 515(7528): 568-571.
Weber, "Assessing tumor response to therapy", J Nucl Med., 2009, 50: 1S-10S.
Wolchok et al., "Guidelines for the evaluation of immune therapy activity in solid tumors: immune/related response criteria", Clin Cancer Res., 2009, 15(23): 7412-7420.
Woller et al., "Viral Infection of Tumors Overcomes Resistance to PD/1/immunotherapy by Broadening Neoantigenome/directed T/cell Responses", Mol Ther., 2015, 23(10): 1630-1640.
Wong et al., "Abstract A081: A PD-L1-targeted Probody provides antitumor efficacy while minimizing induction of systemic autoimmunity", Cancer Immunol Res., 2016, 4(1): Suppl.
Wootton et al., "Statistics of local complexity in amino acid sequences and sequence databases", Comput Chem, 1993, 17(2): 149-163.
Yang et al., "A randomized trial of bevacizumab, an anti-vascular endothelial growth factor antibody, for metastatic renal cancer", N Engl J Med., 2003, 349(5): 427-434.
Zhang et al., "PowerBLAST: a new network BLAST application for interactive or automated sequence analysis and annotation", Genome Res., 1997, 7(6): 649-656.
Moehler et al., "Immunotherapy in gastrointestinal cancer: Recent results, current studies and future perspectives", European Journal of Cancer, May 2016, 59: 160-170.
Tumeh et al., "PD-1 blockade induces responses by inhibiting adaptive immune resistance", Nature, Nov. 27, 2014, 515(7528): 568-571.
Extended European Search Report for European Patent Application No. 22163106.2, dated Aug. 31, 2022.
Chang et al., "Phase I dose-escalation study of talimogene leherparepvec (T-VEC) for advanced pancreatic cancer (ca)", 2012 ASCO Meeting, Abstract e14546, J Clin Oncol., 2012, 30(Suppl): e14546.

Kaufman et al., "Optim: A randomized phase III trial to evaluate the efficacy and safety of talimogene leherparepvec (T-VEC) compared with subcutaneously (sc) administered GM-CSF for the treatment (tx) of unresectable stage IIIc, IIIc, and IV melanoma", 2012 ASCO Meeting, Abstract TPS8604; J Clin Oncol., 2012, 30(Suppl): TPS8604.
American Cancer Society, "Melanoma Skin Cancer: How is Melanoma Skin Cancer Staged?" http://www.cancer.org/cancer/skincancer-melanoma/detailedguide/melanoma-skin-cancer-staging, revised Feb. 1, 2016.
Amgen, "Study of Talimogene Laherparepvec In Children With Advanced Non CNS Tumors", ClinicalTrials.gov ID: NCT02756845. Ver.1, Posted Apr. 27, 2016.
Andtbacka et al., "Interim analysis of a randomized, open-label phase 2 study of talimogene laherparepvec (T-VEC) neoadjuvant treatment (neotx) plus surgery (surgx) vs surgx for resectable stage IIIB-IVM1a melanoma (MEL)," Journal of Clinical Oncology 36(15_Suppl): 9508-9508 (2018).
Anonymous, "Study of Talimogene Laherparepvec in Children with Advanced Non CNS Tumors," ClinicalTrials.gov, NCT02756845, Jan. 20, 2017, retrieved from the Internet: URL: https://web.archive.org/web/20170120035152/https://clinicaltrials.gov/ct2/show/NCT02756845.
Apolonio et al., "Oncolytic virus therapy in cancer: A current review", World J Virol., Sep. 25, 2021, 10(5): 229-255.
Balch et al., "Final Version of 2009 AJCC Melanoma Staging and Classification," Journal of Clinical Oncology, Dec. 2009, 27(36): 6199-6206.
Biovex, "Highlights of Prescribing Information—These highlights do not include all the information needed to use IMLYGIC TM safely and effectively. See full prescribing information for IMLYGIC (talimogene laherparepvec), suspension for intralesional injection," Oct. 1, 2015, XP055472051, retrieved from the Internet: URL: https://www.fda.gov/downloads/BiologicsBloodVaccines/CellularGeneTherapyProducts/ApprovedProducts/UCM469575.pdf.
Blois et al., "Malignant melanoma of the skin" Cancer, Oct. 1983, 52(7): 1330- 1341.
Bommareddy et al., "Talimogen eLaherparepvec (T-VEC) and Other Oncolytic Virusesfor the Treatment of Melanoma," American Journal of Clinical Dermatology 18(1):1-15 (2017).
Brignone et al., "A Soluble Form of Lymphocyte Activation Gene-3 (IMP321) Induces Activation of a Large Range of Human Effector Cytotoxic Cells," Journal of Immunology 179:4202-4211 (2007).
Cassady and Parker, "Herpesvirus Vectors for Therapy of Brian Tumors," The Open Virology Journal 4:103-108 (2010).
Chemnitz et al., "SHP-1 and SHP-2 Associate with Immunoreceptor Tyrosine-Based Switch Motif of Programmed Death 1 upon Primary Human T Cell Stimulation, but Only Receptor Ligation Prevents T Cell Activation," The Journal of Immunology 173(2):945-954 (2004).
Chen et al., "Oncology Meets Immunology: The Cancer-Immunity Cycle," Immunity 39:1-10 (2013).
Clark et al., "Model predicting survival in stage 1 melanoma based on tumor progression," Journal of National Cancer Institute, Dec. 1989, 81(24): 1893-1904.
Cripe et al., "A phase I dose-escalation study of intratumoral herpes simplex virus-1 mutant HSV1716 in pediatric/young adult patients with refractory non-central nervous system solid tumors", 2013 ASCO Annual Meeting, Abs. 10047.
Currier et al., "VEGF Blockade Enables Oncolytic Cancer Virotherapy in Part by Modulating Intratumoral Myeloid Cells," Molecular Therapy 21(5): 1014-1023 (2013).
Dummer et al., "Neoadjuvant talimogene laherparepvec plus surgery versus surgery alone for resectable stage IIIB-IVM1a melanoma: a randomized, open-label, phase 2 trial," Nature Medicine 27(10):1789-1796 (2021).
Dummer et al., "Combining talimogene laherparepvac with immunotherapies in melanoma and other solid tumors," Cancer Immunology Immunotherapy 66(6):683-695 (2017).
Dummer et al., "Final 5-Year Follow-Up Results Evaluating Neoadjuvant Talimogene Laherparepvec Plus Surgery in Advanced Melanoma: A Randomized Clinical Trial," JAMA Oncology, published online Aug. 10, 2023, doi:10.1001/jamaoncol.2023.2789.

(56) References Cited

OTHER PUBLICATIONS

Eisenhaurer et al., "New response evaluation criteria in solid tumours: Revised RECIST guideline (version 1.1)," Eur J Cancer 45: 228-247 (2009).
Eshun et al., "VEGF blockade decreases the tumor uptake of systemic oncolytic herpes virus but enhances therapeutic efficacy when given after virotherapy," Gene Therapy 17(7):922-929 (2010).
European Medicines Agency (EMA), Imlygic: Assessment Report, Oct. 22, 2015.
Ferrucci et al., "Talimogene Laherparepvec (T-VEC): An Intralesional Cancer Immunotherapy for Advanced Melanoma", Cancers (Basel), Mar. 18, 2021, 13(6):1383.
Flemming, "PD1 makes waves in anticancer immunotherapy," Nat Rev Drug Discov. 11(8): 601 (2012).
Fong et al., "Potentiating Endogenous Antitumor Immunity to Prostate Cancer through Combination Immunotherapy with CTLA4 Blockade and GM-CSF," Cancer Research, Jan. 2009, 69(2): 609-615.
Fourcade et al., "Upregulation of Tim-3 and PD-1 expression is associated with tumor antigen-secific CD8+T cell dysfunction in melanoma patients," J. Exp. Med. 207(10):2175-2186 (2010).
Franks et al., "New Anticancer Immunotherapies," Anticancer Research 32: 2439-2454 (2012).
Friedman et al., "Pediatric medulloblastoma xenografts including molecular subgroup 3 and CD133+ and CD15+ cells are sensitive to killing by oncolytic herpes simplex viruses", Neuro Oncol., Feb. 2016, 18(2): 227-235, Epublished Jul. 16, 2015.
Fukuhara et al., "Oncolytic virus therapy: A new era of cancer treatment at dawn," Cancer Science 107(10): 1373-1379 (2016).
Garnock-Jones, "Talimogene Laherparepvec: A Review in Unresectable Metastatic Melanoma," BioDrugs 30(5):461-468 (2016).
Geary et al., "Prostate cancer vaccines: Update on clinical development," Oncolmmunology 2:5, e24523; May 2013, pp. 1-8.
Ghajar-Rahimi et al., "Clinical advances in oncolytic virotherapy for pediatric brain tumors", Pharmacol Ther., Nov. 2022, 239: 108193, Epublished Apr. 26, 2022.
Goldberg et al., "Biologic Activity of Autologous, Granulocyte-Macrophage Colony Stimulating Factor Secreting Alveolar Soft Parts Sarcoma and Clear Cell Sarcoma Vaccines," Clin Cancer Res. Jul. 1, 20155; 21(14): 3178-3186. doi:10.1158/1078-0432.CCR-14-2932.
Grilley-Olson et al., "A dose-escalation phase I study of oral pan-CDK inhibitor BAY 1000394 in patients with advanced solid tumors: Dose escalation with an intermittent 28 days on/14 days off schedule," Journal of Clinical Oncology, May 20, 2012, vol. 30, No. 15, suppl. pt. 1, 3046.
Grosso et al., "CTLA-4 blockade in tumor models: an overview of preclinical and translational research," Cancer Immunity 13:5 (2013).
Harrington et al., "Phase I Study of Lapatinib in Combination With Chemoradiation in Patients With Locally Advanced Squamous Cell Carcinoma of the Head and Neck," Journal of Clinical Oncology, Mar. 2009, 27(7): 1100-1107.
Harrington et al., "Phase I/II dose escalation study of OncoVexGM-CSF and chemoradiotherapy (CRT) in untreated stage III/IV squamous cell cancer of the head and neck (SCCHN)," Journal of Clinical Oncology 27(15a):abstract 6018 (2009).
Harrington et al., "Phase I/II Study of Oncolytic HSVGM-CSF in Combination with Radiotherapy and Cisplatin in Untreated Stage III/IV Squamous Cell Cancer of the Head and Neck," Clinical Cancer Research (16)15:4005-4015 (2010).
Hodi et al., "Improved Survival with Ipilimumab in Patients with Metastatic Melanoma," The New England Journal of Medicine, Aug. 2010, 363(8): 711-723.
Hodi et al., "Sargramostim plus Ipilimumab vs Ipilimumab Alone for Treatment of Metastatic Melanoma: A Randomized Clinical Trial," JAMA. Nov. 5, 2014; 312(17): 1744-1753. doi:10.1001/jama.2014.13943, pp. 1-21.
Hoeller et al., "Systematic review of the use of granulocyte-macrophage colony-stimulating factor in patients with advanced melanoma," Cancer Immunol Immunother (2016) 65:1015-1034, DOI 10.1007/s00262-016-1860-3.
Hu et al., "A Phase I Study of OncoVEXGM-CSF, a Second-Generation Oncolytic Herpes Simplex Virus Expressing Granulocyte Macrophage Colony-Stimulating Factor," Clinical Cancer Research (American Association for Cancer Research), Nov. 2006, 12(22): 6737-6747.
Hunter et al., "Attenuated, Replication-Competent Herpes Simplex Virus Type 1 Mutant G207: Safety Evaluation of Intracerebral Injection in Nonhuman Primates," J Virol. 73 (8): 6319-6326 (1999).
IPILIMUMAB: Trademark details. Bristol-Myers Squibb, Co.; Serial No. 77273787, filed Sep. 7, 2007.
Jaffee et al., "Novel Allogeneic Granulocyte-Macrophage Colony-Stimulating Factor-Secreting Tumor Vaccine for Pancreatic Cancer: A Phase I Trial of Safety and Immune Activation," Journal of Clinical Oncology 19(1): 145-156 (2001).
Jemal et al., "Cancer Statistics, 2006" CA Cancer J. Clin. 2006, 56(2): 106-130.
Johnson et al., "Talimogene laherparepvec (T-VEC) for the treatment of advanced melanoma," Immunotherapy 7(6):611-619 (2015).
Kapadia, D. et al., "CTLA-4 blockade: autoimmunity as treatment," Journal of Clinical Oncology, Dec. 2005, 23(35): 8926-8928.
Karakousis et al., "Predictors of Regional Nodal Disease in Patients With Thin Melanomas," Annals of Surgical Oncology, Apr. 2006, 13(4): 533-541.
Kaufman et al., "Local and Distant Immunity Induced by Intralesional Vaccination with an Oncolytic Herpes Virus Encoding GM-CSF in Patients with Stage IIIc and IV Melanoma," Annals of Surgical Oncology, Springer-Verlag, NE, Published online Nov. 14, 2009, 17(3): 718-730.
Kaufman et al., "OPTIM trial: a Phase III trial of an oncolytic herpes virus encoding GM-CSF for unresectable stage III or IV melanoma," Future Oncology 6(6): 941-949 (2010).
Kaufman, Combination Immunotherapy for Melanoma, Clinical Review & Education From the JAMA Network, pp. 387-388, JAMA Oncology, Jun. 2015, 1(3):387-388.
Kimura et al., "Vascular Endothelial Growth Factor Promotes Cell-Cycle Transition from G0 to G1 phase in Subcultured Endothelial Cells of Diabetic Rat Thoracic Aorta," Jpn. J. Pharmacol. 83(1):47-55 (2000).
Koh, "Cutaneous melanoma" NEMJ.org, Jul. 1991, 325(3): 171-82.
Komenaka et al., "Immunotherapy for Melanoma," Clinics in Dermatology 2004;22:251-265.
Kwek et al., "GM-CSF and ipilimumab therapy in metastatic melanoma: Clinical outcomes and immunologic responses," Oncoimmunology 2016, vol. 5, No. 4, e1101204 (10 pages), http://dx.doi.org/10.1080/2162402X.2015.1101204.
Laheru et al., "Allogeneic GM-CSF Secreting Tumor Immunotherapy (GVAX®)Alone or in Sequence with Cyclophosphamide for Metastatic Pancreatic Cancer: A Pilot Study of Safety, Feasibility and Immune Activation," Clin Cancer Res. Mar. 1, 2008; 14(5): 1455-1463. doi:10.1158/1078-0432.CCR-07-0371.
Le et al., "Evaluation of Ipilimumab in combination with allogeneic pancreatic tumor cells transfected with a GM-CSF gene in previously treated pancreatic cancer," J Immunother. Sep. 2013; 36(7): 382-389. doi:10.1097/CJI.0b013e31829fb7a2.
Le, Dung T., Safety and Survival With GVAX Pancreas Prime and Listeria Monocytogenes-Expressing Mesothelin (CRS-207) Boost Vaccines for Metastatic Pancreatic Cancer, Journal of clinical Oncology, vol. 33, No. 12, Apr. 20, 2015, pp. 1325-1333.
Ledford, "Cancer-fighting viruses win approval", Nature, Oct. 29, 2015, 526(7575): 622-623.
Leon et al., "The Prognostic Implications of Microscopic Satellites in Patients with Clinical Stage 1 Melanoma," Archives of Surgery, Dec. 1991, 126(2): 1461-1468.
Lipson et al., "Safety and immunologic correlates of Melanoma GVAX, a GM-CSF secreting allogeneic melanoma cell vaccine administered in the adjuvant setting," J Transl Med (2015) 13:214, DOI 10.1186/s12967-015-0572-3.
Liu et al., "ICP34.5 deleted herpes simplex virus with enhanced oncolytic, immune stimulating, and anti-tumour properties," Gene Ther. 10 (4): 292-303 (2003).

(56) References Cited

OTHER PUBLICATIONS

Liu et al., "Preclinical evaluation of herpes simplex virus armed with granulocyte-macrophage colony-stimulating factor in pancreatic carcinoma," World Journal of Gastroenterology 19(31):5138-5143 (2013).
Loo et al., "Development of an Fc-Enhanced Anti-B7-H3 Monoclonal Antibody with Potent Antitumor Activity," Clinical Cancer Research, Jul. 2012, 18(14): 3834-3845.
Luke et al., "Single Institution Experience of Ipilimumab 3 mg/kg with Sargramostim (GM-CSF) in Metastatic Melanoma," Cancer Immunol Res. Sep. 2015; 3(9): 986-991. doi:10.1158/2326-6066. CIR-15-0066.
Mackie et al., "Intralesional injection of herpes simplex virus 1716 in metastatic melanoma," Lancet 357(9255): 525-526 (Feb. 2001).
MacLean et al., "Herpes simplex virus type 1 deletion variants 1714 and 1716 pinpoint neurovirulence-related sequences in Glasgow strain 17+ between immediate early gene 1 and the 'a' sequence," Journal of General Virology 72:631-639 (1991).
Markert et al., "Conditionally replicating herpes simplex virus mutant, G207 for the treatment of malignant glioma: results of a phase I trial," Gene Therapy, May 2000, 7(10): 867-874.
Meignier et al., "In Vivo Behavior of Genetically Engineered Herpes Simplex Viruses R7017 and R7020: Construction and Evaluation in Rodents," J. Infect. Dis. 159(3): 602-614 (1988).
Miller et al., "Development of a Syngenic Murine B16 Cell Line-Derived Melanoma Susceptible to Destruction by Neuroattenuated HSV-1," Molecular Therapy 3(2): 160-168 (2001).
Mineta et al., "Attenuated multi-mutate herpes simplex virus-1 for the treatment of malignant gliomas," Nat Med. 1(9):938-943 (1995).
Mohr et al., "A herpesvirus genetic element which affects translation in the absence of the viral GADD34 function," The EMBO Journal 15(17):4759-4766 (1996).
Monga et al., "Intratumoral talimogene laherparepvec injection with concurrent preoperative radiation in patients with locally advanced soft-tissue sarcoma of the trunk and extremities: phase IB/II trial," Journal for Immuno Therapy of Cancer 9:1-11 (2021).
Moreno et al., "A phase 1, first-in-child, multicenter study to evaluate the safety and efficacy of the oncolytic herpes virus talimogene laherparepvec in pediatric patients with advanced solid tumors," Frontiers in Pediatrics 11:1183295 (2023).
Mulvey et al., "A Herpesvirus Ribosome-Associated, RNA-Binding Protein Confers a Growth Advantage upon Mutants Deficient in a GADD34-Related Function," Journal of Virology 73(4):3375-3385 (1999).
Napolitano et al., "It is finally time for adjuvant therapy in melanoma," Cancer Treatment Reviews 69:101-111 (2018).
Natarajan et al., "Novel Immunotherapeutic Agents and Small Molecule Antagonists of Signalling Kinases for the Treatment of Metastatic Melanoma," Drugs 71(10): 1233-1250 (2011).
Nemunaitis et al., "Phase 1/2 trial of autologous tumor mixed with an allogeneic GVAX® vaccine in advanced-stage non-small-cell lung cancer," Cancer Gene Therapy (2006) 13, 555-562.
NIH—National Cancer Institute, "Childhood Medulloblastoma and Other Central Nervous System Embryonal Tumors Treatment PDQ®)-Health Professional Version", https://www.cancer.gov/types/brain/hp/child-cns-embryonal-treatment-pdq, Updated Feb. 14, 2024.
Nocentini et al., "A new member of the tumor necrosis factor/nerve growth factor receptor family inhibits T cell receptor-induced apoptosis," Proc. Natl. Acad. Sci. USA 94:6216-6221 (1997).
Okamura et al., "Inorganic arsenic exposure induces E2F-dependent G0/G1 arrest via an increase in retinoblastoma family protein p130 in B-cell lymphoma A20 cells," Genes to Cells 18:839-849 (2013).
Overett et al., "Surgical Treatment of Distant Metastatic Melanoma: Indications and Results," Cancer, Sep. 1985, 56(5): 1222-1230.
Pardoll, "The blockade of immune checkpoints in cancer immunotherapy," www.nature.com/reviews/cancer, Apr. 2012, vol. 12: 252-264.
Piasecki et al., "Talimogene laherparepvec increases the anti-tumor efficacy of the anti-PD-1 immune checkpoint blockade," presentation abstract, 1 p. 2015.
Puzanov et al., "Talimogene Laherparepvec in Combination with Ipilimumab in Previously Untreated, Unresectable Stage IIIB-IV Melanoma," Journal of Clinical Oncology 34(22): 2619-2626 (2016).
Puzanov et al., "Phase 1b results from a multicenter trial of talimogene laherparepvec+ ipilimumab (T-VEC+ipi) in previously untreated, unresected stage IIIB-IV melanoma," Results and Interpretations of ASCO Presentations 2015: Interdisciplinary Global Conference on News in Melanoma/Skin Cancer, 5th European Post-Chicago Melanoma/Skin Cancer Meeting, Leonardo Royal Hotel, Munich, Germany (Jun. 26, 2015).
Quezada, S et al., "CTLA4 blockade and GM-CSF combination immunotherapy alters the intratumor balance of effector and regulatory T cells," J Clin Invest. Jul. 3, 2006; 116(7): 1935-1945.
Rampling et al., "Toxicity evaluation of replication-competent herpes simplex virus (ICP 34:5 null mutant 1716) in patients with recurrent malignant glioma," Gene Therapy, May 2000 7(10): 859-866.
Rehman et al., "Into the clinic: Talimogene laherparepvec (T-VEC), a first-in-class intratumoral oncolytic viral therapy", J Immunother Cancer, Sep. 20, 2016, 4: 53.
Reske et al., "Glycoprotein-Dependent and TLR2-Independent Innate Immune Recognition of Herpes Simplex Virus-1 by Dendritic Cells," Journal of Immunology 180(11):7525-7536 (2008).
Ressler et al., "Efficacy and tolerability of neoadjuvant treatment with T-VEC in difficult to resect primary basal cell carcinoma: a phase II clinical trial (NeoBCC)," poster abstract, ESMO Congress, 2022.
Richtig, "Asco Congress 2018: melanoma treatment," Magazine of European Medical Oncology 11:261-265 (2018).
Ries et al., "The annual report to the nation on the status of cancer, 1973-1997, with a special section on colorectal cancer," Cancer, May 2000, 88(10): 2398-2424.
Rieth et al., "Neoadjuvant Intratumoral Talimogene Laherparepvec (TVEC) with Concurrent Radiation in Extremity and Trunk Soft-Tissue Sarcomas," poster abstract, University of Iowa Healthcare, CTOS Annual Meeting, 2022.
Robert et al., "Ipilimumab plus Decarbazine for Previously Untreated Metastatic Melanoma," The New England Journal of Medicine, Jun. 2011, 364(26): 2517-2526.
Russell et al., "Oncolytic virotherapy," Nature Biotechnology 30(7):658-670 (2012).
Sakuishi et al., "Targeting Tim-3 and PD-1 pathways to reverse T cell exhaustion and restore anti-tumor immunity," J. Exp. Med. 207(10):2187-2194 (2010).
Senzer et al., "Phase II Clinical Trial of a Granulocyte-Macrophage Colony-Stimulating Factor-Encoding, Second-Generation Oncolytic Herpesvirus in Patients With Unresectable Metastatic Melanoma," Journal of Clinical Oncology, Dec. 2009, 27(34): 5763-5771.
Shumate et al., "The Prognostic Implications of Location for Scalp Melanoma," The American Journal of Surgery, Oct. 1991, 162(4): 315-319.
Siegel et al., "Cancer Statistics," CA Cancer J. Clin, 2012, 62(1): 10-29.
Sierro et al., "Combination of lentivector immunization and low-dose chemotherapy or PD-1/PD-L1 blocking primes self-reactive T cells and induces anti-tumor immunity," Eur. J. Immunol. 41(8): 2217-2228 (2011).
Silk, National Cancer Institute (NCI), ClinicalTrials.gov Identifier: NCT02978625, "Talimogene Laherparepvec and Nivolumab in Treating Patients With Refractory Lymphomas or Advanced or Refractory Non-melanoma Skin Cancers", First posted: Dec. 1, 2016.
Sivendran et al., "Herpes simplex virus oncolytic vaccine therapy in melanoma," Expert Opinion on Biological Therapy 10(7): 1145-1153 (2010).
Sivendran et al., "Melanoma Immunotherapy," Mount Sinai Journal of Medicine: A Journal of Translational and Personalized Medicine, abstract, published online Nov. 23, 2010, vol. 77: 620-642.
Slinguff et al., "The Annual Risk of Melanoma Progression," Cancer, Mar. 1992, 70(7): 1917-1927.
Soares et al., "PD-1/PD-L1 blockade together with vaccine therapy facilitates effector T cell infiltration into pancreatic tumors," J Immunother. Jan. 2015; 38(1): 1-11.

(56) References Cited

OTHER PUBLICATIONS

Soliman et al., "Oncolytic T-VEC virotherapy plus neoadjuvant chemotherapy in non-metastatic triple-negative breast cancer: a phase 2 trial," Nature Medicine 29:450-457 (2023).
Spring et al., "Abstract GS2-03: Pathological complete response after neoadjuvant chemotherapy and impact on breast cancer recurrence and mortality, stratified by breast cancer subtypes and adjuvant chemotherapy usage: individual patient-level meta-analyses of over 27,000 patients," Cancer Res 79(4_Supplement), 2 pages (2019).
Streby et al., "Intratumoral Injection of HSV1716, an Oncolytic Herpes Virus, Is Safe and Shows Evidence of Immune Response and Viral Replication in Young Cancer Patients", Clin Cancer Res., Jul. 15, 2017, 23(14): 3566-3574, Epublished May 11, 2017.
Sundaresan, P et al., "Attenuated, replication-competent herpes simplex virus type 1 mutant G207: safety evaluation in mice," Journal of Virology, Apr. 2000, 74(8): 3832-3841.
Thompson et al., "DNA Sequence and RNA Transcription through a Site of Recombination in a Non-neurovirulent Herpes Simplex Virus Intertypic Recombinant," Virus Genes 1(3): 275-286 (1988).
Todo et al., "Oncolytic herpes simplex virus vector with enhanced MHC class I presentation and tumor cell killing," Proc Natl Acad Sci USA 98 (11): 6396-6401 (2001).
Tsuji et al., "Pediatric (Non-CNS) Tumors", Handbook of Evidence-Based Radiation Oncology, Jan. 1, 2010.
Tykodi et al., "PD-1/PD-L1 pathway as a target for cancer immunotherapy: safety and clinical activity of BMS-936559, an anti-PD-L1 antibody, in patients with solid tumors," DOI: 10.1200/jco.2012.30.15_suppl.2510, Journal of Clinical Oncology 30(15), 4 pages (2012).
Van Elsas et al., "Combination Immunotherapy of B16 Melanoma Using Anti-Cytotoxic T Lymphocyte-Associated Antigen 4 (CTLA-4) And Granulocyte/Macrophage Colony-Stimulating Factor (GM-CSF)-Producing Vaccines Induces Rejection Of Subcutaneous And Metastatic Tumors Accompanied By Autoimmune Depigmentation," Journal of Experimental Medicine, Aug. 2, 1999, 190(3): 355-366.
VARGHESE and RABKIN, "Oncolytic herpes simplex virus vectors for cancer virotherapy," Cancer Gene Ther. 9:967-978 (2002).
Velcheti et al., "Basic Overview of Current Immunotherapy Approaches in Cancer", Am Soc Clin Oncol Educ Book, 2016, 35: 298-308.
Wang et al., "Neuroblastomas vary widely in their sensitivities to herpes simplex virotherapy unrelated to virus receptors and susceptibility," Gene Therapy 23:135-143 (2016).
Weber, "Ipilimumab: controversies in its development, utility and autoimmune adverse events," Cancer Immunology, Immunotherapy 58(5):823-830 (2009).
Weber, J., "Immunotherapy for Melanoma," Curr. Opin. Oncol., Mar. 2011, 23(2):163-169.
Wolchok et al., "Guidelines for the Evaluation of Immune Therapy Activity in Solid Tumors: Immune-Related Response Criteria," Clinical Cancer Research (American Association for Cancer Research), Dec. 2009, 15(23): 7412-7420.
Zhang et al., "Bevacizumab with Angiostatin-armed oHSV Increases Antiangiogenesis and Decreases Bevacizumab-induced Invasion in U87 Glioma," Molecular Therapy 20(1):37-45 (2012).
Zhu et al., "Advances in immunotherapy in gastrointestinal cancer," Tumor 36(11):1280-1286 (2016) with English abstract.
Zhu et al., "Vascular endothelial growth factor promotes proliferation of cortical neuron precursors by regulating E2F expression," The FASEB Journal 17(2): 186-193 (2018).
Zijlker et al., "Neoadjuvant T-VEC + nivolumab combination therapy for resectable early metastatic (stage IIIB/C/D-IV M1a) melanoma with injectable disease: NIVEC trial," Journal of Clinical Oncology 41(16_suppl):9546 (2023).

\* cited by examiner

Number of patients for which biomarker results were available

| Assay | Week −5 Baseline | Week 0 Injected | Week 0 Non-injected | Week 24 Injected | Week 24 Non-injected |
|---|---|---|---|---|---|
| IHC PD-L1 | 23 | 10 | 4 | 6 | 1 |
| IHC CD8, GZMB<br>Total<br>Tumor<br>Cancer-cell depleted | 19<br>18<br>1 | 15<br>10<br>5 | 5<br>5<br>0 | 4<br>0<br>4 | 1<br>0<br>1 |
| Multi-Omyx | 13 | 13 | 4 | 3 | 0 |
| NanoString | 18 | 9 | 6 | 0 | 0 |

*Fig. 6B*

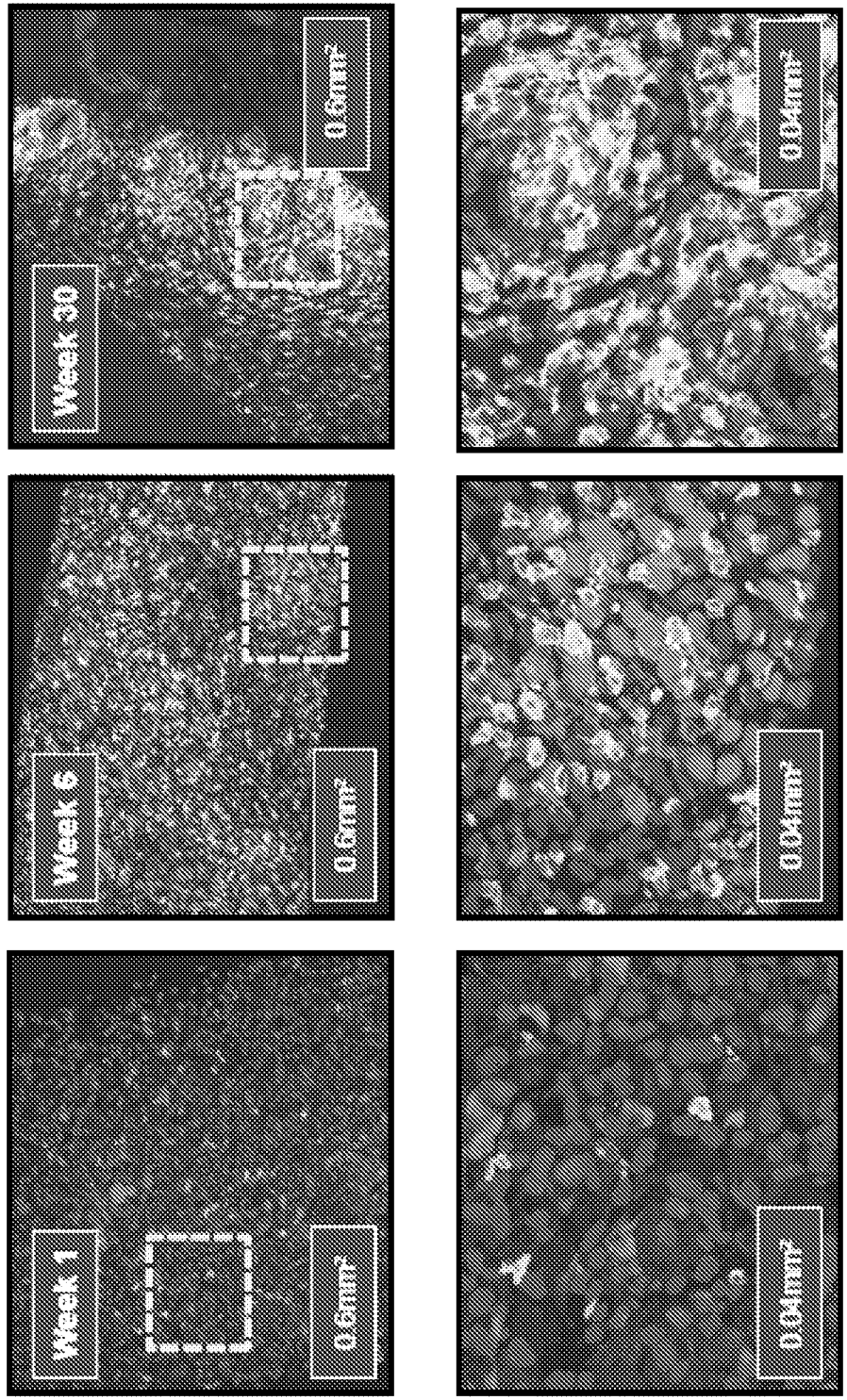

| Gene Id | Target Transcript NCBI Accession # | Gene Id | Target Transcript NCBI Accession # |
|---|---|---|---|
| ABCF1 | NM_001090.2 | IL2 | NM_000586.2 |
| ALAS1 | NM_000688.4 | IL4 | NM_000589.2 |
| AXL | NM_021913.2 | ITGAL (CD11a) | NM_002209.2 |
| Adipoq | NM_004797.2 | ITGAM (CD11b) | NM_000632.3 |
| Areg | NM_001657.2 | Icam1 | NM_000201.1 |
| Arg1 | NM_000045.2 | Icos | NM_012092.2 |
| Arg2 | NM_001172.3 | IcosL (B7-H2) | NM_015259.4 |
| Atp6v0d2 | NM_152565.1 | Id2 | NM_002166.4 |
| Atp8b4 | NM_024837.2 | Ido1 (Indo) | NM_002164.3 |
| B7-H3 (CD276) | NM_001024736.1 | Ifi16 | NM_005531.1 |
| B7-H4 (VTCN1) | NM_024626.2 | Ifitm1 | NM_003641.3 |
| BAGE | NM_001187.1 | Ifngr2 | NM_005534.3 |
| BCL6 | NM_138931.1 | Igf1 | NM_000618.3 |
| BLNK | NM_013314.2 | Igj | NM_144646.3 |
| Batf | NM_006399.3 | Ikzf3 | NM_012481.3 |
| Bcl11a | NM_022893.3 | Ing1 | NM_198219.1 |
| Bcl11b | NM_022898.1 | Ing2 | NM_001564.2 |
| Bst1 | NM_004334.2 | Insr | NM_000208.1 |
| Bt1a | NM_181780.2 | Irf1 | NM_002198.1 |
| CADM1 | NM_014333.3 | Irf2 | NM_002199.2 |
| CD112 | NM_002856.2 | Irf4 | NM_002460.1 |
| CD113 | NM_015480.2 | Irf6 | NM_006147.2 |
| CD127 (IL-7RA) | NM_002185.2 | Irf7 | NM_001572.3 |
| CD14 | NM_000591.2 | Irf8 | NM_002163.2 |
| CD155 | NM_006505.3 | Itga1 (CD49) | NM_181501.1 |
| CD160 | NM_007053.2 | Itga2 (CD49b) | NM_002203.2 |

*Fig. 11*

| Gene Id | Target Transcript NCBI Accession # | Gene Id | Target Transcript NCBI Accession # |
|---|---|---|---|
| CD163 | NM_004244.4 | Itgae (CD103) | NM_002208.4 |
| CD167 DDR1 | NM_001954.4 | Itgax | NM_000887.3 |
| CD2 | NM_001767.2 | Itk | NM_005546.3 |
| CD200 | NM_005944.5 | Itm2a | NM_004867.4 |
| CD200R1 | NM_138939.2 | Jak3 | NM_000215.2 |
| CD207-CLEC4K LangERIN | NM_015717.2 | Jakmip1 | NM_001099433.1 |
| CD209 | NM_021155.2 | KIR2DL1 | NM_014218.2 |
| CD22 (Siglec-2) | NM_001771.2 | KLK6 | NM_002774.3 |
| CD226 | NM_006566.2 | KLRG2 (CLEC15b) | NM_198508.2 |
| CD244 | NM_016382.2 | Klrc1 (NKG2A) | NM_002259.3 |
| CD24A | NM_013230.2 | Klrc2 (NKG2c) | NM_002260.3 |
| CD28 | NM_001243078.1 | Klrd1 (CD94) | NM_002262.3 |
| CD3 delta | NM_000732.4 | Klrk1-NKG2D | NM_007360.1 |
| CD3 epsilon | NM_000733.2 | LAIR1 | NM_002287.3 |
| CD3 zeta (CD247) | NM_198053.1 | LIFR | NM_002310.3 |
| CD300a | NM_007261.2 | LILRA1 (CD851) | NM_006863.1 |
| CD300b (CD300LB) IREM3) | NM_174892.2 | LILRA2 v1-2 (CD85H) | NM_001130917.1 |
| CD300e (IREM2) | NM_181449.1 | LILRA4 (CD85G) | NM_012276.3 |
| CD300f (IREM1) | NM_139018.3 | LILRA5 v3-4 (CD85F) | NM_181879.1 |
| CD317 (Bst2) | NM_004335.2 | Lag3 (CD223) | NM_002286.5 |
| CD33 | NM_001177608.1 | Lamp2 | NM_002294.2 |
| CD4 | NM_000616.3 | Lat | NM_001014987.1 |
| CD40 (TNFRSF5) | NM_001250.4 | Lat2-linker for activation of T cells family member 2 | NM_014146.3 |

*Fig. 11*
*(cont.)*

| Gene Id | Target Transcript NCBI Accession # | Gene Id | Target Transcript NCBI Accession # |
|---|---|---|---|
| CD44 | NM_001001392.1 | Lck | NM_005356.2 |
| CD45 (PTPRC) | NM_080921.2 | Lgals3 | NM_001177388.1 |
| CD47 | NM_001777.3 | Lgals3BP | NM_005567.3 |
| CD48 | NM_001778.2 | Lgals9-lectin | NM_002308.3 |
| CD5 | NM_014207.2 | Li1RB4 | NM_001081438.1 |
| CD55 | NM_000574.3 | Lst1 | NM_001166538.1 |
| CD62L L-selectiN Sell | NR_029467.1 | Ltk | NM_002344.5 |
| CD68 (SCARD1) | NM_001251.2 | Ly6e | NM_002346.2 |
| CD69 | NM_001781.1 | Ly6g6c | NM_025261.2 |
| CD7 | NM_006137.6 | Ly6g6d | NM_021246.2 |
| CD72 | NM_001782.2 | MAGEA1-melanoma antigen family A | NM_004988.4 |
| CD79A | NM_001783.3 | MBL2 | NM_000242.2 |
| CD80 | NM_005191.3 | MER (MERTK) | NM_006343.2 |
| CD84 | NM_001184879.1 | MLANA (Mart1) | NM_005511.1 |
| CD86 | NM_175862.3 | MON1B | NM_014940.2 |
| CD8b | NM_172099.2 | MSA41 (CD20) | NM_152866.2 |
| CD90 (Thy1) | NM_006288.2 | Maf | NM_001031804.2 |
| CD96 | NM_005816.4 | Mafb | NM_005461.3 |
| CDH1 (E Cadherin) | NM_004360.2 | Marco (Scara2) | NM_006770.3 |
| CLEC12A | NM_138337.5 | Mica | NM_000247.1 |
| CLEC15a (KLRG1 MAFA) | NM_005810.3 | Micb | NM_005931.3 |
| CLEC4A | NM_194448.2 | Mn1 | NM_002430.2 |
| CLEC6A | NM_001007033.1 | Mrc1 | NM_002438.2 |

Fig. 11
(cont.)

| Gene Id | Target Transcript NCBI Accession # | Gene Id | Target Transcript NCBI Accession # |
|---|---|---|---|
| CSPG4 | NM_001897.4 | Myh4 | NM_017533.2 |
| CXCL11-ITAC | NM_005409.3 | NCR2-NKp44 | NM_004828.3 |
| CXCL2 (GRO-beta MIP-2) | NM_002089.3 | nFATC1 | NM_172389.1 |
| CXCL9-Mig | NM_002416.1 | Nkg7 | NM_005601.3 |
| CXCR2 | NM_001557.2 | Nlrp10 (NOD) | NM_176821.3 |
| Caspase 3 | NM_032991.2 | Nr4a2 | NM_006186.3 |
| Ccl19 | NM_006274.2 | Ny-eso-1 (CTAG1B) | NM_001327.2 |
| Ccl21 | NM_002989.2 | OAZ1 | NM_004152.2 |
| Ccl24 | NM_002991.2 | OSCAR | NM_130771.3 |
| Ccl27 | NM_006664.2 | PARK7 | NM_001123377.1 |
| Ccl13 | NM_002983.2 | PD-1 (Pdcd1) | NM_005018.1 |
| Ccl14 | NM_002984.2 | PDCD4 | NM_014456.3 |
| Ccl15 | NM_002985.2 | POLR1B | NM_019014.3 |
| Ccl18 | NM_005623.2 | POLR2A | NM_000937.2 |
| Ccr2 | NM_001123041.2 | PPARG | NM_015869.3 |
| Ccr3 | NM_001837.2 | PPIA | NM_021130.2 |
| Ccr4 | NM_005508.4 | Pdcd1Lg1 (PD-L1) | NM_014143.2 |
| Ccr5 | NM_000579.1 | Pdcd1Lg2 (PD-L2) | NM_025239.2 |
| Ccr6 | NM_031409.2 | Pdgfra | NM_006206.3 |
| Ccr7 | NM_001838.2 | Phactr2 | NM_001100164.1 |
| Cdo1 | NM_001891.2 | Pi3kCA | NM_006218.2 |
| Chi3l1 | NM_001276.2 | Pi3kCB | NM_006219.1 |
| Chi3l2 | NM_004000.2 | Pi3kCD | NM_005026.3 |
| Ciita | NM_000246.3 | Pi3lCG | NM_002649.2 |
| Clca1 | NM_001285.3 | Pilra (FDF03 inhibited) | NM_178273.1 |

*Fig. 11*
*(cont.)*

| Gene Id | Target Transcript NCBI Accession # | Gene Id | Target Transcript NCBI Accession # |
|---|---|---|---|
| Clca2 | NM_006536.5 | Pilrb (FDF03 activated) | NM_178238.1 |
| Clec10a (mouse also MGL1) | NM_182906.2 | Postn | NM_001135935.1 |
| Clec1b (Clec-2) | NM_016509.3 | Ppplr2 | NM_006241.4 |
| Clec2d (OCIL) | NM_001004419.3 | Prf1 | NM_005041.3 |
| Clec3b | NM_003278.2 | Psmb10 | NM_002801.2 |
| Clec4d (MCL) | NM_080387.4 | Psmb8 | NM_004159.4 |
| Clec4e (Mincle) | NM_014358.2 | Psmb9 | NM_002800.4 |
| Clec4a (MDL-1) | NM_013252.2 | Psme1 | NM_006263.2 |
| Clec7a (dectin-1) | NM_197954.2 | Psme2 | NM_002818.2 |
| Clec9a | NM_207345.2 | Pstpip1 | NM_003978.3 |
| Cmkrlr1 | NM_004072.1 | Pstpip2 | NM_024430.3 |
| Cpd | NM_001304.4 | Pten | NM_000314.3 |
| Crtam | NM_019604.2 | Ptger2 | NM_000956.2 |
| Csflr | NM_005211.2 | Ptger4 | NM_000958.2 |
| Csf2rb | NM_000385.2 | Ptpn10 (Dusp1) | NM_004417.2 |
| Cst6 | NM_001323.3 | Ptpn13 | NM_080684.2 |
| Cst7 | NM_003650.3 | Ptpn22 | NM_015967.3 |
| Ctla4 | NM_005214.3 | Ptpn3 | NM_002831.5 |
| Ctsb | NM_000100.2 | Ptpn6 | NM_002831.5 |
| Ctsg | NM_001911.2 | Ptpn7 | NM_002832.3 |
| Ctsz | NM_001336.3 | Ptprcap | NM_005608.2 |
| Cx3cl1 | NM_002996.3 | Ptprf | NM_002840.3 |
| Cx3cr1 | NM_001337.3 | Pvrig | NM_024070.3 |
| Cxcl1 (GRO-alpha) | NM_001511.1 | RGS16 | NM_002928.2 |

*Fig. 11*
*(cont.)*

| Gene Id | Target Transcript NCBI Accession # | Gene Id | Target Transcript NCBI Accession # |
|---|---|---|---|
| Cxcl10 (IP-10) | NM_001565.1 | RIKEN cDNA 4632428N05 (VISTA) | NM_022153.1 |
| Cxcl13 (BCA-1) | NM_006419.2 | RPL19 | NM_000981.3 |
| Cxcl14 | NM_004887.4 | Rarres2 | NM_002889.3 |
| Cxcl3 | NM_002090.2 | Rctnlb (Rclmb Fizz2) | NM_032579.2 |
| Cxvl4 (Pf4) | NM_002619.2 | Rgn | NM_152869.2 |
| Cxcr3 | NM_001504.1 | Rora | NM_134261.2 |
| Cxcr6 | NM_006564.1 | Rorc (RORg and T) | NM_001001523.1 |
| Cxcr6 | NM_020311.1 | Runx1 | NM_001754.4 |
| DCK | NM_000788.2 | Runx3 | NM_004350.1 |
| DCT | NM_001922.3 | S100a8 | NM_002964.3 |
| Dab1 | NM_021080.3 | S100a9 | NM_002965.2 |
| Dap10 (HCST) | NM_001007469.1 | SAMD3 | NM_0010177373.2 |
| Dap12 (TYROBP) | NM_003332.2 | SART3 | NM_014706.3 |
| Def6 | NM_022047.3 | SDHA | NM_004168.1 |
| Defb1 | NM_005218.3 | SIGLEC14 | NM_001098612.1 |
| Defb2 | NM_004942.2 | SIGLEC15 (CD33L3) | NM_213602.2 |
| Dgkz | NM_001105540.1 | SIGLEC5 (CD170; CD33L2) | NM_003830.2 |
| Dpp4 (CD26) | NM_001935.3 | Samhd1 | NM_015474.2 |
| Dsc1 | NM_024421.2 | Sema4a | NM_001193300.1 |
| Dsc2 | NM_024422.3 | Serpinf1 | NM_002615.4 |
| Dsg2 | NM_001943.3 | Sgpp2 | NM_152386.2 |
| EEF1G | NM_001404.4 | Sh2d1b | NM_053282.4 |
| EGF | NM_001963.3 | Sh2d2a | NM_001161443.1 |

*Fig. 11*
*(cont.)*

| Gene Id | Target Transcript NCBI Accession # | Gene Id | Target Transcript NCBI Accession # |
|---|---|---|---|
| Efcmp1 | NM_004105.3 | Sirpb1 | NM_006065.3 |
| Egfr | NM_211282.1 | Sirpg | NM_001039508.1 |
| Egr2 | NM_000399.3 | Sit1 | NM_014450.2 |
| Eomes | NM_005442.2 | Sla1 | NM_001045556.2 |
| Epcam | NM_002354.1 | Sla2 | NM_032214.2 |
| Ezr | NM_003378.4 | Slamf1 (CD150 Slam) | NM_003037.2 |
| F2R (PAR-1) | NM_001992.2 | Slamf6 (ntba) | NM_001184714.1 |
| F2RL1 (PAR-2) | NM_005242.3 | Slamf7 (Cracc) | NM_021181.3 |
| FCER1A | NM_002001.2 | Socs3 | NM_003955.3 |
| FCGR2A (CD32) | NM_021642.2 | Stat1 | NM_007315.2 |
| FN1 | NM_212482.1 | Stat6 | NM_003153.3 |
| Fap | NM_004460.2 | TBP | NM_001172085.1 |
| Fasl (TNFSF6) | NM_000639.1 | TIMP3 | NM_000362.4 |
| Fcgr2b (CD32b) | NM_001002273.1 | TIMP4 | NM_003256.2 |
| Fcrl3 | NM_052939.3 | TNFRSF10b-TRAIL R2 DR5 | NM_003842.3 |
| Folr4 | NM_001199206.1 | TNFRSF13B-TAC1 | NM_012452.2 |
| Foxp3 | NM_014009.3 | TNFRSF8-CD30 | NM_152942.2 |
| G6PD | NM_000402.2 | TNFSF10-TRAIL CD253 | NM_003810.2 |
| GAPDH | NM_000181.1 | TNFSF13B-BLYS | NM_006573.4 |
| GUSB | NM_000181.1 | TNFSF8-CD30L | NM_001244.2 |
| Gas6 | NM_000820.2 | TREM1 | NM_018643.3 |
| Gata3 | NM_001002295.1 | TREM2 | NM_018965.2 |
| Gdf10 | NM_004962.2 | TREML1 (TLT-1) | NM_178174.2 |

*Fig. 11*
*(cont.)*

| Gene Id | Target Transcript NCBI Accession # | Gene Id | Target Transcript NCBI Accession # |
|---|---|---|---|
| Gfi1 | NM_005263.2 | TREML2 (TLT-2) | NM_024807.2 |
| Gitr (Tnfrsf18) | NM_004195.2 | TUBB | NM_178014.2 |
| Gitrl (Tnfsf18) | NM_005092.2 | TYR (Tyrosinase) | NM_000372.4 |
| Gnly | NM_006433.2 | TYRO3 | NM_006293.2 |
| Gpld1 | NM_001503.2 | Tagap | NM_054114.3 |
| gpr18 | NM_001098200.1 | Tarp (TCR gamma alternate reading frame protein) | NM_001003799.1 |
| Grap2 | NM_004810.2 | Tbx21 (Tbet) | NM_013351.1 |
| Gzma | NM_006144.2 | Tcn2 | NM_000355.2 |
| Gzmb | NM_004131.3 | Tigit | NM_173799.2 |
| Gzmk | NM_002104.2 | Tmem2 | NM_013390.2 |
| HLA-A (HLA Class I) | NM_002116.5 | Tnfa | NM_000594.2 |
| HLA-B | NM_005514.6 | Tnfaip3 | NM_006290.2 |
| HLA-C | NM-002117.4 | Tnfaip6 | NM_007115.2 |
| HLA-DRA (HLA class II) | NM_019111.3 | Tnfaip8L2 | NM_024575.3 |
| HLA-E | NM_005516.4 | Tnfrsf14 (Hvem) | NM_003820.2 |
| HPRT1 | NM_000194.1 | Tnfrsf4 (Ox40) | NM_003327.2 |
| Havcr1-Tim1 | NM_001099414.1 | Tnfrsf7 (Cd27) | NM_001242.4 |
| Havcr2-Tim3 | NM_032782.3 | Tnfrsf9 (CD137 4-1BB) | NM_001561.4 |
| Hcls1 | NM_005335.4 | Tnfsf14 (LIGHT) | NM_003807.2 |
| Hgfac | NM_001528.2 | Tnfsf4 | NM_003326.2 |
| Hif1a | NM_001530.2 | Tnfsf7 CD27L | NM_001252.2 |

*Fig. 11*
*(cont.)*

| Gene Id | Target Transcript NCBI Accession # | Gene Id | Target Transcript NCBI Accession # |
| --- | --- | --- | --- |
| Hopx | NM_001145460.1 | Tnfsf9 (4-1BBL) | NM_003811.3 |
| IFNg | NM_000619.2 | Tox | NM_014729.2 |
| IGSF6 | NM_005849.2 | Trat1 | NM_016388.2 |
| IL-10R1 | NM_001558.2 | UBB | NM_018955.2 |
| IL-2RA | NM_000417.1 | Ubash3a | NM_001001895.1 |
| IL-2RB | NM_000878.2 | Ubash3b | NM_032873.3 |
| IL-2Rg | NM_000206.1 | VCAM | NM_001078.3 |
| IL-37 | NM_014439.3 | Xist | NM_001564.1 |
| IL-10 | NM_000572.2 | Zap70 | NM_001079.3 |
| IL-18 | NM_001562.2 | Zbtb16 | NM_006006.4 |
| IL18R1 | NM_003855.2 | Zbtb32 | NM_014383.1 |

*Fig. 11*
(cont.)

SEQUENCE LISTING

```
<160> NUMBER OF SEQ ID NOS: 11

<210> SEQ ID NO 1
<211> LENGTH: 447
<212> TYPE: PRT
<213> ORGANISM: Artificial Sequence
<220> FEATURE:
<223> OTHER INFORMATION: monoclonal antibody heavy chain sequence

<400> SEQUENCE: 1

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

-continued

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 2
<211> LENGTH: 218
<212> TYPE: PRT
<213> ORGANISM: Artificial Sequence
<220> FEATURE:
<223> OTHER INFORMATION: monoclonal antibody light chain sequence

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
            145                 150                 155                 160

Gly Asn Ser Gln Glu Ser Val Thr Glu Gln Asp Ser Lys Asp Ser Thr
        165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 3
<211> LENGTH: 120
<212> TYPE: PRT
<213> ORGANISM: Artificial Sequence
<220> FEATURE:
<223> OTHER INFORMATION: monoclonal antibody heavy chain variable domain

<400> SEQUENCE: 3

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
            85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

<210> SEQ ID NO 4
<211> LENGTH: 111
<212> TYPE: PRT
<213> ORGANISM: Artificial Sequence
<220> FEATURE:
<223> OTHER INFORMATION: monoclonal antibody light chain variable domain

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys
            100                 105                 110
```

<210> SEQ ID NO 5
<211> LENGTH: 5
<212> TYPE: PRT
<213> ORGANISM: Artificial Sequence
<220> FEATURE:
<223> OTHER INFORMATION: monoclonal antibody heavy chain
      complementarity-determining region 1

<400> SEQUENCE: 5

Asn Tyr Tyr Met Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: monoclonal antibody heavy chain
      complementarity-determining region 2

<400> SEQUENCE: 6

Gly Ile Asn Pro Ser Asn Gly Gly Thr Asn Phe Asn
1               5                   10

<210> SEQ ID NO 7
<211> LENGTH: 11
<212> TYPE: PRT
<213> ORGANISM: Artificial Sequence
<220> FEATURE:
<223> OTHER INFORMATION: monoclonal antibody heavy chain
      complementarity-determining region 3

<400> SEQUENCE: 7

Arg Asp Tyr Arg Phe Asp Met Gly Phe Asp Tyr
1               5                   10

<210> SEQ ID NO 8
<211> LENGTH: 15
<212> TYPE: PRT
<213> ORGANISM: Artificial Sequence
<220> FEATURE:
<223> OTHER INFORMATION: monoclonal antibody light chain
      complementarity-determining region 1

<400> SEQUENCE: 8

Arg Ala Ser Lys Gly Val Ser Thr Ser Gly Tyr Ser Tyr Leu His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: monoclonal antibody light chain
      complementarity-determining region 2

<400> SEQUENCE: 9

Leu Ala Ser Tyr Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: monoclonal antibody light chain
      complementarity-determining region 3

<400> SEQUENCE: 10

Gln His Ser Arg Asp Leu Pro Leu Thr
1               5

<210> SEQ ID NO 11
<211> LENGTH: 290
<212> TYPE: PRT
<213> ORGANISM: Homo sapiens

<400> SEQUENCE: 11

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

BIOMARKERS FOR CANCER THERAPEUTICS

RELATED APPLICATIONS

This application is a 35 U.S.C. § 371 filing of International Patent Application No. PCT/US2018/029915, filed Apr. 27, 2018, which claims the benefit of priority of U.S. Provisional Patent Application No. 62/491,746, filed Apr. 28, 2017. The contents of the aforementioned applications are hereby incorporated by reference in their entirety for all purposes.

FIELD OF THE INVENTION

The present invention relates to the field of cancer therapeutics. In particular, the present invention relates to biomarkers useful for identifying a variety of cancers that can be treated with a combination therapy comprising pembrolizumab, a pembrolizumab variant and/or an antigen-binding fragment thereof and talimogene laherparepvec.

BACKGROUND

Treatment with anti-PD-1 or anti-PD-L1 antibodies results in long lasting anti-tumor responses in patients with a variety of cancers, and it is becoming standard of care treatment for patients with metastatic melanoma, carcinomas of the head and neck, lung, kidney and bladder, as well as Merkel cell carcinoma and Hodgkin's disease (Sharma, P., and Allison, J. P. (2015). The future of immune checkpoint therapy, Science 348, 56-61). However, in all of these indications, only a subset of patients respond to therapy, with a majority of patients being primarily resistant to PD-1 blockade. Accordingly, new cancer treatments targeting PD-1 blockade-resistant cancers are needed.

SUMMARY

The present disclosure is based on the discovery of biomarkers intratumoral biomarkers) that can be used to identify a tumor that is responsive to combination therapy with pembrolizumab, a pembrolizumab variant or an antigen-binding fragment thereof and talimogene laherparepvec. The present invention is particularly useful for treating tumors in subjects that were previously untreatable or not sufficiently treatable with monotherapy (i.e., with a checkpoint inhibitor (e.g., with anti-PD-L1 therapy or anti-PD-1 therapy (e.g., pembrolizumab, a pembrolizumab variant or an antigen-binding fragment thereof)). Intratumoral administration of the oncolytic virus talimogene laherparepvec (a herpes simplex virus type 1 designed to preferentially replicate in tumors and produce granulocyte-macrophage colony-stimulating factor (GM-CSF)) was determined to increase intratumoral infiltration by cytotoxic T-cells in human patients, thereby improving the anti-tumor activity of the anti-PD-1 antibody pembrolizumab when used as a combination therapy in subjects with tumors that exhibit a low CD8+ T-cell density, a low or negative interferon gamma signature, and/or a low or negative PD-L1 status, and/or in subjects that were non-responsive or poorly responsive to previous checkpoint inhibitor therapy (e.g., with anti-PD-L1 therapy or anti-PD-1 therapy (e.g., pembrolizumab), or are unlikely to respond to monotherapy with a checkpoint inhibitor (e.g., with anti-PD-L1 therapy or anti-PD-1 therapy pembrolizumab, a pembrolizumab variant or an antigen-binding fragment thereof)) due to, e.g., low PD-L1 status.

In one aspect, a method of treating a tumor in a subject comprising selecting a subject having a tumor comprising a CD8+ T-cell infiltration density of fewer than about 1500, about 1400, about 1300, about 1200, about 1100, about 1000, about 900, about 800, about 700, about 600, or about 500 cells/mm$^2$, administering talimogene laherparepvec to the subject, and administering pembrolizumab, a pembrolizumab variant or an antigen-binding fragment thereof, to the subject is provided.

In certain embodiments, the tumor expresses lower levels of two, three, four or five interferon gamma (IFNγ) signature genes prior to administering compared to a pre-specified threshold of a control panel of signature genes selected from the group consisting of IFNγ, signal transducer and activator of transcription 1 (STAID, C-C chemokine receptor type 5 (CCR5), chemokine (C-X-C motif) ligand 9 (CXCL9), perform 1 (PRF1), HLA-DRA, chemokine (C-X-C motif) ligand 10 (CXCL10), chemokine (C-X-C motif) ligand 11 (CXCL11), indoleamine 2,3-dioxygenase 1 (IDO1) and granzyme A (GZMA). In certain embodiments, the tumor expresses no IFNγ signature genes prior to administering the talimogene laherparepvec and the pembrolizumab, the pembrolizumab variant or the antigen-binding fragment thereof.

In certain embodiments, the tumor has a programmed death-ligand 1 (PD-L1) status of less than about 50% prior to administering the talimogene laherparepvec and the pembrolizumab, the pembrolizumab variant or the antigen-binding fragment thereof. In certain embodiments, the tumor has a PD-L1 status of less than about 1% prior to administering the talimogene laherparepvec and the pembrolizumab, the pembrolizumab variant or the antigen-binding fragment thereof.

In certain embodiments, the talimogene laherparepvec, is administered to the subject intratumorally and/or the pembrolizumab or the antigen-binding fragment thereof is administered to the subject systemically.

In certain embodiments, the talimogene laherparepvec is administered to the subject prior to the administration of the pembrolizumab or the antigen-binding fragment thereof.

In certain embodiments, a reduction in size of the injected tumor and/or a reduction in size of a non-injected tumor occur after administering the talimogene laherparepvec and the pembrolizumab, the pembrolizumab variant or the antigen-binding fragment thereof.

In certain embodiments, CD8+ T-cell infiltration density is increased in the tumor after administering the talimogene laherparepvec. In certain embodiments, dividing CD8$^+$ T-cells circulating in the subject are increased after administering the talimogene laherparepvec and the pembrolizumab, the pembrolizumab variant or the antigen-binding fragment thereof.

In certain embodiments, the subject has a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the melanoma is cutaneous melanoma, metastatic melanoma, or uveal melanoma, the breast cancer is HER2+ breast cancer, HER2– HR+ breast cancer, or triple-negative breast cancer, the prostate cancer is castration-resistant prostate cancer, the bladder cancer is transitional cell cancer or urothelial cancer, the head and neck cancer is recurrent or metastatic squamous cell carcinoma of the head and neck, and/or the sarcoma is soft tissue sarcoma or bone sarcoma.

In certain embodiments, the tumor comprises a CD8$^+$ T-cell infiltration density of fewer than about 1000 cells/mm$^2$.

In one aspect, a method of treating a tumor in a subject that is poorly responsive to or non-responsive to monotherapy with a checkpoint inhibitor with anti-PD-L1 therapy or anti-PD-1 therapy (e.g., pembrolizumab, a pembrolizumab variant or an antigen-binding fragment thereof)) comprising administering talimogene laherparepvec to the subject, and administering pembrolizumab, a pembrolizumab variant or an antigen-binding fragment thereof to the subject is provided.

In certain embodiments, the tumor comprises a CD8$^+$ T-cell infiltration density of fewer than about 1500, about 1400, about 1300, about 1200, about 1100, about 1000, about 900, about 800, about 700, about 600, or about 500 cells/mm$^2$ prior to administering, the tumor expresses lower levels of two three, four or five interferon gamma (IFNγ) signature genes prior to administering than a pre-specified threshold of a control panel of signature genes selected from the group consisting of IFNγ, STAT1, CCR5, CXCL9, PRF1, HLA-DRA, CXCL10, CXCL11, IDO1 and GZMA, and/or the tumor has a PD-L1 status of less than about 50% prior to administering the talimogene laherparepvec, and the pembrolizumab, the pembrolizumab variant or the antigen-binding fragment thereof.

In one aspect, a method of treating a tumor in a subject that progressed during monotherapy with a checkpoint inhibitor (e.g., with anti-PD-L1 therapy or anti-PD-1 therapy (e.g., pembrolizurnah, a pembrolizumab variant or an antigen-binding fragment thereof)), comprising administering talimogene laherparepvec to the subject, and administering pembrolizumab, a pembrolizumab variant or an antigen-binding fragment thereof to the subject is provided.

In certain embodiments, the tumor comprises a CD8$^+$ T-cell infiltration density of fewer than about 1500, about 1400, about 1300, about 1200, about 1100, about 1000, about 900, about 800, about 700, about 600, or about 500 cells/mm$^2$ prior to administering, the tumor expresses lower levels of two, three, four or five IFNγ (signature genes prior to administering than a pre-specified threshold of a control panel of signature genes selected from the group consisting of IFNγ, STAT1, CCR5, CXCL9, PRF1, HLA-DRA, CXCL10, CXCL11, IDO1 and GZMA, and/or the tumor has a PD-L1 status of less than about 50% prior to administering the talimogene laherparepvec and the pembrolizumab, the pembrolizumab variant or the antigen-binding fragment thereof.

In certain embodiments, the talimogene laherparepvec is administered sequentially as an initial dose followed by one or more secondary doses. In certain embodiments the pembrolizumab, the pembrolizumab variant or the antigen-binding fragment thereof is administered sequentially as an initial dose followed by one or more secondary doses. In certain embodiments, the talimogene laherparepvec is administered sequentially as an initial dose followed by one or more secondary doses, and the pembrolizumab, the pembrolizumab variant or the antigen-binding fragment thereof is administered sequentially and concomitantly with the one or more secondary doses of the talimogene laherparepvec.

In certain embodiments, the talimogene laherparepvec is administered intratumorally and wherein the pembrolizumab, the pembrolizumab variant or the antigen-binding fragment thereof is administered systemically. In certain embodiments, the talimogene laherparepvec and the pembrolizumab, the pembrolizumab variant or the antigen-binding fragment thereof, are administered intratumorally.

In one aspect, a method of treating a tumor having a CD8$^+$ T-cell infiltration density of fewer than about 1500, about 1400, about 1300, about 1200, about 1100, about 1000, about 900, about 800, about 700, about 600, or about 500 cells/mm$^2$ comprising contacting the tumor with talimogene laherparepvec and pembrolizumab, a pembrolizumab variant or an antigen-binding fragment thereof is provided.

In certain embodiments, the tumor is from a subject having a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the cancer is cutaneous melanoma. In certain embodiments, the cancer is recurrent or metastatic squamous cell carcinoma of the head and neck.

In certain embodiments, the tumor expresses lower levels of two, three, four or five IFNγ signature genes prior to contacting than a pre-specified threshold of a control panel of signature genes selected from the group consisting of IFNγ, STAT1, CCR5, CXCL9, PRF1, HLA-DRA, CXCL10, CXCL11, IDO1 and GZMA.

In certain embodiments, the tumor has a PD-L1 of less than about 50% prior to contacting with the talimogene laherparepvec and the pembrolizumab, the pembrolizumab variant or the antigen-binding fragment thereof.

In one aspect, a method of treating a tumor expressing lower levels of two, three, four or five IFNγ signature genes prior to treatment than a pre-specified threshold of a control panel of signature genes elected from the group consisting of IFNγ, STAT1, CCR5, CXCL9, PRF1, HLA-DRA, CXCL10, CXCL11, IDO1 and GZMA, comprising contacting the tumor with talimogene laherparepvec and pembrolizumab, a pembrolizumab variant or an antigen-binding fragment thereof is provided.

In certain embodiments, the tumor is from a subject having a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the cancer is melanoma (e.g., cutaneous melanoma). In certain embodiments, the cancer is head and neck cancer (e.g., recurrent or metastatic squamous cell carcinoma of the head and neck).

In certain embodiments, the tumor has a CD8$^+$ T-cell infiltration density of fewer than about 1500, about 1400, about 1300, about 1200, about 1100, about 1000, about 900, about 800, about 700, about 600, or about 500 cells/mm$^2$ prior to contacting.

In certain embodiments, the tumor has a PD-L1 status of less than about 50% prior to contacting with the talimogene laherparepvec and the pembrolizumab, a pembrolizumab variant or an antigen-binding fragment thereof.

In one aspect, a method of treating a tumor having a PD-L1 status of less than about 50% prior to treatment, comprising contacting the tumor with talimogene laherparepvec and pembrolizumab a pembrolizumab variant or an antigen-binding fragment thereof is provided.

In certain embodiments, the tumor is from a subject having a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the cancer is melanoma (e.g., cutaneous melanoma). In certain embodiments, the cancer is head and neck cancer (e.g., recurrent or metastatic squamous cell carcinoma of the head and neck).

In certain embodiments, the tumor has a CD8+ T-cell infiltration density of fewer than about 1500, about 1400, about 1300, about 1200, about 1100, about 1000, about 900, about 800, about 700, about 600, or about 500 cells/mm$^2$ prior to contacting.

In certain embodiments, the tumor expresses lower levels of two, three, four or five IFNγ signature genes prior to contacting than a pre-specified threshold of a control panel of signature genes selected from the group consisting of IFNγ, STAT1, CCR5CXCL9, PRF1, HLA-DRA, CXCL10, CXCL11, IDO1 and GZMA.

In one aspect, a method of treating a tumor having a CD8+ T-cell infiltration density of fewer than about 1500, about 1400, about 1300, about 1200, about 1100, about 1000, about 900, about 800, about 700, about 600, or about 500 cells/mm$^2$ and expressing lower levels of five or fewer IFNγ signature genes prior to treatment than a pre-specified threshold of a control panel of signature genes selected from the group consisting of IFNγ, STAT1, CCR5, CXCL9, PRF1, HLA-DRA, CXCL10, CXCL11, IDO1 and GZMA, comprising contacting the tumor with talimogene laherparepvec and pembrolizumab, a pembrolizumab variant or an-antigen-binding fragment thereof is provided.

In certain embodiments, the tumor is from a subject having a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the cancer is melanoma (e.g., cutaneous melanoma). In certain embodiments, the cancer is head and neck cancer (e.g., recurrent or metastatic squamous cell carcinoma of the head and neck).

In certain embodiments, the tumor has a PD-L1 status of less than about 50% prior to contacting with the talimogene laherparepvec and the pembrolizumab, a pembrolizumab variant or an antigen-binding fragment thereof.

In one aspect, a method of treating a previously pembrolizumab-, pembrolizumab variant- or antigen-binding fragment thereof-resistant tumor in a subject subsequently exposed to talimogene laherparepvec comprising administering to the subject pembrolizumab, a pembrolizumab variant or an antigen-binding fragment thereof is provided.

In certain embodiments, the subject has a cancer selected from the group consisting of melanoma, non-small cell lung cancer, head and neck cancer, colorectal cancer, breast cancer, ovarian cancer, bladder cancer, prostate cancer, sarcoma, renal cell cancer, gastric cancer, esophageal cancer, anal canal cancer, biliary tract cancer and pancreatic cancer. In certain embodiments, the cancer is melanoma (e.g., cutaneous melanoma). In certain embodiments, the cancer is head and neck cancer (e.g., recurrent or metastatic squamous cell carcinoma of the head and neck).

In one aspect, a method of rendering a tumor that is resistant to monotherapy with a checkpoint inhibitor (e.g., with anti-PD-L1 therapy or anti-PD-1 therapy (e.g., pembrolizumab, a pembrolizumab variant or an antigen-binding fragment thereof)) in a subject sensitive to pembrolizumab, a pembrolizumab variant or an antigen-binding fragment thereof, comprising contacting the tumor with talimogene laherparepvec is provided.

In certain embodiments, a sample of the tumor taken from the subject after contacting the tumor with talimogene laherparepvec has an increased level of one or any combination of CD8+CD4+ T-cells, IFNγ, CD20+ B-cells, memory T-cells, regulatory T-cells and CD56+ cells relative to a sample of the tumor taken prior to the contacting the tumor with talimogene laherparepvec.

In certain embodiments, the tumor has a CD8+ T-cell infiltration density of greater than 1000 cells/mm$^2$ after contacting with talimogene laherparepvec.

In certain embodiments, a blood sample taken from the subject after contacting the tumor with talimogene laherparepvec has an increased level of CD8+ T-cells and/or CD4+ T-cells compared to a blood sample taken from the subject prior to the contacting, optionally wherein the CD8+ T-cells are dividing CD8+ T-cells.

In one aspect, a method of treating a tumor in a subject comprising selecting a subject having a tumor comprising a CD8+ T-cell infiltration density of fewer than about 1500, about 1400, about 1300, about 1200, about 1100, about 1000, about 900, about 800, about 700, about 600, or about 500 cells/mm$^2$, administering talimogene laherparepvec to the subject intratumorally as an initial dose followed by one or more secondary doses, and administering pembrolizumab, a pembrolizumab variant or an antigen-binding fragment thereof to the subject systemically as an initial dose followed by one or more secondary doses is provided.

In certain embodiments, the secondary doses are administered every two weeks (Q2W). In certain embodiments, the initial dose of talimogene laherparepvec is administered on day 1 of week 1 and a secondary dose of talimogene laherparepvec is administered on day 1 of week 4, on day 1 of week 6, and Q2W thereafter. In certain embodiments, the initial dose of pembrolizumab, pembrolizumab variant or antigen-binding fragment thereof is administered on day 1 of week 6 and a secondary dose of pembrolizumab, pembrolizumab variant or antigen-binding fragment thereof is administered on day 1 of week 8 and Q2W thereafter.

In certain embodiments, the initial dose of talimogene laherparepvec is administered at a dose of $10^6$ plaque forming units (pfu)/mL, and the secondary doses of talimogene laherparepvec are administered at a dose of $10^8$ pfu/mL.

In certain embodiments, the initial dose of pembrolizumab, pembrolizumab variant or antigen-binding fragment thereof is administered at a dose of 200 mg and the secondary doses of pembrolizumab, pembrolizumab variant or antigen-binding fragment thereof are administered at a dose of 200 mg.

The summary of the disclosure described above is non-limiting and other features and advantages of the disclosed biomarkers and methods will be apparent from the following drawings, detailed description of the disclosure, and claims.

BRIEF DESCRIPTION OF THE DRAWINGS

FIG. 11 depicts an IFN-γ gene signature panel according to certain embodiments of the invention.

DETAILED DESCRIPTION OF EXEMPLARY EMBODIMENTS

Figure 1A:
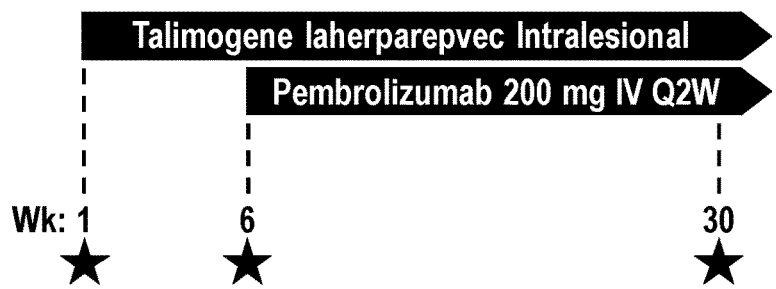
FIG. 1 depicts a melanoma study design and clinical response to a combination of talimogene laherparepvec and pembrolizumab. (A) Sets forth the phase 1b study design schema. Stars indicate the time of scheduled tumor biopsies. (B) Depicts computer tomographic scans of two patients with response to the combination therapy. Melanoma metastases are marked with an arrow at baseline. (C) Depicts a waterfall plot of best response change in tumor burden from baseline. Patients were required to have baseline and ≥1 post-baseline tumor assessments to be included. (D) Depicts a change in tumor burden over time. (E) Depicts a Kaplan-Meier analysis of progression-free survival. (F) Depicts a Kaplan-Meier analysis of overall survival.

It has been established that a high level of CD8+ T-cell infiltration, a high level of PD-L1 and/or a positive IFNγ gene signature in a tumor are required for the successful treatment of a tumor using PD-1/PD-L1 antagonists. Indeed, current cancer therapies that target the programmed death-1 (PD-1) receptor have shown unprecedented rates of durable clinical responses in patients with various cancer types, including tumor regression after therapeutic PD-1 blockade, with such results requiring a high level of pre-existing CD8+ T-cells (Tumeh et al. (2014) Nature 515:568-571). An anti-PD-L1 antibody was determined to be efficacious in treating multiple cancer types in patients with tumors expressing high levels of PD-L1 (Herbst et al. (2014) Nature 515:563-7). In addition, the presence of a high interferon gamma (IFNγ) gene signature in a tumor correlates with the ability to treat the tumor with PD-1 antagonists (WO 2015/094992; Applicant, Merck Sharp & Dohme Corporation).

Surprisingly, and quite contrary to the accepted dogma that a high level of CD8+ T-cell infiltration, a high PD-L1 level, and/or a positive IFNγ gene signature is necessary to successfully treat a tumor with a PD-1 antagonist, it has been discovered that tumors having low levels of CD8+ T-cell infiltration, a low or negative PD-L1 status, and/or a low or negative IFNγ gene signature profile could be effectively treated with the PD-1 antagonist pembrolizumab using a combination therapy approach with talimogene laherparepvec. This discovery represents the first clinical demonstration that talimogene laherparepvec could trigger an immune response in a tumor in vivo sufficient to enable efficient targeting of the tumor by the PD-1 antagonist pembrolizumab.

It was further discovered that intratumoral administration of talimogene laherparepvec favorably altered the tumor microenvironment of injected lesions by, for example, increasing CD8+ T-cell infiltration, increasing PD-L1 expression, and/or producing a more positive IFNγ gene signature, thus rendering tumor cells more susceptible to anti-PD-1 therapy. Expression of PD-L1 increased after treatment with talimogene laherparepvec but was countered by subsequent PD-1 blockade with pembrolizumab. After injection of talimogene laherparepvec into a lesion, tumor antigen-specific CD8+ T-cells trafficked to and infiltrated both the local lesion as well as distant metastatic lesions. Using a combination therapy of pembrolizumab and talimogene laherparepvec, an anti-PD-1 blockade acted to counter checkpoint protein-mediated inhibition of the immune response.

Thus, administration of the oncolytic virus rendered "cold" tumors (i.e., tumors exhibiting a low level of immune infiltration (e.g., by CD8+ T cells), a negative IFNγ gene signature, and/or a low PD-L1 status) more susceptible to pembrolizumab blockage therapy by converting such tumors to "hot" tumors (i.e., tumors exhibiting high levels of immune infiltration (e.g., by CD8+ T cells), a positive IFNγ gene signature, and/or a high PD-L1 status). Accordingly, tumors that previously were minimally responsive to or unresponsive to monotherapy with a checkpoint inhibitor (e.g., with anti-PD-L1 therapy or anti-PD-1 therapy (e.g., pembrolizumab or a variant or antigen-binding fragment thereof)) could be rendered sensitive to therapy with pembrolizumab, or a variant or antigen-binding fragment thereof.

Accordingly, in one embodiment, the combination of pembrolizumab, pembrolizumab variant or an antigen-binding fragment thereof and talimogene laherparepvec is used to increase the magnitude of tumor specific T-cell responses as compared to pembrolizumab, a pembrolizumab variant or an antigen-binding fragment thereof alone in patients. This effect can be particularly observed with previously untreated, unresectable, stable IIIb-IV melanoma. The combination of pembrolizumab, a pembrolizumab variant or an antigen-binding fragment thereof and talimogene laherparepvec is intended to enhance the systemic anti-tumor response to tumor antigens following the lytic replication of talimogene laherparepvec in tumors. Therefore, the combination therapy can result in enhanced destruction of injected tumors as well as uninfected/distant tumors, including micro-metastatic disease, to improve the rate of overall tumor response and duration of response. In total, these effects can contribute to an improvement in overall survival, particularly when compared to monotherapy with a checkpoint inhibitor (e.g., with anti-PD-L1 therapy or anti-PD-1 therapy (e.g., pembrolizumab, a pembrolizumab variant or an antigen-binding fragment thereof)). The use of talimogene laherparepvec in combination with pembrolizumab, a pembrolizumab variant or an antigen-binding fragment thereof, is intended to enhance T-cell activation through different mechanisms, respectively augmenting dendritic cell-mediated tumor antigen presentation (Kaufman et al., Ann Surg Oncol., 17(3):718-730, 2010) following the release of tumor antigens by lytic, virus replication, enhanced through the local expression of GM-CSF, and antagonizing immune tolerance by blocking inhibitory signals mediated by an immune checkpoint inhibitor (Kapadia and Fong, J Clin Oncol., 23:8926-8928, 2005).

In certain embodiments, a cold tumor-associated cancer having CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status and/or a negative IFNγ gene signature is treated with a combination of pembrolizumab, a pembrolizumab variant or an antigen-binding fragment thereof and talimogene laherparepvec. Such tumors include, but are not limited to, melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2− (HR+), triple-negative), ovarian cancer, bladder cancer (e.g., transitional cell cancer, urothelial cancer), prostate cancer castration-resistant), sarcoma (e.g., soft tissue, bone), renal cell cancer, gastric cancer, esophageal cancer, anal canal cancer, biliary tract cancer and pancreatic cancer.

In other embodiments, a hot tumor (or a cancer associated with a hot tumor) (i.e., a cancer that is not associated with one or more of a CD8+ T-cell infiltration density of fewer than about 1500, about 1400, about 1300, about 1200, about 1100, about 1000, about 900, about 800, about 700, about 600, or about 500 cells per 1 mm² sample (or per 1 mL sample), a low or negative PD-L1 status and/or a low level of IFNγ gene signature expression) that is responsive to monotherapy with a checkpoint inhibitor (e.g., with anti-PD-L1 therapy or anti-PD-1 therapy (e.g., pembrolizumab, a pembrolizumab variant or an antigen-binding fragment thereof)) is treated with a combination of pembrolizumab, a pembrolizumab variant or an antigen-binding fragment thereof and talimogene laherparepvec. Such cancers include, but are not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck), nasopharyngeal cancer, thyroid cancer, salivary cancer, esophageal cancer), breast cancer (e.g., ER+/HER2-breast cancer, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) and mesothelioma.

DEFINITIONS

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the gene signature score for a gene signature discussed herein, or the dosage of a pembrolizumab, pembrolizumab variant and/or antigen-binding fragment thereof or talimogene laherparepvec, or the length of treatment time with a pembrolizumab, pembrolizumab variant and/or antigen-binding fragment thereof or talimogene laherparepvec) means that the parameter may vary by as much as 10% above or below the stated numerical value for that parameter. For example, a gene signature consisting of about 10 genes may have between 9 and 11 genes.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

As used herein, the term "antibody" refers to any form of antibody that exhibits the desired biological or binding activity. Thus, it is used in the broadest sense and specifically covers, but is not limited to, monoclonal antibodies (including full-length monoclonal antibodies), polyclonal antibodies, multi-specific antibodies (e.g., bispecific antibodies), humanized antibodies, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of Sequences of Proteins of Immunological Interest, Kabat, et al.; National institutes of Health, Bethesda, Md.; 5th ed.; NIH Publ. No. 91-3242 (1991); Kabat (1978) Adv. Prol. Chem. 32:1-75; Kabat, et al., (1977) J. Biol. Chem. 252: 6609-6616; Chothia et al., (1987) J Mol. Biol. 196:901-917 or Chothia et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. LCDR1, LCDR2 and LCDR3 in the light chain variable domain and HCDR1, HCDR2 and HCDR3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) J. Mol. Biol. 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen-binding fragment" refers to antigen-binding fragments of antibodies, i.e., antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments; diabodies; linear antibodies; single-chain antibody molecules, e.g., sc-Fv; nanobodies and multi-specific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g., without producing undesired results such as false positives. Antibodies, or binding fragments thereof, useful in the present invention will bind to the target protein with an affinity that is at least two fold greater, preferably at least ten times greater, more preferably at least 20 times greater, and most preferably at least 100 times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum," "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Biotherapeutic agent" means a biological molecule, such as an antibody, that blocks ligand/receptor signaling in any biological pathway that supports tumor maintenance and/or growth or suppresses the anti-tumor immune response and/or recruits CD8+ T-cell infiltration to the tumor.

The terms "cancer," "cancerous," or "malignant" refer to or describe the physiological condition in mammals that is typically characterized by unregulated cell growth. Examples of cancers associated with one or more of a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and/or a low level of IFNγ gene signature expression, include but are not limited to, carcinoma, lymphoma, leukemia, blastoma, and sarcoma.

Examples of particular cancers that are associated with one or more of a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and/or a low level of IFNγ gene signature expression, include, but are not limited to, melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2− (HR+), triple-negative), ovarian cancer, bladder cancer (e.g., transitional cell cancer, urothelial cancer), prostate cancer (e.g., castration-resistant), sarcoma (e.g., soft tissue, bone), renal cell cancer, gastric cancer, esophageal cancer, anal canal cancer, biliary tract cancer or pancreatic cancer.

Examples of particular cancers that are responsive to monotherapy with a checkpoint inhibitor (e.g., with anti-PD-L1 therapy or anti-PD-1 therapy (e.g., pembrolizumab, a pembrolizumab variant or an antigen-binding fragment thereof)), which may or may not be associated with one or more of a CD8+ infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and/or a negative IFNγ gene signature, include, but are not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g., ER+/HER2− breast cancer, triple-negative breast cancer), ovarian cancer, cervical cancer, bladder cancer urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma. In certain embodiments, a particular cancer type may have one or more subsets that are hot (i.e., that are not associated with one or more of a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and/or a negative IFNγ gene signature) and one or more subsets that are cold (i.e., are associated with one or more of a CD8+ T-cell infiltration density of fewer than 1000 cells per 1 mm$^2$ sample (or per 1 mL sample), a low or negative PD-L1 status, and/or a negative IFNγ gene signature.

Particularly preferred cancers that may be treated in accordance with the present invention include those characterized by one or any combination of: a low CD8+ T-cell density; a low or negative interferon gamma signature; and a low or negative PD-L1 status. In certain embodiments, the cancer is "cold," which refers to a cancer exhibiting a low level of immune infiltration, e.g., by CD8+ T cells that is typically not susceptible to anti-PD-1 blockage therapy by converting such tumors to "hot" tumors. In certain embodiments, a cold tumor has a CD8+ T-cell density less than or equal to about 3000, e.g., fewer than about 3000, about 2900, about 2800, about 2700, about 2600, about 2500, about 2400, about 2300, about 2200, about 2100, about 2000, about 1900, about 1800, about 1700, about 1600, about 500, about 1400, about 1300, about 1200, about 1100, about 1000, about 900, about 800, about 700, about 600, or about 500 cells per 1 $mm^2$ or 1 mL (i.e., 1 $cm^3$) sample.

As used herein, a "hot" tumor is a tumor that exhibits higher levels of immune infiltration by, e.g., CD8+ T cells, than cold tumors. In certain embodiments, a hot tumor has a CD8+ T-cell density of greater than about 3000 cells, e.g., greater than about 4000 cells or greater than about 5000 cells per 1 $mm^2$ sample.

CD8+ (cytotoxic) T-cells are generated in the thymus and express the T-cell receptor. CD8+ T-cells express a dimeric co-receptor, CD8, usually composed of one CD8α and one CD8β chain. CD8+ T-cells recognize peptides presented by MHC Class I molecules, found on all nucleated cells. The CD8 heterodimer binds to a conserved portion (the α3 region) of MHC Class I during T-cell/antigen presenting cell interactions. When a CD8+ T-cell recognizes an antigen and becomes activated, it can secrete cytokines, produce and release cytotoxic granules, and activate the caspase cascade to kill malignant cells.

A high density of tumor-infiltrating CD8+ T-cells is frequently associated in the art with favorable clinical outcomes in a remarkably large spectrum of cancers, and indicate an ongoing host immune response, and the prognostic value of a high density of tumor infiltrating lymphocytes on clinical outcome has been assessed in a variety of cancer entities (Zhang et al (2003) NEJM 348:203-13; Galon et al. (2006) Science 313:1960-64; Gao et al. (2007) J Clin Oncol. 25:2586-93; Gooden et al. (2011) Br J Cancer 105:93-103).

The terms "CD8 density," "CD8+ density" or "CD8+ T-cell density" refer to the number of CD8+ T-cells present in a sample, e.g., in a tumor sample. In exemplary embodiments, a CD8+ T-cell density is the number of cells present in a sample, e.g., a 1 $mm^2$ sample (e.g., a punch biopsy) or a 1 mL (i.e., 1 $cm^3$) sample (e.g., a liquid biopsy) of a tumor from a subject. In certain exemplary embodiments, a low CD8+ T-cell density (which is associated with a "cold" tumor) is less than about 3000 cells per 1 $mm^2$ or per 1 mL sample, less than about 2900 cells per 1 $mm^2$ or per 1 mL sample, less than about 2800 cells per 1 $mm^2$ or per 1 mL sample, less than about 2700 cells per 1 $mm^2$ or per 1 mL sample, less than about 2600 cells per 1 $mm^2$ or per 1 ml, sample, less than about 2500 cells per 1 $mm^2$ or per 1 mL, sample, less than about 2400 cells per 1 $mm^2$ or per 1 mL sample, less than about 2300 cells per 1 $mm^2$ or per 1 mL sample, less than about 2200 cells per 1 $mm^2$ or per 1 mL sample, less than about 2100 cells per 1 $mm^2$ or per 1 sample, less than about 2000 cells per 1 $mm^2$ sample, less than about 1900 cells per 1 $mm^2$ sample, less than about 1800 cells per 1 $mm^2$ or per 1 mL sample, less than about 1700 cells per 1 $mm^2$ or per 1 mL sample, less than about 1600 cells per 1 $mm^2$ or per 1 mL sample, less than about 1500 cells per 1 $mm^2$ or per 1 mL sample, less than about 1400 cells per 1 $mm^2$ or per 1 mL sample, less than about 1300 cells per 1 $mm^2$ or per 1 mL, sample, less than about 1200 cells per 1 $mm^2$ or per 1 mL sample, less than about 1100 cells per 1 mm or per 1 mL, sample, less than about 1000 cells per 1 $mm^2$ or per 1 mL sample, less than about 900 cells per 1 $mm^2$ or per 1 mL sample, less than about 800 cells per 1 $mm^2$ or per 1 mL sample, less than about 700 cells per 1 $mm^2$ or per 1 mL sample, less than about 600 cells per 1 $mm^2$ or per 1 mL sample, less than about 500 cells per 1 $mm^2$ or per 1 ml, sample, less than about 400 cells per 1 $mm^2$ or per 1 mL sample, less than about 300 cells per 1 $mm^2$ or per 1 mL sample, less than about 200 cells per 1 $mm^2$ or per 1 mL, sample, or less than about 100 cells per 1 $mm^2$ or per 1 mL sample. In certain exemplary embodiments, a low CD8+ T-cell density is between about 3000 and 500 cells per 1 $mm^2$ or per 1 mL sample, between about 2900 and 500 cells per 1 $mm^2$ or per 1 mL sample, between about 2800 and 500 cells per 1 $mm^2$ or per 1 mL sample, between about 2700 and 500 cells per 1 $mm^2$ or per 1 sample, between about 2600 and 500 cells per 1 $mm^2$ or per 1 mL sample, between about 2500 and 500 cells per 1 $mm^2$ or per 1 mL sample, between about 2400 and 500 cells per 1 $mm^2$ or per 1 mL sample, between about 2300 and 500 cells per 1 $mm^2$ or per 1 mL, sample, between about 2200 and 500 cells per 1 $mm^2$ or per 1 mL sample, between about 2100 and 500 cells per 1 $mm^2$ or per 1 mL sample, between about 2000 and 500 cells per 1 $mm^2$ or per 1 mL sample, between about 1900 and 500 cells per 1 $mm^2$ or per 1 mL sample, between about 1800 and 500 cells per 1 $mm^2$ or per 1 mL sample, between about 1700 and 500 cells per 1 $mm^2$ or per 1 mL sample, between about 1600 and 500 cells per 1 $mm^2$ or per 1 mL sample, 1500 and 500 cells per 1 $mm^2$ or per 1 mL sample, between about 1400 and 600 cells per 1 $mm^2$ or per 1 mL sample, between about 1300 and 700 cells per 1 $mm^2$ or per 1 mL sample, between about 1200 and 800 cells per 1 $mm^2$ or per 1 mL sample, between about 1100 and 900 cells per 1 $mm^2$ or per 1 mL sample, or between about 1050 and 950 cells per 1 $mm^2$ or per 1 mL sample. In certain exemplary embodiments, a tow CD8+ T-cell density is between about 10 and 1000 cells per 1 $mm^2$ or per 1 mL sample, between about 20 and 900 cells per 1 $mm^2$ or per 1 mL sample, between about 30 and 800 cells per 1 $mm^2$ or per 1 mL sample, between about 40 and 700 cells per 1 $mm^2$ or per 1 mL sample, between about 50 and 600 cells per 1 $mm^2$ or per 1 mL sample, between about 60 and 500 cells per 1 $mm^2$ or per 1 mL sample, between about 70 and 400 cells per 1 $mm^2$ or per 1 mL, sample, between about 80 and 300 cells per 1 $mm^2$ or per 1 mL sample, or between about 90 and 100 cells per 1 $mm^2$ or per 1 mL sample. In certain exemplary embodiments, a sample contains no detectable CD8+ T-cells.

"CDR" or "CDRs" as used herein means complementarity determining region(s) in an immunoglobulin variable region, defined using the Kabat numbering system, unless otherwise indicated.

A "checkpoint inhibitor" refers to a molecule that totally or partially reduces, inhibits, interferes with or modulates one or more checkpoint proteins. Checkpoint proteins regulate T-cell activation or function. Numerous checkpoint proteins are known, such as CTLA-4 and its ligands CD80 and CD86; and PD1 and its ligands PDL1 and PDL2 (Pardoll (2012) *Nature Reviews Cancer* 12: 252-264). These proteins are responsible for co-stimulatory or inhibitory interactions of T-cell responses. Checkpoint proteins regulate and maintain self-tolerance and the duration and amplitude of physiological immune responses. In certain embodiments, checkpoint inhibitors include antibodies or can be derived from antibodies.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytotoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Clothia" as used herein means an antibody numbering system described in A1-Lazikani et al., J M B 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering (or substantially altering) the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) Molecular Biology of the Gene. The Benjamin Cummings Pub. Co., p. 224 (4th Ed.)). In addition, substitutions of structurally or functionally similar amino acids are less likely to disrupt biological activity.

"Comprising" or variations such as "comprise," "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, if a gene signature score is defined as the composite RNA expression score for a set of genes that consists of a specified list of genes, the skilled artisan will understand that this gene signature score could include the RNA expression level determined for one or more additional genes, preferably no more than three additional genes, if such inclusion does not materially affect the predictive power.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L, et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res, Found., Washington, D.C.; Schwartz, R. M., et al., "Matrices for detecting distant relationships," in Atlas of Protein Sequence and Structure, (1978) vol. 5, suppl. 3. M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3;66-70; Henikoff, S., et al., (1992) Proc. Natl. Acad. Sci. USA 89;10915-10919; Altschul, S. F., et al., (1993) J, Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci, USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab," as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al, (1991) Nature 352: 624-628 and Marks et al. (1991) J. Mol, Biol. 222: 581-597, for example. See also Presta (2005) J. Allergy Clin. Immunot. 116:731.

"Interferon gamma" and "IFNγ" (also called immune or type II interferon), refers to a pleiotropic cytokine involved in the regulation of nearly all phases of immune and inflammatory responses, including the activation, growth and differentiation of T-cells, B-cells, macrophages, NK cells and other cell types such as endothelial cells and fibroblasts, IFNγ enhances MHC expression on antigen-presenting cells, and also plays an important role in activating lymphocytes to enhance anti-tumor effects.

IFNγ can contribute to the containment of tumor progression and growth by increasing tumor antigen presentation to tumor-specific T-cells and increasing susceptibility to NK cytotoxicity. In addition to promoting an immune response to the tumor, IFN-γ can also induce expression of tumor suppressing factors.

"Genetically modified oncolytic virus," as used herein, refers to an oncolytic virus that has been modified as compared to a wild-type version of the virus, typically to remove and/or insert one or more genes. A preferred genetically modified oncolytic virus of the invention is talimogene laherparepvec, also known as IMLGIC® (INN=talimogene laherparepvec), a genetically engineered herpes virus that is commercially available from Amgen Inc. (Thousand Oaks, CA). Talimogene laherparepvec is described in, e.g., WO 2014036412, incorporated herein by reference in its entirety for all purposes.

Talimogene laherparepvec, HSV-1 (strain JS1) ICP34.5-/ ICP47-hGM-CSF (previously known as OncoVex$^{GM-CSF}$), is an intratumorally delivered oncolytic immunotherapy comprising an immune-enhanced HSV-1 that selectively replicates in solid tumors. (Lin et al., Gene Therapy, 10:292-303, 2003; U.S. Pat. Nos. 7,223,593 and 7,537,924.) The HSV-1 was derived from Strain JS1 as deposited at the European collection of cell cultures (ECAAC) under accession number 01010209. In talimogene laherparepvec, the HSV-1 viral genes encoding ICP34.5 have been functionally deleted. Functional deletion of ICP34.5, which acts as a virulence factor during HSV infection, limits replication in non-dividing cells and renders the virus non-pathogenic. In addition, in talimogene laherparepvec, the HSV-1 viral gene encoding ICP47 (which blocks viral antigen presentation to major histocompatibility complex class I and II molecules) has been functionally deleted. Functional deletion of ICP47 also leads to earlier expression of US11, a gene that promotes virus growth in tumor cells without decreasing tumor selectivity. Finally, the coding sequence for human GM-CSF, a cytokine involved in the stimulation of immune responses, has been inserted into the viral genome of talimogene, laherparepvec. The insertion of the gene encoding human GM-CSF is such that it replaces nearly all of the ICP34.5 gene, ensuring that any potential recombination event between talimogene laherparepvec and wild-type virus could only result in a disabled, non-pathogenic virus and could not result in the generation of wild-type virus carrying the gene for human GM-CSF. The HSV thymidine kinase (TK) gene remains intact in talimogene laherparepvec, which renders the virus sensitive to anti-viral agents such as acyclovir. Therefore, acyclovir can be used to block talimogene laherparepvec replication, if necessary.

In a prior phase 3 clinical trial, intratumoral injection of talimogene laherparepvec into melanoma metastases improved the durable response rate compared with subcutaneous GM-CSF in patients with advanced melanoma (Andthacka et al. (2015). Talimogene Laherparepvec Improves Durable Response Rate in Patients With Advanced Melanoma. J Clin Oncol 33, 2780-2788). Promising anti-tumor activity was also demonstrated when talimogene laherparepvec was given together with the checkpoint inhibitor ipilimumab, which blocks the cytotoxic T-cell associated-antigen 4 (CTLA-4) (Chesney, J., Collichio, F., Andtbacka, R. H., Puzanov, I., Glaspy, J. A., Milhem, M., Hamid, O., Cranmer, L., Saenger, Y., Ross, M., et al. (2016). Interim safety and efficacy of a randomized (1:1), open-label phase 2 study of talimogene laherparepvec (T) and ipilimumab (I) vs I alone in unresected, stage IIIB-IV melanoma. Ann Oncol 27 (6), 379-400; Puzanov, I., Milhem, M. M., Minor, D., Hamid, O., Li, A., Chen, L., Chastain, M., Gorski, K. S., Anderson, A., Chou, J., et al. (2016). Talimogene Laherparepvec in Combination With Ipilimumab in Previously Untreated, Unresectable Stage IIIB-IV Melanoma. J Clin Oncol 34, 2619-2626).

Talimogene laherparepvec (IMLYGICO) was approved as a monotherapy treatment for metastatic melanoma in the U.S., European Union, and Australia in 2015. In OPTiM, a multicenter, phase 3 clinical trial that enrolled patients with metastatic melanoma that could not be surgically removed, patients who received talimogene laherparepvec were significantly more likely to experience a durable response compared with patients who received the comparator therapy, GM-CSF. (Andtbacka RHI, et al., J. Clin Oncol., 33:2780-2788 (2015)).

In addition, the safety of ICP34.5-functionally deleted HSVs has been shown in multiple clinical studies (MacKie et al, Lancet 357: 525-526, 2001; Markert et al, Gene Ther 7: 867-874, 2000; Rampling et al, Gene Ther 7:859-866, 2000; Sundaresan et al, J. Virol 74: 3822-3841, 2000; Hunter et al, J Viral August; 73(8): 6319-6326, 1999).

Talimogene laherparepvec produces a direct oncolytic effect by replication of the virus in the tumor, and induction of an anti-tumor immune response enhanced by the local expression of GM-CSF. Intended clinical effects include, but are not limited to, the destruction of injected tumors; the destruction of local, local-regional, and distant uninjected tumors; a reduction in the development of new metastases; a reduction in the rate of overall progression; and prolonged overall survival.

Talimogene laherparepvec has been tested for efficacy in a variety of in vitro (cell line) and in vivo murine tumor models and has been shown to eradicate tumors or substantially inhibit their growth at doses comparable to those used in clinical studies. Non-clinical has also confirmed that GM-CSF enhances the immune response generated, enhancing both injected and uninjected tumor responses, and that increased surface levels of MHC class I molecules result from the deletion of ICP47. Talimogene laherparepvec has been injected into normal and tumor-bearing mice to assess its safety. In general, the virus has been well tolerated, and doses up to $1\times10^8$ PFU/dose have given no indication of any safety concerns. (See, for example, Liu et al., Gene Ther 10: 292-303, 2003).

Clinical studies have been or are being conducted in several advanced tumor types (advanced solid tumors, melanoma, squamous cell cancer of the head and neck, and pancreatic cancer), with over 400 subjects treated with talimogene laherparepvec (see, for example, Hu et al., Clin Can Res 12: 6737-6747, 2006; Harrington et al., J Clin Oncol. 27(15a):abstract 6018, 2009; Kaufman et al., Ann Surgic Oncol. 17: 718-730, 2010; Kaufman and Bines, Future Oncol. 6(6); 941-949, 2010).

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length.

"Patient" or "subject" refers to any single subject for which therapy is desired or that is participating in a clinical trial, epidemiological study or used as a control, including humans, non-human primates, mammalian veterinary patients such as cattle, horses, dogs, cats and the like, and research animals such as non-human primates, rats, mice, dogs, rabbits and the like.

Pembrolizumab is a humanized monoclonal antibody against that binds to and blocks PD-1. Pembrolizumab works by increasing the ability of the body's immune system to help detect and fight tumor cells by blocking the interaction between PD-1 and its ligands, PD-L1 and PD-L2, thereby activating T lymphocytes which may affect both tumor cells and healthy cells.

Pembrolizumab monotherapy is known to treat melanoma, non-small cell lung cancer and squamous cell carcinoma of the head and neck in affected individuals having higher densities of baseline CD8+ T-cell infiltrations, IFγ gene signature and PD-L1 expression than levels found in non-responsive individuals. This was understood by others in the art to limit the utility of pembrolizumab in individuals with a low CD8+ T-cell density, a negative IFNγ gene signature and/or a low or negative PD-L1 status.

As used herein, "pembrolizumab" refers to a commercially available monoclonal antibody under the proprietary name of KEYTRUDA® (Merck Sharp & Dohme Corp., Whitehouse Station, NJ), described in WO2016196173 and U.S. Pat. Nos. 8,354,509 and 8,900,587, incorporated herein by reference in their entireties for all purposes, as well as variants and antigen-binding fragments thereof. Pembrolizumab can be characterized by one or any combination of the heavy chain domain, light chain domain, heavy chain variable domain, light chain variable domain, heavy chain complementarity-determining and light chain complementarity-determining sequences described Infra.

Pembrolizumab can comprise a heavy chain sequence set forth as QVQLVQSGVEVKKPGASVKVSCK-ASGYTFTNYYMYWVRQAPGQGLEWMGGINPS NGGTNFNEKFKNRVILITDSSTITAYMELKSLQEDD-TAVYYCARRDYRFUMGFDY WGQGTTVTVSSAS-TKGPSVFPLAPCSRSTSESTAALGCLVKDYF-PEPVTVSWNSGAL TSGVHTFPAVLQSSCUYS-LSSVVTVPSSSLGIKTYTCNVDKPSNTKVDKRVES-KYG PPCPPCPAPEFLGGPSVFLFPPKPKDTLMISRTPE-VTCVVVDVSQEDPEVQFNWYVDG VEVII-NAKTKPREEQFN-STYRVVSVLTVLHQDWLNGKEYKCKVSNKGLPSS-IEKTIS K AKGQPREPQVYTLPPSQEEMIKNQVSLT-CLVKGFYPSDIA VEWESNGQPENNYKTTP PVLDSDGSFFLY-SRLTVDKSRWQEGNVFSCSVMHEALFINEYTQKSIS-LSLGK (SEQ ID NO:1), and a light chain sequence set forth as EIVLTQSPATLSLSPGERATLSCRASKGVSTSGYSY-LIIWYQQKPGQ APRLLIYLA-SYLESGVPARFSGSGSGTDFTLTISSLEPED-FAVYYCQHSRDLPLTFGGG TKVEIKRTVAAPSVFIFPPSDEQLKSG-TASVVCLLNNFYPREAKVQWKVDNALQSGN SQESVTEQDSKDSTYSLSSTLTLSKADYEKHKVY-ACEVTIIQGLSSPVTKSFNRGEC (SEQ ID NO:2).

Pembrolizumab can comprise a heavy chain variable (VH) domain sequence set forth as QVQLVQSGVEVKKP-GASVKVSCKASGYTFTNYYMYWVRQAPGQ-GLEWMGGINPS NGGTNFNEKFKNRVTUFTDSSTT-TAYMELKSLQFDDTAVYYCARRDYRFDMGFDY WGQGTTVTVSS (SEQ ID NO:3), and a light chain variable (VL) domain set forth as EIVLTQSPATLSLSPGER-ATLSCRASKGVSTSGYSYLHWYQQKPGQAPRLLIY-LASYL ESGVPARFSGSGSGTDFTLTISSLEPED-FAVYYCQHSRDLPLTFGGGTKVEIK (SEQ ID NO:4).

Pembrolizumab can comprise the following heavy chain complementarity-determining regions (HCDRs): NYYMY (HCDR1, SEQ ID NO:5); GINPSNGGTNFN (HCDR2, SEQ ID NO:6); and RDYRFDMGFDY (HCDR3, SEQ NO:7).

Pembrolizumab can comprise the following light chain complementarity-determining regions (LCDRs): RASKGVSTSGYSYLH (LCDR1, SEQ ID NO:8); LASYLES (LCDR2, SEQ ID NO:9); and QHSRDLPLT (LCDR3, SEQ ID NO:10).

In certain embodiments, pembrolizumab, a pembrolizumab variant or an antigen-binding fragment thereof is provided comprising heavy chain CDRs SEQ ID NOs: 5, 6 and 7 and light chain CDRs of SEQ ID NOs: 8, 9 and 10.

In other embodiments, pembrolizumab, a pembrolizumab variant or an antigen-binding fragment thereof is provided comprising heavy chain and light chain CDR sequences from a VH/VL sequence pair of SEQ ID NO:3 and SEQ ID NO:4.

In still other preferred embodiments, pembrolizumab, a pembrolizumab variant or an antigen-binding fragment thereof is provided comprising a heavy chain variable region comprising SEQ ID NO:3 or a variant thereof and/or a light chain variable region comprising SEQ NO:4 or a variant thereof. In other embodiments, the pembrolizumab variant or antigen-binding fragment thereof comprises a heavy chain variable region comprising as sequence with at least 80% sequence homology or identity (e.g., 80%, 85%, 90%, 95%, 98% or 99%) to SEQ ID NO:3 and/or a light chain variable region comprising a sequence with at least 80% sequence homology or identify (e.g., 80%, 85%, 90%, 95%, 98% or 99%) to SEQ ID NO:4.

As used herein, a "variant of a heavy chain variable region sequence" is a sequence that is identical to the reference sequence, except having up to 17 conservative amino acid substitutions in the framework region (i.e., outside of the CDRs), and preferably having fewer than ten, nine, eight, seven, six or five conservative amino acid substitutions in the framework region. As used herein, a "variant of a light chain variable region sequence" is a sequence that is identical to the reference sequence, except having up to five conservative amino acid substitutions in the framework region (i.e., outside of the CDRs), and preferably having fewer than four, three or two conservative amino acid substitution in the framework region.

In still other embodiments, pembrolizumab, a pembrolizumab variant or an antigen-binding fragment thereof is provided comprising a heavy chain comprising SEQ ID NO:1 or a variant thereof and/or a light chain comprising SEQ ID NO:2 or a variant thereof. In other embodiments, the pembrolizumab variant or antigen-binding fragment thereof comprises a heavy chain comprising as sequence with at least 80% sequence homology or identity (e.g., 80%, 85%, 90%, 95%, 98% or 99%) to SEQ NO:1 and/or a light chain comprising a sequence with at least 80% sequence homology or identify (e.g., 80%, 85%, 90%, 95%, 98% or 99%) to SEQ ID NO:2.

As used herein, a "pembrolizumab variant" refers to a monoclonal antibody which comprises heavy chain and light chain sequences that are identical to those of pembrolizumab, except for having up to five conservative amino acid substitutions in the framework region (i.e., outside of the CDRs), and preferably has less than four, three or two conservative amino acid substitution in the framework region, and having up to 17 conservative amino acid substitutions in the framework region (i.e., outside of the CDRs), and preferably has less than ten, nine, eight, seven, six or five conservative amino acid substitutions in the framework region, and preferably has less than four, three or two conservative amino acid substitution in the framework region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as or better than pembrolizumab with respect to the following properties: binding affinity to PD-1 and neutralizing effect in vivo.

In certain embodiments, hiosimilars of pembrolizumab are provided. As used herein, the term "biosimilar" is used in a manner that is consistent with the working definition promulgated by the U.S. Food and Drug Administration, which defines a biosimilar product to be one that is "highly similar" to a reference product (despite minor differences in clinically inactive components). In practice, there can be no clinically meaningful differences between the reference product and the biosimilar product in terms of safety, purity, and potency (Public Health Service (PHS) Act § 262). In certain embodiments, a double-blind, single-dose comparative pharmacokinetic (PK) crossover study is performed to compare pembrolizumab with a candidate biosimilar antibody to determine comparable bioavailability.

As used herein, the term "reference product," is used to refer to commercially available pembrolizumab.

The PD-1 receptor (also known as CD279) is expressed on the surface of activated T-cells. Its ligands, PD-L1 (B7-H1; CD274) and PD-L2 (B7-DC; CD273), are commonly expressed on the surface of dendritic cells or macrophages. PD1 and PD-L1/PD-L2 belong to the family of immune checkpoint proteins that act as co-inhibitory factors, which can halt or limit the development of the T cell response. PD1/PD-L1 interaction ensures that the immune system is activated only at the appropriate time in order to minimize the possibility of chronic autoimmune inflammation. When PD-L1 binds to PD-1, an inhibitory signal is transmitted into the T-cell, which reduces cytokine production and suppresses T-cell proliferation. Tumor cells exploit this immune-checkpoint pathway as a mechanism to evade detection and inhibit the immune response.

PD-L1 is commonly overexpressed on tumor cells or on non-transformed cells in the tumor microenvironment. PD-L1 expressed on the tumor cells binds to PD-1 receptors on the activated T-cells, which leads to the inhibition of the cytotoxic T-cells. These deactivated T-cells remain inhibited in the tumor microenvironment. The PD1/PD-L1 pathway represents an adaptive immune resistance mechanism that is exerted by tumor cells in response to endogenous anti-tumor activity.

As used herein, "PD-L1 status" or "PD-L1 expression status" refers to the level of PD-L1 present in a sample, e.g., in a tumor sample. In certain embodiments, PD-L1 status is expressed as a "tumor proportion score" or "TPS," which refers to the percentage of tumor cells in a sample that express a detectable level of PD-L1. (See Garon et al. (2015) NEJM 372: 2018-28.) A PD-L1 status is "underexpressed" or "reduced" or "low" if PD-L1 is expressed in between about 1% and about 49% of tumor cells in a sample, i.e., the PD-L1 status is between about 1% and about 49%. A PD-L1 status is "negative" if PD-L1 is expressed in fewer than about 1% of tumor cells in a sample, i.e., the PD-L1 status is less than about 1%. A PD-L1 status is "high" if PD-L1 is expressed in about 50% or more of the tumor cells in a sample, i.e., the PD-L1 status is about 50% or greater.

In some preferred embodiments, an underexpressed, reduced or low PD-L1 status is less than about 50%, or is about 49%, about 48%, about 47%, about 46%, about 45%, about 44%, about 43%, about 4 about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2 or about 1%. In particularly preferred embodiments, an underexpressed, reduced or low PD-L1 status is about 10%, about 9%, about 8%, about 7%, about 6%, about 5%, about 4%, about 3%, about 2%, or about 1%. In some preferred embodiments, an underexpressed, reduced or low PD-L1 status is between about 1% and about 10%, between about 1% and about 9%, between about 1% and about 8%, between about 1% and about 7%, between about 1% and about 6%, between about 1% and about 5%, between about 1% and about 4%, between about 1% and about 3%, between about 1% and about 2%, between about 2% and about 6%, between about 3% and about 7%, between about 4% and about 8%, or between about 5% and about 9%.

In some preferred embodiments, a negative PD-L1 status is less than about 1%, or is about 0.9%, about 0.8%, about 0.7%, about 0.6%, about 0.5%, about 0.4%, about 0.3%, about 0.2%, about 0.1%, about 0.05%, about 0.01%, about 0.005%, about 001%, or about 0% (i.e., all none of the tumor cells have a detectable level of PD-L1).

In some preferred embodiments, a high PD-L1 status is about 50% or greater, e.g., is about 55%, about 60%, about 65%, about 70%, about 75%, about 80%0, about 85%, about 90%, about 95%, about 96%, about 97%, about 98%, about 99%, or about 100% (i.e., all of the tumor cells have a detectable level of PD-L1).

In certain preferred embodiments, PD-L1 expression is detected using a diagnostic anti-human PD-L1 antibody, or antigen-binding fragment thereof, in an IHC assay on an FFPE or frozen tissue section of a tumor sample removed from the subject. In certain embodiments, PD-L1 expression may be assessed in a sample (e.g., a tumor sample) using a PD-L1 IHC 22C3 pharmDx immunohistochemistry assay (Dako North America, Carpinteria, CA). (See Baud, A. I., Woichok, J. D., Robert, C., Hwu, W. J., Weber, J. S., Ribas, A., Hodi, F. S., Joshua, A. M., Kefford, R., Hersey, R, et al. (2016). Programmed Death-Ligand 1 Expression and Response to the Anti-Programmed Death 1 Antibody Pembrolizumab in Melanoma. J Clin Oncol 34, 4102-4109.) Typically, a subject's physician would order a diagnostic test to determine PD-L1 expression in a tumor tissue sample removed from the patient prior to initiation of treatment with pembrolizumab, pembrolizumab variant and/or antigen-binding fragment thereof and/or talimogene laherparepvec, but it is envisioned that the physician could order the first or subsequent diagnostic tests at any time after initiation of treatment, such as for example after completion of a treatment cycle.

"Primary pembrolizumab antibody" and "primary pembrolizumab variant antibody" as used herein, refer to an antibody that binds specifically to PD-L1 in a tissue section, and is generally the first antibody used in an IHC assay of PD-L1 expression in a tumor sample. In one embodiment, the primary antibody is the only antibody used in the IHC assay.

"Secondary antibody," as used herein, refers to an antibody that binds specifically to a primary pembrolizumab antibody or a primary pembrolizumab variant antibody, thereby forming a bridge between the primary antibody and a subsequent detection reagent, if any. The secondary antibody is generally the second antibody used in an IHC assay of PD-L1 expression in a tumor sample.

"Patient," as used herein, refers to a subject having a cancer that is treated by a combination of pembrolizumab a pembrolizumab variant or an antigen-binding fragment thereof and talimogene laherparepvec.

In certain embodiments, a patient has a cancer that is associated with one or more of a CD8+ infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and a low level of IFNγ gene signature, including, but not limited to, melanoma (e.g. cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2− (HR+), triple-negative), ovarian cancer, bladder cancer (e.g., transitional cell cancer, urothelial cancer), prostate cancer (e.g., castration-resistant), sarcoma (e.g., soft tissue, bone), renal cell cancer, gastric cancer, esophageal cancer, anal canal cancer, binary tract cancer or pancreatic cancer.

In other embodiments, a patient has a cancer that is responsive to monotherapy with a checkpoint inhibitor (e.g., with anti-PD-L1 therapy or anti-PD-1 therapy pembrolizumab, a pembrolizumab variant or an antigen-binding fragment thereof)), which may optionally be associated with one or more of a CD8+ infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status, and a low level of IFNγ gene signature, including, but not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g., ER+/HER2− breast cancer, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), binary tract cancer, multiple myeloma, lymphoma (e.g., mediastinal large B-cell lymphoma, Hodgkin's lymphoma) or mesothelioma.

"Probe" as used herein means an oligonucleotide that is capable of specifically hybridizing under stringent hybridization conditions to a transcript expressed by a gene of interest, and in some preferred embodiments, specifically hybridizes under stringent hybridization conditions to the particular transcript for the gene of interest.

"RECIST 1.1 Response Criteria" as used herein means the definitions set forth in Eisenhauer et al., E. A. et al., Eur. J Cancer 45:228-247 (2009) for target lesions or non-target lesions, as appropriate, based on the context in which response is being measured.

"Reference IFN-γ gene signature score," as used herein, means the score for an IFN-γ gene signature that has been determined to divide at least the majority of responders from at least the majority of non-responders in a reference population of subjects who have the same tumor type as a test subject and who has been treated with a combination therapy of pembrolizumab, a pembrolizumab variant and/or an antigen-binding fragment thereof and talimogene laherparepvec. Preferably, at least any of 60%, 70%, 80%, or 90% of responders in the reference population will have an IFN-γ gene signature score that is below the selected reference score (e.g., a pre-specified threshold of a control panel) (i.e., a negative IFNγ gene signature), while the IFN-γ gene signature for at least any of 60%, 70% 80%, 90% or 95% of the non-responders in the reference population will be greater than the selected reference score (i.e., a positive IFNγ gene signature). In some preferred embodiments, responders in the reference population are defined as subjects who achieved a partial response (PR) or complete response (CR) as measured by RECIST 1.1 criteria, and non-responders are defined as not achieving any RECIST 1.1 clinical response.

"Responder patient" when referring to a specific anti-tumor response to treatment with a combination therapy described herein, means the patient exhibited the anti-tumor response.

"Sample" when referring to a tumor or any other biological material referenced herein, means a sample that has been removed from the subject.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer pembrolizumab, a pembrolizumab variant or an antigen-binding fragment thereof and talimogene laherparepvec, and/or another therapeutic agent, to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, J. Null. Med. 50:1S-10S (2009); Eisenhauer et al., supra). In some preferred embodiments, response to pembrolizumab, a pembrolizumab variant and/or an antigen-binding fragment thereof, and/or talimogene laherparepvec is assessed using RECIST 1.1 criteria. In some embodiments, the treatment achieved by a therapeutically effective amount is any of a partial response (PR), a complete response (CR), progression free survival (PFS), disease free survival (DES), objective response (OR) or overall survival (OS). In some preferred embodiments, a CD8+ cell density, a gene signature biomarker and/or a low or negative PD-L1 status of the invention predicts whether a subject with a solid tumor is likely to achieve a PR or a CR. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Tumor" as it applies to a subject diagnosed with, or suspected of having a cancer, refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load," refers to the total amount of tumor material distributed throughout the body. Tumor burden refers to the total number of cancer cells or the total size of tumor(s) throughout the body, including lymph nodes and bone narrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic, resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

In some embodiments of the treatment methods, medicaments and uses of the invention disclosed herein, the individual is a human and the cancer correlates with a low or negative PD-L1 status and/or a tow or negative CD8+ T-cell density, including, but not limited to: melanoma (generally highly T-cell infiltrated high % PD-L1+; subset PD-L1/TIL low, Tumeh et al Nature 2014; Daud, J C O 2016); non-small cell lung cancer (some high % PD-L1+; subset PD-L1/TIL low, Topalian NEJM 2012; Garon et al NEJM 2015; Ameratunga PlosOne 2016); recurrent or metastatic squamous cell carcinoma of the head and neck; HPV positive head and neck cancer or HPV negative head and neck cancer (generally highly T-cell infiltrated high % PD-L1+; subset PD-L1/TIL low apparently true for both HPV-f- and HPV-head and neck cancers, Lyford-Pyrke CanRes 2013; Maim Head Neck 2015; Mandal et al JCI 2016); colorectal cancer (mismatch repair deficient CRC/Lynch syndrome highly PD-L1+ TIL infiltrated; MSI stable CRC generally cold tumors, Le et. al NEJM 2015; Mahy CanRes 2015); HER2+ breast cancer (CD8+ high (61%) Foxp3 Treg high; lymphocyte predominant breast cancers (16%), Stanton JAMA (2016)); HER2−(FIR+) breast cancer (CD8+ mid (43%) lower Foxp3 Treg; lymphocyte predominant breast cancers (6%), Stanton JAMA (2016)); triple-negative breast cancer (CD8+ high (60%) Foxp3 Treg high; lymphocyte predominant breast cancers (20%), Stanton JAMA (2016)); ovarian cancer (prognostic data around TIL similar to melanoma; response, rate 15-40% in Hamanishi JCO, Hamanishi JCO, 2015; Mandai IJCO 2016); bladder cancer (correlation with PD-L1; possible TIL bladder cancer correlation for checkpoint inhibitors, Powles Nature 2014 (Atezo); Kim ICU 2016); uveal melanoma (bmx data presented Piperno-Neumann ASCO 2016, uveal melanoma); castration resistant prostate cancer (Paucity of PD-L1 expression in prostate cancer: innate and adaptive immune resistance, Martin Prostate Cancer and Prostatic Diseases 2015 Kim ICU 2016); soft tissue or bone sarcoma (modest response rate; prognostic PD-L1/TIL data available ore digging needed to find clinical data with TIL vs checkpoint inhibitor response, L. Paoluzzi Clinical Sarcoma Research 2016; D'Angelo S P Human Pathol 2015); and renal cell cancer (pembrolizumab primarily used in combination in RCC: Ipi, axitinib, anti-VEGF etc. generally highly T-cell infiltrated high % PD-L1+; subset PD-L1/TIL low, Taube Clin Can Res 2014).

In other embodiments of the treatment methods, medicaments and uses of the invention disclosed herein, the individual is a human and the cancer correlates with a low or negative IFNγ mRNA signature, including, but not limited to: melanoma (ORR/PFS correlation with IFNγ signature, Ayers et al JITC 2015); head and neck cancer ("Inflamed phenotype" signatures are strong predictors of clinical benefit from anti-PD-1 treatment for HNSCC even among a group of patients already considered to be PD-L1+; Clinical trial information: NCT01848834, Seiwert ASCO et al JITC); gastric cancer (PFS correlation with IFNγ signature, Ayers et al JITC 2015); esophageal cancer (Overall, those with higher signature scores experienced a more robust response to pembrolizumab and substantial delays in progression; in the non-inflamed, low score group, the ORR was 11% compared with an 43% for those with a higher signature score, Doi et al GCS 2016; this RNA profiling data set from 5 cancers adds to the growing body of evidence that tumor infiltration with activated T-cells is a prerequisite for response to PD-1 checkpoint blockade, and demonstrates that T-cell inflamed gene expression signatures are pan-cancer predictors of clinical benefit from anti-PD-1 treatment, Piha-Paul et al. ASCO 2016); anal canal cancer (as per Piha-Paul et al. ASCO 2016); biliary tract cancer (as per Piha-Paul et al. ASCO 2016); colorectal cancer (as per Pala-Paul et al. ASCO 2016); ovarian cancer (as per Piha-Paul et al. ASCO 2016); and transitional cell cancer (similar to melanoma, SCCHN, and gastric with regard to predictive value of IFNγ signature).

In other embodiments of the above treatment method, medicaments and uses, the individual is a human, and the cancer correlates with low or negative PD-L1 mRNA expression, including, but not limited to: pancreatic cancer (4% PD-L1+, Ayers et al AACR 2015); prostate cancer (14% PD-L1+, Id.); triple negative breast cancer (29% PD-L1+, Id.); melanoma (41% PD-L1+, Id.); non-small cell lung cancer (42% PD-L1+, Id.); urothelial cancer (42% PD-L1+, Id.); and head and neck cancer (59% PD-L1+, Id.) (e.g., recurrent or metastatic squamous cell carcinoma of the head and neck).

Methods, Uses and Medicaments

In one aspect, the invention relates to a method for treating cancer in an individual comprising administering to the individual a combination therapy which comprises pembrolizumab, a pembrolizumab variant or antigen-binding fragments thereof, and talimogene laherparepvec.

The combination therapy may also comprise one or more additional therapeutic agents. The additional therapeutic agent may be, e.g., a chemotherapeutic agent, a biotherapeutic agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF). The specific dosage and dosage schedule of the additional therapeutic agent can further vary, and the optimal dose, dosing schedule and route of administration will be determined based upon the specific therapeutic agent that is being used.

Examples of chemotherapeutic agents include alkylating agents such as thiotepa and cyclophosphamide; alkyl sulfonates such as busulfan, improsulfan and piposulfan; aziri dines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; cally statin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancrati statin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfatnide, uracil mustard; nitrosureas such as carmustine, chlorozotocin, fotemustine, lomustine, nimustine, ranimustine; antibiotics such as the enediyne antibiotics (e.g, calicheamicin, especially calicheamicin gammaII and calicheamicin phiII, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chrornomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellotnycin, mitomycins such as mitomycin C, mycophenolic acid, nogalamycin, olivomycins, peplomycin, potfiromycin, puromycin, quelamycin, rodorubicin, streptonigrin, streptozocin, tubercidin, uhenimex, zinostatin, zorubicin; anti-metabolites such as methotrexate and 5-fluorouracil (5-FU); folic acid analogues such as denopterin, methotrexate, pteropterin, trimetrexate; purine analogs such asfludarabine, 6-mercaptopurine, thiarniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone, trilostane; anti-adrenals such as aminoglutethimide, mitotane, trilostane; folic acid replenisher such as frotinic acid; aceglatone; aklophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethythydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and docetaxel; chlorambucil; gemcitahine;

6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylormthine (DMFO); retinoids such as retinoic acid; capecitahine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LYI 17018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament) concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks and/or are administered to different parts of the body, e.g., one therapeutic agent is administered intratumorally and one therapeutic agent is administered systemically.

In particularly preferred embodiments, talimogene laherparepvec is administered before administration of pembrolizumab, a pembrolizumab variant or an antigen-binding fragment thereof. In other embodiments, talimogene laherparepvec is administered after administration of pembrolizumab, a pembrolizumab variant or an antigen-binding fragment thereof. In another embodiment, talimogene laherparepvec is administered concurrently with pembrolizumab, a pembrolizumab variant or an antigen-binding fragment thereof.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

In certain embodiments, talimogene laherparepvec is administered intratumorally. In certain embodiments, pembrolizumab, a pembrolizumab variant or an antigen-binding fragment thereof is administered parenterally.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is cancer treatment-naive. In other embodiments, the combination therapy is administered to a patient who failed to achieve a sustained response after prior therapy after failed or ineffective therapy with a checkpoint inhibitor (e.g., with anti-PD-L1 therapy or anti-PD-L1 therapy pembrolizumab, a pembrolizumab variant or an antigen-binding fragment thereof)), or a chemotherapeutic agent, i.e., is cancer treatment-experienced.

A combination therapy of the invention is typically used to treat a tumor that is large enough to be found by palpation or by imaging techniques well known in the art, such as MRI, ultrasound, or CAT scan.

A combination therapy of the invention is preferably administered to a human patient who has a cancer that has a low CD8 T-cell density, a negative IFNγ gene signature, and/or has a low or negative PD-L1 status.

Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert et al. (2003) New Engl. J. Med. 348:601-608; Milgrom et al. (1999) New Engl. J. Med. 341: 1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343: 1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy. The optimal dose for pembrolizumab in combination with talimogene laherparepvec may be identified by dose escalation or dose de-escalation of one or both of these agents.

The present invention also provides a medicament which comprises pembrolizumab, a pembrolizumab variant and/or an antigen-binding fragment thereof as described above and a pharmaceutically acceptable excipient. Pembrolizumab, a pembrolizumab variant and/or an antigen-binding fragment thereof may be produced in CHO cells using conventional cell culture and recovery/purification technologies.

In some embodiments, a medicament comprising pembrolizumab, a pembrolizumab variant and/or an antigen-binding fragment thereof may be provided as a liquid formulation or prepared by reconstituting a lyophilized powder with sterile water for injection prior to use. WO 2012/135408 describes the preparation of liquid and lyophilized medicaments comprising pembrolizumab that are suitable for use in the present invention. In some embodiments, a medicament comprising pembrolizumab is provided in a glass vial which contains about 100 mg of pembrolizumab in 4 ml of solution. Each 1 mL, of solution contains 25 mg of pembrolizumab and is formulated in: L-histidine (1.55 mg), polysorbate 80 (0.2 mg), sucrose (70 mg), and water for injection, USP. The solution requires dilution for IV infusion.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg. 50 mg/kg body weight or more. See, e.g., Yang et al. (2003) New Engl. J. Med. 349:427-434; Herold et al. (2002) New Engl. J. Med. 346: 1692-1698; Liu et al. (1999) J. Neurol. Neurosurg. Psych. 67:451-456; Portielji et al. (20003) Cancer Immunol. Immunother. 52: 133-144.

In certain embodiments that employ pembrolizumab, a pembrolizumab variant and/or an antigen-binding fragment thereof, the dosing regimen will comprise administering pembrolizumab, a pembrolizumab variant and/or an antigen-binding fragment thereof at a dose of 1, 2, 3, 5 or 10 mg/kg at intervals of about 14 days (±2 days) or about 21 days (±2 days) or about 30 days (±2 days) throughout the course of treatment. In a preferred embodiment, pembrolizumab, a pembrolizumab variant or an antigen-binding fragment thereof is used at a dose of 2 mg/kg every 3 weeks (e.g., for melanoma). In another preferred embodiment, pembrolizumab, a pembrolizumab variant or an antigen-binding fragment thereof is used at a dose of 200 mg (fixed) every 3 weeks (e.g., for non-small cell lung cancer, head and neck squamous cell carcinoma, and/or Hodgkin's lymphoma).

In other embodiments that employ pembrolizumab, a pembrolizumab variant and/or an antigen-binding fragment thereof in the combination therapy, the dosing regimen will comprise administering pembrolizumab, a pemhrolizumah variant and/or an antigen-binding fragment thereof at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered a parenteral dosing, e.g., an intravenous (IV) infusion, of a medicament comprising any of pembrolizumab, a pembrolizumab variant and/or an antigen-binding fragment thereof.

In a preferred embodiment of the invention, pembrolizumab, a pembrolizumab variant and/or an antigen-binding fragment thereof is administered in a liquid medicament at a dose selected, from the group consisting of 1 mg/kg every two weeks (Q2W), 2 mg/kg Q2W, 3 mg/kg Q2W, 5 mg/kg Q2W, 10 mg Q2W, 1 mg/kg every three weeks (Q3W), 2 mg/kg Q3W, 3 mg/kg Q3W, 5 mg/kg Q3W, 10 mg Q3W and flat-dose equivalents of any of these doses, i.e., such as 200 mg Q3W. In some embodiments, pembrolizumab, a pembrolizumab variant and/or an antigen-binding fragment thereof is provided as a liquid medicament which comprises 25 mg/ml pembrolizumab, 7% (w/v) sucrose, 0.02% (w/v) polysorbate 80 in 10 mM histidine buffer pH 5.5.

In some embodiments, the selected dose of pembrolizumab, a pembrolizumab variant and/or an antigen-binding fragment thereof is administered by IV infusion. In one embodiment, the selected dose of pembrolizumab, a pembrolizumab variant and/or an antigen-binding fragment thereof is administered by IV infusion over a time period of between 25 and 40 minutes, or about 30 minutes.

The present invention also provides a medicament which comprises talimogene laherparepvec and a pharmaceutically acceptable excipient. Talimogene laherparepvec may be suspended in a physiological buffer for intratumoral injection.

In certain embodiments, talimogene laherparepvec is administered by intratumoral injection into injectable tumors at a dose of up to 4.0 ml of $10^6$ plaque forming unit/mL (PFU/mL) at day 1 of week 1, followed by a dose of up to 4.0 ml of $10^8$ PFU/mL at day 1 of weeks 4 and 6, and every 2 weeks (±3 days) thereafter. The recommended volume of talimogene laherparepvec to be injected into the tumor(s) is dependent on the size of the tumor(s) and should be determined according to the injection volume guideline in Table 1.

TABLE 1

Talimogene Laherparepvec injection Volume
Guidelines Based on Tumor Size

| Tumor Size (longest dimension) | Maximum Injection Volume |
|---|---|
| ≥5.0 cm | 4.0 ml |
| >2.5 cm to 5.0 cm | 2.0 ml |
| >1.5 cm to 2.5 cm | 1.0 ml |
| >0.5 cm to 1.5 cm | 0.5 ml |
| ≤0.5 cm | 0.1 ml |

All reasonably injectable lesions (cutaneous, subcutaneous and nodal disease that can be injected with or without ultrasound guidance) should be injected with the maximum dosing volume available on individual dosing occasion. On each treatment day, prioritization of injections is recommended as follows: any new injectable tumor that has appeared since the fast injection; by tumor size, beginning with the largest tumor; any previously uninjectable tumor(s) that is now injectable. The compositions may comprise one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with specific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed.

In some embodiments, the patient is selected for treatment with the combination therapy of the invention if the patient has: (1) a CD8+ T-cell infiltration density of fewer than about 1500, about 1400, about 1300, about 1200, about 1100, about 1000, about 900, about 800, about 700, about 600, or about 500 cells per 1 mm² sample (or per 1 mL sample), a low or negative PD-L1 status, and/or a negative IFNγ gene signature; and (2) has been diagnosed with melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2− (HR+), triple-negative), ovarian cancer, bladder cancer (e.g., transitional cell cancer, urothelial cancer), prostate cancer (e.g., castration-resistant), sarcoma (e.g., soft tissue, bone), renal cell cancer, gastric cancer, esophageal cancer, anal canal cancer, biliary tract cancer or pancreatic cancer.

In other embodiments, the patient is selected for treatment with the combination therapy of the invention if the patient has: (1) a cancer that is responsive to monotherapy with a checkpoint inhibitor (e.g., with anti-PD-L1 therapy or anti-PD-1 therapy (e.g., pembrolizumab, a pembrolizumab variant or an antigen-binding fragment thereof)); (2) which may optionally be associated with one or more of a CD8+ T-cell infiltration density of fewer than about 1500, about 1400, about 1300, about 1200, about 1100, about 1000, about 900, about 800, about 700, about 600, or about 500 cells per 1 mm² sample (or per 1 mL sample), a low or negative PD-L1 status and a negative IFNγ gene signature; and (3) has been diagnosed with melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g., ER+/HER2− breast cancer, inflammatory, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma.

The medicaments described herein may be provided as a kit which comprises a first container and a second container and a package insert. The first container contains at least one dose of a medicament comprising a pembrolizumab, a pembrolizumab variant and/or an antigen-binding fragment thereof, and the second container contains at least one dose of talimogene laherparepvec. The kit can optionally comprise a package insert, or label, which includes instructions for treating a patient for cancer using the medicaments. The first and second containers may be comprised of the same or different shapes (e.g., vials, syringes and bottles) and/or materials (e.g., plastic or glass). The kit may further comprise other materials that may be useful in administering the medicaments, such as diluents, filters, IV bags and lines, needles and syringes. In some preferred embodiments of the kit, the instructions state that the medicaments are intended for use in treating a patient having a cancer that has a CD8+ T-cell density of fewer than 1,000 cells/mm$^2$, a negative IFNγ gene signature and/or a low or negative PD-L1 status.

Pharmaceutical Compositions

The invention pertains to uses of the above-described agents for prophylactic and/or therapeutic treatments as described Infra. Accordingly, pembrolizumab, the pembrolizumab variant and/or the antigen-binding fragment thereof and/or talimogene laherparepvec of the present invention can be incorporated into pharmaceutical compositions suitable for administration. Such compositions typically comprise pembrolizumab, the pembrolizumab variant and/or the antigen-binding fragment thereof or talimogene laherparepvec and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethytenediaminetetraacetic acid; buffers such as acetates, citrates or phosphates and agents for the adjustment of tonicity such as sodium chloride or dextrose pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor Eurm (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Systemic administration can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, pembrolizumab, a pembrolizumab variant and/or an antigen-binding fragment thereof or talimogene laherparepvec are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid, Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack or dispenser together with optional instructions for administration.

The pharmaceutical compositions of the present invention may be administered in a number of ways depending upon whether local or systemic treatment is desired and upon the area to be treated. Administration may be intratumoral or parenteral. Parenteral administration includes intravenous drip, subcutaneous, intraperitoneal or intramuscular injection, intrathecal, or intraventricular administration.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

The types of pharmaceutical excipients that are useful as carriers include stabilizers such as human serum albumin (HSA), hulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

In one embodiment, unit doses or measured doses of a composition that include the pembrolizumab pembrolizumab variant and/or antigen-binding fragment thereof or talimogene laherparepvec are dispensed by an implanted device. The device can include a sensor that monitors a parameter within a subject. For example, the device can include a pump, such as an osmotic pump and, optionally, associated electronics.

Biomarker Testing

A biomarker expression score (e.g., an IFN-γ gene signature score and/or PD-L-1 status) can be determined in a sample of tumor tissue removed from a subject. The tumor may be primary or recurrent, and may be of any type (as described above), any stage (e.g., Stage I, II, III, or IV or an equivalent of other staging system), and/or any histology. The subject may be of any age, gender, treatment history and/or extent and duration of remission.

The tumor sample can be obtained by a variety of procedures including, but not limited to, surgical excision, aspiration or biopsy. The tissue sample may be sectioned and assayed as a fresh specimen. Alternatively, the tissue sample may be frozen for further sectioning. In some preferred embodiments, the tissue sample is preserved by fixing and embedding in paraffin or the like.

The tumor tissue sample may be fixed by conventional methodology, with the length of fixation depending on the size of the tissue sample and the fixative used. Neutral buffered formalin, glutaraldehyde, Bouin's and paraformaldehyde are non-limiting examples of fixatives. In preferred embodiments, the tissue sample is fixed with formalin. In some embodiments, the fixed tissue sample is also embedded in paraffin to prepare a formalin-fixed paraffin-embedded (FFPE) tissue sample.

Typically, the tissue sample is fixed and dehydrated through an ascending series of alcohols, infiltrated and embedded with paraffin or other sectioning media so that the tissue sample may be sectioned. Alternatively, the tumor tissue sample is first sectioned and then the individual sections are fixed.

In some preferred embodiments, a biomarker expression score for a tumor is determined using FFPE tissue sections of about 3-5 micrometers, and preferably 4 or 5 micrometers, which are mounted and dried on a microscope slide.

Diagnostic Testing for IFN-γ Gene Signature Score and/or PD-L1 Status

In one embodiment, the tested tumor sample is from a cancer associated with a low or negative PD-L1 status and/or a negative IFNγ gene signature, and optionally a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), including, but not limited to, melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2– (HR+), triple-negative), ovarian cancer, bladder cancer (e.g., transitional cell cancer, urothelial cancer), prostate cancer (e.g., castration-resistant), sarcoma (e.g., soft tissue, bone renal cell cancer, gastric cancer, esophageal cancer, anal canal cancer, biliary tract cancer or pancreatic cancer.

In another embodiment, the tested tumor sample is from a cancer that is responsive to monotherapy with a checkpoint inhibitor (e.g., with anti-PD-L1 therapy or anti-PD-1 therapy (e.g., pembrolizumab, a pembrolizumab variant or an antigen-binding fragment thereof)), which may optionally be associated with one or more of a CD8+ T-cell infiltration density of fewer than about 1500, about 1400, about 1300, about 1200, about 1100, about 1000, about 900, about 800, about 700, about 600, or about 500 cells per 1 mm sample (or per 1 mL sample), a low or negative PD-L1 status and a negative IFNγ gene signature, including, but not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g. ER+/HER2– breast cancer, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma.

Once a suitable sample of tumor tissue has been obtained, it can be analyzed to quantitate the expression level of each of the genes that comprise the particular IFN-γ gene signature to be scored, e.g., one or any combination of IFNγ, STAT1, CCR5, CXCL9, PRF1, HLA-DRA, CXCL10, CXCL11, ID01 and GZMA, or the mRNA levels of PD-L1. The phrase "determine the expression level of a gene" as used herein refers to detecting and quantifying RNA transcribed from that gene or a protein translated from such RNA. The term "RNA transcript" includes mRNA transcribed from the gene, and/or specific spliced variants thereof and/or fragments of such mRNA and spliced variants. In preferred embodiments, the RNA transcripts whose expression are measured are the transcripts in FIG. 11 and/or PD-L1 transcripts.

A person skilled in the art will appreciate that a number of methods can be used to isolate RNA from the tissue sample for analysis. For example, RNA may be isolated from frozen tissue samples by homogenization in guanidinium isothiocyanate and acid phenol-chloroform extraction. Commercial kits are available for isolating RNA from FFPE samples.

Persons skilled in the art are also aware of several methods useful for detecting and quantifying the level of RNA transcripts within the isolated RNA or whole cell lysates. Quantitative detection methods include, but are not limited to, arrays (i.e., microarrays), quantitative, real time PCR (RT-PCR), multiplex assays, nuclease protection assays, and Northern blot analyses. Generally, such methods employ labeled probes that are complimentary to a portion of each transcript to be detected. Probes for use in these methods can be readily designed based on the known sequences of the genes and the transcripts expressed thereby. In some preferred embodiments, the probes are designed to hybridize to each of the gene signature transcripts identified in FIG. 11. Suitable labels for the probes are well-known and include, e.g., fluorescent, chemiluminescent and radioactive labels.

In some embodiments, assaying a tumor sample for a gene signature of the invention employs detection and quantification of RNA levels in real-time using nucleic acid sequence based amplification (NASBA) combined with molecular beacon detection molecules. NASBA is described, e.g., in Compton J., Nature 350 (6313):91-92 (1991). NASBA is a single-step isothermal RNA-specific amplification method. Generally, the method involves the following steps: RNA template is provided to a reaction mixture, where the first primer attaches to its complementary site at the 3' end of the template; reverse transcriptase synthesizes the opposite, complementary DNA strand; RNase H destroys the RNA template (RNase H only destroys RNA in RNA-DNA hybrids, but not single-stranded RNA); the second primer attaches to the 3' end of the DNA strand, and reverse transcriptase synthesizes the second strand of DNA; and T7 RNA polymerase binds double-stranded DNA and produces a complementary RNA strand which can be used again in step 1, such that the reaction is cyclic.

In other embodiments, the assay format is a flap endonuclease-based format, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In yet other embodiments, the assay format employs direct mRNA capture with branched DNA (QuantiGeneml, Panomics) or Hybrid Capture™ (Digene).

One example of an array technology suitable for use in measuring expression of the genes in an IFN-γ gene signature or measuring expression of PD-L1 is the ArrayPlate™ assay technology sold by HTG Molecular, Tucson AZ, and described in Martel, R. R., et al., Assay and Drug Development Technologies 1(1):61-71, 2002. In brief, this technology combines a nuclease protection assay with array detection. Cells in microplate wells are subjected to a nuclease protection assay. Cells are lysed in the presence of probes that bind targeted mRNA species. Upon addition of S1 nuclease, excess probes and unhybridized mRNA are degraded, so that only mRNA:probe duplexes remain. Alkaline hydrolysis destroys the mRNA component of the duplexes, leaving probes intact. After the addition of a neutralization solution, the contents of the processed cell culture plate are transferred to another ArrayPlate™ called a programmed ArrayPlate™. AffayPlates™ contain a 16-element array at the bottom of each well. Each array element comprises a position-specific anchor oligonucleotide that remains the same from one assay to the next. The binding specificity of each of the 16 anchors is modified with an oligonucleotide, called a programming linker oligonucleotide, which is complementary at one end to an anchor and at the other end to a nuclease protection probe. During a hybridization reaction, probes transferred from the culture plate are captured by immobilized programming linker. Captured probes are labeled by hybridization with a detection linker oligonucleotide, which is in turn labeled with a detection conjugate that incorporates peroxidase. The enzyme is supplied with a chemiluminescent substrate, and the enzyme-produced light is captured in a digital image. Light intensity at an array element is a measure of the amount of corresponding target mRNA present in the original cells.

By way of further example, DNA microarrays can be used to measure gene expression. In brief, a DNA microarray, also referred to as a DNA chip, is a microscopic array of DNA fragments, such as synthetic oligonucleotides, disposed in a defined pattern on a solid support, wherein they are amenable to analysis by standard hybridization methods (see Schena, BioEssays 18;427 (1996)). Exemplary microarrays and methods for their manufacture and use are set forth in T. R. Hughes et al., Nature Biotechnology 9:342-347 (2001). A number of different microarray configurations and methods for their production are known to those of skill in the art and are disclosed in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,300,637; 5,744,305; 5,770,456; 5,770,722; 5,837,832; 5,856,101; 5,874,219; 5,885,837; 5,919,523; 6,022,963; 6,077,674; and 6,156,501; Sheila, et al., Tibtech 6:301-306, 1998; Duggan, et al., Nat. Genet. 2:10-14, 1999; Bowtell, et al., Nat. Genet. 21:25-32, 1999; Lipshutz, et al., Nat. Genet. 21:20-24, 1999; Blanchard, et al., Biosensors and Bioelectronics 77:687-90, 1996; Maskos, et al., Nucleic Acids Res. 2:4663-69, 1993; and Hughes, et al., Nat. Biotechnol. 79:342-347, 2001. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference in their entireties for all purposes.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 cm$^2$ to several cm$^2$, thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In one embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well-known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed.; Elsevier, N.Y. (1993)). The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such method of detection utilizes an array scanner that is commercially available (Affymetrix, Santa Clara, CA), for example, the 417® Arrayer, the 418® Array Scanner, or the Agilent Gene Array® Scanner. This scanner is controlled from a system computer with an interface and easy-to-use software tools. The output may be directly imported into or directly read by a variety of software applications. Exemplary scanning devices are described in, for example, U.S. Pat. Nos. 5,143,854 and 5,424,186.

A preferred assay method to measure biomarker transcript abundance includes using the nCounter® Analysis Sy stem marketed by NanoString® Technologies (Seattle, Wash. USA). This system, which is described by Geiss et al., Nature Biotechnol. 2(3):317-325 (2008), utilizes a pair of probes, namely, a capture probe and a reporter probe, each comprising a 35- to 50-base sequence complementary to the transcript to be detected. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript in the sample. This system allows measuring the expression of hundreds of unique gene transcripts in a single multiplex assay using capture and reporter probes designed by Nano-String.

In measuring expression of the genes in an IFN-γ gene signature or to determine PD-L1 status described herein, the absolute expression of each of the genes in a tumor sample is compared to a control. For example, the control can be the average level of expression of each of the genes, respectively, in a pool of subjects. To increase the sensitivity of the comparison, however, the expression level values are preferably transformed in a number of ways.

For example, the expression level of each gene in the gene signature can be normalized by the average expression level of all of the genes, or the total expression level of all genes, the expression level of which is determined, or by the average expression level of a set of control genes. Thus, in one embodiment, the genes are represented by a set of probes, and the expression level of each of the genes is normalized by the mean or median expression level across all of the genes represented, including any genes that are not part of the gene signature of interest. In a specific embodiment, the normalization is carried out by dividing the median or mean level of expression of all of the genes on the microarray. In another embodiment, the expression levels of the signature genes are normalized by the mean or median level of expression of a set of control genes. In a specific embodiment, the control genes comprise housekeeping genes. In another specific embodiment, the normalization is accomplished by dividing by the median or mean expression level of the control genes.

The sensitivity of a gene signature score will also be increased if the expression levels of individual genes in the gene signature are compared to the expression of the same genes in a pool of tumor samples. Preferably, the comparison is to the mean or median expression level of each signature gene in the pool of samples. Such a comparison may be accomplished, for example, by dividing by the mean or median expression level of the pool for each of the genes from the expression level each of the genes in the subject sample of interest. This has the effect of accentuating the relative differences in expression between genes in the sample and genes in the pool as a whole, making comparisons more sensitive and more likely to produce meaningful results than the use of absolute expression levels alone. The expression level data may be transformed in any convenient way. Preferably, the expression level data for all is log transformed before means or medians are taken.

In performing comparisons to a pool, two approaches may be used. First, the expression levels of the signature genes in the sample may be compared to the expression level of those genes in the pool, where nucleic acid derived from the sample and nucleic acid derived from the pool are hybridized during the course of a single experiment. Such an approach requires that a new pool of nucleic acid be generated for each comparison or limited numbers of comparisons, and is therefore limited by the amount of nucleic acid available. Alternatively, and preferably, the expression levels in a pool, whether normalized and/or transformed or not, are stored on a computer, or on computer-readable media, to be used in comparisons to the individual expression level data from the sample (i.e., single-channel data).

When comparing a subject's tumor sample with a standard or control, the expression value of a particular gene in the sample is compared to the expression value of that gene in the standard or control. For each gene in a gene signature of the invention, the log$_{10}$ ratio is created for the expression value in the individual sample relative to the standard or control. A score for an IFN-γ gene signature or PD-L1 expression is calculated by determining the mean log(10) ratio of the genes in the signature. If the gene signature score for the test sample is above a pre-determined threshold for that gene signature, then the sample is considered to be positive for an IFN-γ gene signature biomarker. In one embodiment of the invention, the pre-determined threshold is set at any number between 2.17 and 2.69 (i.e., 2.18, 2.19, 2.20 2.66, 2.67, 2.68). The pre-determined threshold may also be the mean, median, or a percentile of scores for that gene signature in a collection of samples or a pooled sample used as a standard or control.

It will be recognized by those skilled in the art that other differential expression values, besides log(10) ratio, may be used for calculating a signature score, as long as the value represents an objective measurement of transcript abundance of the genes. Examples include, but are not limited to: xdev, error-weighted log (ratio), and mean subtracted log (intensity).

In one preferred embodiment, raw expression values are normalized by performing quantile normalization relative to the reference distribution and subsequent log 10-transformation. When the gene expression is detected using the nCounter® Analysis System marketed by NanoString®, NanoString Technologies, the reference distribution is generated by pooling reported (i.e., raw) counts for the test sample and one or more control samples (preferably at least 2 samples, more preferably at least any of 4, 8 or 16 samples) after excluding values for technical (both positive and negative control) probes and without performing intermediate normalization relying on negative (background-adjusted) or positive (synthetic sequences spiked with known titrations). The IFN-γ signature score is then calculated as the arithmetic mean of normalized values for each of the genes in the gene signature, e.g., one or any combination of STAT1, CCR5, CXCL9, PRF1, and HLA-DRA or each of IFNγ, STAT1 CCR5, CXCL9, PRF1, HLA-DRA, CXCL10, CXCL11, ID01 and GZMA, or of PD-L1.

In some preferred embodiments, the reference distribution is generated from raw expression counts for a normalization set of genes, which consists essentially of each of the genes in the set of 400 genes listed in FIG. 11, or a subset thereof. The subset may consist of at least any of 25, 50 75, 100, 125, 150, 175, 200, 225, 250, 275, 300, 325, 350, 375 or any whole number in between 25 and 400.

Each of the steps of obtaining a tissue sample, preparing one or more tissue sections therefrom for a gene signature biomarker assay, performing the assay, and scoring the results may be performed by separate individuals/entities at separate locations. For example, a surgeon may obtain by biopsy a tissue sample from a cancer patient's tumor and then send the tissue sample to a pathology lab, which may fix the tissue sample and then prepare one or more slides, each with a single tissue section, for the assay. The slide(s) may be assayed soon after preparation, or stored for future assay. The lab that prepared a tissue section may conduct the assay or send the slide(s) to a different lab to conduct the assay. A pathologist or trained professional who scores the slide(s) for an IFN-γ gene signature may work for the diagnostic lab, or may be an independent contractor. Alternatively, a single diagnostic lab obtains the tissue sample from the subject's physician or surgeon and then performing all of the steps involved in preparing tissue sections, assaying the slide(s) and calculating the gene signature score for the tissue section(s).

In some embodiments, the individuals involved with preparing and assaying the tissue section for a gene signature biomarker do not know the identity of the subject whose sample is being tested; i.e., the sample received by the laboratory is made anonymous in some manner before being sent to the laboratory. For example, the sample may be merely identified by a number or some other code (a "sample ID") and the results of the assay are reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may comprise any one or both of the following results: the tissue sample was biomarker positive or negative, the gene signature score for the tumor sample and the reference score for that gene signature. The test report may also include a list of genes whose expression was analyzed in the assay.

In other embodiments, the test report may also include guidance on how to interpret the results for predicting if a subject is likely to respond to a pembrolizumab, pembrolizumab variant and/or antigen-binding fragment thereof/tatimogene laherparepvec combination therapy. For example, in one embodiment, the tested tumor sample is from a cancer including, but not limited to, melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g HER2+, HER2− (HR+), triple-negative), ovarian cancer, bladder cancer transitional cell cancer, urothelial cancer), prostate cancer castration-resistant), sarcoma (e.g., soft tissue, bone), renal cell cancer, gastric cancer, esophageal cancer, anal canal cancer, biliary tract cancer or pancreatic cancer and has a negative IFN-γ gene signature score and/or a low or negative PD-L1 status score, the test report may indicate that the subject has a score that is associated with response or better response to treatment with a pembrolizumab, pembrolizumab variant and/or antigen-binding fragment thereof/talimogene laherparepvec combination therapy, while if the CD8+ T-cell density score and/or IFN-γ gene signature scores are above the threshold, and/or PD-L1 status score is high, then the test report indicates that the patient has a score that is associated with no response or poor response to treatment with a pembrolizumab pembrolizumab variant and/or antigen-binding fragment thereof/talimogene laherparepvec combination therapy.

In another embodiment, the tested tumor sample is from a cancer that is responsive to monotherapy with a checkpoint inhibitor (e.g., with anti-PD-L1 therapy or anti-PD-1 therapy (e.g., pembrolizumab, a pembrolizumab variant or an antigen-binding fragment thereof)), which may optionally be associated with one or more of a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample), a low or negative PD-L1 status and a negative IFNγ gene signature, including, but not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g., ER+/HER2− breast cancer, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Detecting the presence or absence of a marker of the invention may be performed using a kit that has been specially designed for this purpose. In one embodiment, the kit comprises a set of oligonucleotide probes capable of hybridizing to the target transcripts in the gene signature. The kit may further comprise oligonucleotide probes capable of detecting transcripts of other genes, such as control genes, or genes used for normalization purposes. The set of oligonucleotide probes may comprise an ordered array of oligonucleotides on a solid surface, such as a microchip, silica beads (such as BeadArray technology from Illumina, San Diego, Calif.), or a glass slide (see, e.g., WO 98/20020 and WO 98/20019). In some embodiments, the oligonucleotide probes are provided in one or more compositions in liquid or dried form.

Immunohistochemistry (IHC)

An IHC assay typically begins with antigen retrieval, which may vary in terms of reagents and methods. The antigen retrieval process may involve pressure cooking, protease treatment, microwaving, or heating histologic sections in baths of appropriate buffers, with the standard goal of unmasking antigens hidden by formalin crosslinks or other fixation. (See, e.g., Leong et al. Appl. Immnunohistochem. 4(3):201 (1996).)

Two general methods of IHC may be used: direct and indirect assays. In a direct IHC assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody Used for immunohistochemistry typically will be labeled with a detectable moiety. Numerous labels are available which can be generally grouped into the following categories: (a) Radioisotopes, such as $^{35}S$, $^{14}C$, $^{131}I$, $^{3}H$, and $^{123}I$ (The antibody can be labeled with the radioisotope using the techniques described in Current Protocols in Immunology, Volumes 1 and 2, Coligen et al, Ed. Wiley-interscience, New York, N.Y., Pubs. (1991) for example and radioactivity can be measured using scintillation counting. Other radionuclides include $^{99}Tc$, $^{90}Y$, $^{32}P$, $^{13}N$, $^{18}F$, $^{51}Cr$, $^{57}To$, $^{225}Ra$, $^{60}Co$, $^{59}Fe$, $^{57}Se$, $^{152}Eu$, $^{67}Cu$, $^{217}Ci$, $^{211}At$, $^{212}Pb$, $^{47}Sc$, $^{109}Pd$, $^{234}Th$, $^{40}K$, $^{157}Gd$, $^{55}Mn$, $^{52}Tr$, $^{82}Rb$, $^{201}Th$, $^{92}Sr$, $^{67}Ga$, $^{192}Ir$, $^{166}Ho$, $^{10}B$, $^{99m}Tc$, $^{42}K$, $^{186}Re$, $^{188}Re$, $^{75}Se$, $^{24}Na$, $^{11}C$, $^{13}N$, $^{15}O$, $^{57}Co$, $^{67}Ga$, $^{177}Lu$ and $^{55}Fe$); Colloidal gold particles; and fluorescent or chemiluminescent labels including, but not limited to, rare earth chelates (europium chelates), fluorescein and its derivatives, rhodamine and its derivatives, isothiocyanate, phycoerythrin, phycocyanin, allophycocyanin, o-phthaladehyde, fluorescamine, dansyl, umbelliferone, luciferin, label, isoluminal label, an aromatic acridinium ester label, an imidazole label, an acridimium salt label, an oxalate ester label, an aequorin label, 2,3-dihydrophthalazinediones, Texas Red, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in Current Protocols in Immunology, Supra, for example. Fluorescence can be quantified using a fluorimeter.

Various enzyme-substrate labels are available (See U.S. Pat. No. 4,275,149). The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor.

Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, Methods for the Preparation of Enzyme-Antibody Conjugates for use in Enzyme Immunoassay, in Methods in Enzym. (ed J. Langbne & H. Van Vunakis), Academic press, New York, 73;147-166 (1981).

Numerous enzyme-substrate combinations are available to those skilled in the art. For a general review of these, see U.S. Pat. Nos. 4,275,149 and 4,318,980. Examples of enzyme-substrate combinations are: (i) Horseradish peroxidase (HRP) with hydrogen peroxidase as a substrate, wherein the hydrogen peroxidase oxidizes a dye precursor, such as, e.g., 3,3' diamino benzidine (DAB), which produces a brown end product; 3-amino-9-ethylcarbazole (AEC), which upon oxidation forms a rose-red end product; 4-chloro-1-naphthol (CN), which precipitates as a blue end product; and p-Phenylenediamine dihydrochloride/pyrocatecol, which generates a blue-black product; orthophenylene diamine (OPD) and 3,3',5,5'-tetramethyl benzidine hydrochloride (TMB); (ii) alkaline phosphatase (AP) and para-Nitrophenyl phosphate, naphthol AS-MX phosphate, Fast Red TR and Fast Blue BB, naphthol AS-BI phosphate, naphthol AS-TR phosphate, 5-bromo-4-chloro-3-indoxyl phosphate (BCIP), Fast Red LB, Fast Garnet GBC, Nitro Blue Tetrazolium (NBT), and iodonitrotetrazotium violet (INT); and (iii) β-D-galactosidase (β-D-Gal) with a chromogenic substrate (e.g., p-nitrophenyl-P-D-galactosidase) or fluorogenic substrate (e.g., 4-methylumbelliferyl-P-D-galactosidase).

Any method known in the art for conjugating the antibody molecules to the various moieties may be employed, including those methods described by Hunter, et al, (1962) Nature 144:945; David, et al, (1974) Biochemistry 13: 1014; Pain, et al, (1981) J. Immunol. Meth. 40:219; and Nygren, J., (1982) Histochem. and Cytochem. 30:407.

In some embodiments, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

After antigen retrieval and an optional blocking step, the tissue section is exposed to pembrolizumab, a pembrolizumab variant and/or an antigen-binding fragment thereof as the primary antibody for a sufficient period of time and under suitable conditions to allow the primary antibody to bind to the PD-L1 protein in the tissue section. Appropriate conditions for achieving this can be determined by routine experimentation. The slide is then washed to remove unbound and excess amounts of the primary antibody.

In some embodiments, the primary antibody is linked to a detectable label, such as paramagnetic ions, radioactive isotopes, fluorochromes, and the like, and the slide is evaluated for PD-L1 staining using the appropriate imaging apparatus.

In other embodiments, immune complexes between PD-L1 and the primary antibody may be detected using a second binding agent that is linked to a detectable label. The second binding agent is preferably a secondary antibody, which is applied to the slide at a concentration and for a period of time sufficient to allow the formation of secondary immune complexes. The slide is then typically washed to remove any non-specifically bound secondary antibody, and the label in the secondary immune complexes is detected.

The secondary antibody may be labeled using avidin, streptavidin or biotin, which is independently labeled with a detectable moiety, such as a fluorescent dye (stain), a luminescent dye or a non-fluorescent dye. In principle, any enzyme that can be conjugated to or can bind indirectly to the secondary antibody (e.g., via conjugated avidin, streptavidin, biotin) could be used. The enzyme employed can be, for example, alkaline phosphatase (AP), horseradish peroxidase (HRP), beta-galactosidase and/or glucose oxidase. The enzyme can also be directed at catalyzing a luminescence reaction of a substrate, such as, but not limited to, luciferase and aequorin, having a substantially non-soluble reaction product capable of luminescing or of directing a second reaction of a second substrate, such as but not limited to, luciferin and ATP or coelenterazine and $Ca^{2+}$, having a luminescing product. Finally, a detection reagent is applied that includes a chromagen or a fluorescently tagged molecule to visualize the localization of the immune complexes.

The IHC assay may be performed using an automated pathology system, which may include automated staining (conventional stains, histochemical techniques, immunostainers); automated in situ hybridization systems; automatic slide preparation (coverslip, slide drying) and integrated slide and cassette labeling, as described in Roja et al., Review of imaging solutions for integrated, quantitative immunohistochemistry in the Pathology daily practice, Folia Histochemica et Cytobiologica, Vol. 47, No. 3, 349-354, 2009.

In certain exemplary embodiments, an IHC assay employs the commercially available Dako EnVision™ FLEX detection system, which is intended for use together with a Dako Autostainer instrument (Dako, an Agilent Technologies Company, Glostrup, Denmark). These reagents can be used off the shelf for other autostainers or for manually-performed staining (not performed with an autostainer), Sample Collection and Preparation of Tissue Sections A tumor tissue sample used to prepare stained tissue sections for scoring PD-L1 expression can be collected from a subject before and/or after exposure of the subject to one or more therapeutic agents, e.g. a pembrolizumab, pembrolizumab variant and/or antigen-binding fragment thereof, tatimogene laherparepvec and/or a chemotherapeutic agent. Accordingly, tumor samples may be collected from a subject over a period of time. The tumor sample can be obtained by a variety of procedures including, but not limited to, surgical excision, aspiration or biopsy. The tissue sample may be sectioned and examined for PD-L1 as a fresh specimen. In other embodiments, the tissue sample is frozen for further sectioning, in other embodiments, the tissue sample is preserved by fixing and embedding in paraffin or the like.

The tissue sample may be fixed by conventional methodology, with the length of fixation depending on the size of the tissue sample and the fixative used. Neutral buffered formalin, glutaraldehyde, Bouin's or paraformaldehyde are non-limiting examples of fixatives. In preferred embodiments, the tissue sample is fixed with formalin. In some embodiments, the fixed tissue sample is also embedded in paraffin to prepare a formalin-fixed and paraffin-embedded (FFPE) tissue sample. Examples of paraffin include, but are not limited, to, Paraplast, Broloid and Tissuemay.

Typically, the tissue sample is fixed and dehydrated through an ascending series of alcohols, infiltrated and embedded with paraffin or other sectioning media so that the tissue sample may be sectioned. Alternatively, the tumor tissue sample is first sectioned and then the individual sections are fixed.

In some embodiments, the scoring process of the invention is performed on FFPE tissue sections of about 3-4 millimeters, and preferably 4 micrometers, which are mounted and dried on a microscope slide.

Pembrolizumab and Pembrolizub Variant Antibodies

The primary antibody for an IHC assay described herein is pembrolizumab, a pembrolizumab variant and/or an antigen-binding fragment thereof, which binds to the mature form of PD-L1 (lacking the pre-secretory leader sequence, also referred to as leader peptide) that is expressed on the surface of certain mammalian cells. The terms "PD-L1" and "mature PD-L1" are used interchangeably herein, and shall be understood to mean the same molecule unless otherwise indicated or readily apparent from the context. As used herein, an anti-human PD-L1 antibody or an anti-hPD-L1 antibody refers to an antibody that specifically binds to mature human PD-L1, e.g., pembrolizumab, a pembrolizumab variant and/or an antigen-binding fragment thereof.

A mature human PD-L1 molecule consists of amino acids 19-290 of the following sequence:

(SEQ ID NO: 11)
MRIFAVFIFMTYWHLLNAFTVTVPKDLYVVEYGSNMTIECKFPVEKQLDLA

ALIVYWEMEDKNIIQFVHGEEDLKVQHSSYRQRARLLKDQLSLGNAALQIT

DVKLQDAGVYRCMISYGGADYKRITVKVNAPYNKINQRILVVDPVTSEHEL

TCQAEGYPKAEVIWTSSDHQVLSGKTTTTNSKREEKLFNVTSTLRINTTTN

EIFYCTFRRLDPEENHTAELVIPELPLAHPPNERTHLVILGAILLCLGVAL

TFIFRLRKGRMMDVKKCGIQDTNSKKQSDTHLEET.

An antibody that "specifically binds to human PD-L1," or an antibody that "specifically binds to a polypeptide comprising the amino acid sequence of human PD-L1," is an antibody that exhibits preferential binding to human PD-L1 as compared to other antigens, but this specificity does not require absolute binding specificity. An anti-hPD-L1 antibody is considered "specific" for human PD-L1 if its binding is determinative of the presence of human PD-L1 in a sample, e.g. without producing undesired results such as false positives in an IHC diagnostic assay. Antibodies, or binding fragments thereof, useful as a primary antibody in the processes and methods of the present invention will bind to human PD-L1 with an affinity that is at least two fold greater, preferably at least ten times greater, more preferably at least 20-times greater, and most preferably at least 100-times greater than the affinity with any non-PD-L1 protein. As used herein, an antibody is said to bind specifically to a polypeptide comprising a given sequence, e.g. mature human PD-L1, if it binds to polypeptides comprising that sequence but does not bind to proteins lacking that sequence. Tissue sections of tumor samples from human subjects may be scored for PD-L1 expression using pembrolizumab, a pembrolizumab variant and/or an antigen-binding fragment thereof.

Diagnostic Testing for PD-L1 Expression

In one embodiment, the tested tumor sample is from a cancer that is associated with a low or negative PD-L1 status, and optionally a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 mL sample) and/or a low or negative PD-L1 status, and is from melanoma (e.g., cutaneous, metastatic, uveal), non-small cell lung cancer, head and neck cancer (e.g., recurrent or metastatic squamous cell carcinoma of the head and neck), colorectal cancer, breast cancer (e.g., HER2+, HER2– (HR+), triple-negative), ovarian cancer, bladder cancer transitional cell cancer, urothelial cancer), prostate cancer (e.g., castration-resistant), sarcoma (e.g., soft tissue, bone), renal cell cancer, gastric cancer, esophageal cancer, anal canal cancer, biliary tract cancer or pancreatic cancer.

In another embodiment, be tested tumor sample is responsive to monotherapy with a checkpoint inhibitor (e.g., with anti-PD-L1 therapy or anti-PD-1 therapy pembrolizumab, a pembrolizumab variant or an antigen-binding fragment thereof)), and may optionally be associated with one or more of a CD8+ T-cell infiltration density of fewer than about 1500, about 1400, about 1300, about 1200, about 1100, about 1000, about 900, about 800, about 700, about 600, or about 500 cells per 1 mm$^2$ sample (or per 1 ml, sample), a low or negative PD-L1 status and a negative IFNγ gene signature, including, but not limited to, melanoma (e.g., cutaneous, metastatic, uveal), lung cancer (e.g., non-small cell lung cancer, small cell lung cancer), head and neck cancer (e.g., recurrent or metastatic squamous cell carcinoma of the head and neck, nasopharyngeal cancer, thyroid cancer, salivary cancer, esophageal cancer), breast cancer (e.g., ER+/HER2– breast cancer, triple-negative breast cancer), ovarian cancer, cervical cancer, bladder cancer (ex., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma.

Each of the steps of obtaining a tissue sample, preparing one or more tissue sections therefrom for IHC assay, performing the IHC staining, and scoring the results may be performed by separate individuals/entities at the same or separate locations. For example, a surgeon may obtain by biopsy a tissue sample from a cancer patient's tumor and then send the tissue sample to a pathology lab, which may fix the tissue sample and then prepare one or more slides, each with a single tissue section, for IHC assay. The slide(s) may be analyzed by IHC soon after preparation, or stored for future assay. The lab that prepared a tissue section for IHC assay may conduct the assay or send the slide(s) to a different lab to conduct the assay. A pathologist or trained professional who scores the stained slide(s) for PD-L1 staining may work for the diagnostic lab, or may be an independent contractor. Alternatively, a single diagnostic lab obtains the tissue sample from the subject's physician or surgeon and then performs all of the steps involved in preparing tissue sections, staining the slide(s) and scoring PD-L1 expression in the stained tissue section(s) or sending the stained slide(s) to a trained professional for PD-L1 scoring.

In some embodiments, the individuals involved with preparing and analyzing the tissue section by IHC assay do not know the identity of the subject whose sample is being tested, i.e., the sample received by the laboratory is made anonymous in some manner before being sent to the laboratory. For example, the sample may be merely identified by a number or some other code (a "sample ID") and the results of the IHC assay is reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may include a result that the tissue sample was positive or negative for PD-L1 expression. The test report may also include guidance on how to interpret the results for predicting if a subject is likely to respond to a pembrolizumab, pembrolizumab variant and/or antigen-binding fragment thereof/talimogene laherparepvec combination therapy. For example, in one embodiment, if the patient's tumor is below a pre-specified threshold, the test report may indicate that the patient has a PD-L1 expression score that is correlated with response or better response to treatment with pembrolizumab, pembrolizumab variant and/or antigen-binding fragment thereof/talimogene laherparepvec combination therapy, while if the PD-L1 expression score is at or above a pre-specified threshold, the PD-L1 expression score is correlated with no response or poor response to treatment with pembrolizumab, pembrolizumab variant and/or antigen-binding fragment thereof/talimogene laherparepvec combination therapy.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Methods to Quantify Lymphocytes

Flow Cytometry

Lymphocyte subsets are typically measured by immunofluorescent labeling of culls with fluorochromes conjugated to specific monoclonal antibodies and quantifying the proportion of specifically labeled cells by flow cytometry. Manual alternatives to flow cytometry are also available to quantify CD4 cells. They are simple light or fluorescence microscopy methods that just require cell counting.

In flow cytometry, specific monoclonal antibodies made against the specific CD antigens present on the cells are labeled with fluorescent dyes. The labeled monoclonal antibodies are allowed to react with the mononuclear cells (lymphocytes and monocytes), and the cells that react can be classified by the flow cytometer into subpopulations depending on which antibodies are bound. Flow cytometry generally gives the percentage of CD4+ or CD8+ cells. To obtain absolute cell counts, dual and single platform technologies are used. A dual platform technology employs a flow cytometer and a hematology analyzer. CD4 absolute count using dual platform approach is a product of three measurements: the white blood cell count, the percentage of white blood cells counts that are lymphocytes (differential), and the percentage of lymphocytes that are CD4 cells (determined by flow cytometry). If a single platform technology is used, absolute counts of lymphocyte subsets are measured in a single tube by a single instrument. Usually it is accomplished by spiking a fixed volume of sample with a known number of fluorescent beads (bead-based systems) or by precisely recording the volume of the sample analyzed. Recent recommendations suggest that single platform technology should be the gold standard for the CD4 absolute count.

Several varieties of flow cytometers are available, with the FACSCalibur (Becton Dickinson) and EPICS XL (Beckman Coulter) being the most popular. These instruments offer high sample throughput, workflow management through automation, and simple software applications. Both instruments can detect four colors and measure relative cell size and cellular complexity. The systems are designed to use whole blood, collected in liquid EDTA. Besides using the traditional flow cytometers (open platforms that can employ dual or single platform technology), the simplified dedicated platforms are developed for CD4+ T-cell counts. The commercially available dedicated platforms include FACScount (Becton Dickinson), CyFLow Counter (Partec), and Guava: uto CD4/CD8% (Millipore/Merck). The dedicated platforms allow CD4+ T-cell counting with reduced technical complexity, producing absolute CD4 counts and a CD4/CD8 ratio without requiring an external computer. The system uses whole blood, eliminates the need for lysis and wash steps, and has a unique software algorithm that automatically identifies the lymphocyte populations of interests.

Manual Methods to Quantity Lymphocytes

Manual alternatives to flow cytometry available on the market are: the Cyto-Spheres (Coulter Corporation, USA) and the Dynabeads (Dynal AS, Norway). The Dynal T4 kit (the Dynabeads) is used to manually count CD4 cells in a cell counting chamber under a microscope. This method measures CD4 absolute count; no lymphocyte percentages can be determined. It requires an epifluorescent microscope (recommended), although it can be performed with only a light microscope; a hemocytometer, a vortex, a tube rocker, a timer, and a magnet. Magnetic beads are coated with monoclonal antibodies as a solid phase to isolate CD4 and CD8 cells from whole blood, whereas CD4-positive monocytes are pre-depleted using CD14 magnetic beads. After isolation of CD4 cells, the cells are lysed, stained, and counted. Blood samples should be fresh, preferably not older than 24 hours. The Coulter Manual CD4 Count Kit (for the Cyto-Spheres method) requires a light microscope, timer, and a hemocytometer and measures CD4 absolute counts (no percentages) from whole blood collected in EDTA tubes. Antibody-coated latex particles are used to bind CD4 cells resulting in a "rosette" of latex beads around each CD4 cell; the rosette is readily recognized by light microscopy. A monocyte blocking reagent minimizes the interference from monocytes that contain CD4 antigens because they can be recognized during CD4 cell counting.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

Diagnostic Testing for CD8+ Expression

In one embodiment, the tested tumor sample is from a cancer associated with a CD8+ infiltration density of fewer than about 1500, about 1400, about 1300, about 1200, about 1100, about 1000, about 900, about 800, about 700, about 600, or about 500 cells per 1 mm$^2$ sample (or per 1 mL sample), optionally having a low or negative PD-L1 status and/or a negative IFNγ gene signature, including, but not limited to, melanoma (e.g., cutaneous, metastatic, uveal), non-small cell lung cancer, head and neck cancer recurrent or metastatic squamous cell carcinoma of the head and neck), colorectal cancer, breast cancer (e.g., HER2+, HER2− (HR+), triple-negative), ovarian cancer, bladder cancer (e.g., transitional cell cancer, urothelial cancer), prostate cancer (e.g., castration-resistant), sarcoma (e.g., soft tissue, bone renal cell cancer, gastric cancer, esophageal cancer, anal canal cancer, biliary tract cancer or pancreatic cancer.

In one embodiment, the tested tumor sample is from a cancer that is responsive to monotherapy with a checkpoint inhibitor (e.g., with anti-PD-L1 therapy or anti-PD-1 therapy (e.g., pembrolizumab, a pembrolizumab variant or an antigen-binding fragment thereof)), which may optionally be associated with one or more of a CD8+ T-cell infiltration density of fewer than about 1500, about 1400, about 1300, about 1200, about 1100, about 1000, about 900, about 800, about 700 about 600, or about 500 cells per 1 mm$^2$ sample (or per 1 mL sample), a low or negative PD-L1 status and a negative IFNγ gene signature, including, but not limited to, melanoma (e.g., cutaneous, metastatic, uveal), lung cancer (e.g., non-small cell lung cancer, small cell lung cancer), head and neck cancer (e.g., recurrent or metastatic squatrious cell carcinoma of the head and neck, nasopharyngeal cancer, thyroid cancer, salivary cancer, esophageal cancer), breast cancer (e.g. ER+/HER2− breast cancer, triple-negative breast cancer), ovarian cancer, cervical cancer, bladder cancer (e.g., urothelial cancer), renal cell cancer, gastrointestinal cancer (e.g., hepatocellular cancer, colorectal cancer, anal cancer), biliary tract cancer, multiple myeloma, lymphoma (e.g., mediastinal large B-cell lymphoma, Hodgkin's lymphoma) or mesothelioma.

Each of the steps of obtaining a sample, preparing the sample for flow cytometry, performing flow cytometry, and scoring the results may be performed by separate individuals/entities at the same or separate locations. For example, a surgeon may obtain by biopsy a sample from a cancer patient and then send the sample to a pathology lab, which may prepare the sample for flow cytometry. The slide(s) may be analyzed by IHC soon after preparation, or stored for future assay. The lab that prepared a sample for flow cytometry may conduct the assay or send the slide(s) to a different lab to conduct the assay. A pathologist or trained professional who performs flow cytometry may work for the diagnostic lab, or may be an independent contractor. Alternatively, a single diagnostic lab obtains the sample from the subject's physician or surgeon and then performs all of the steps involved in preparing the sample and scoring CD8+ in the sample or sending the sample to a trained professional for CD8+ scoring.

In some embodiments, the individuals involved with preparing and analyzing the sample by flow cytometry do not know the identity of the subject whose sample is being tested, i.e., the sample received by the laboratory is made anonymous in some manner before being sent to the laboratory. For example, the sample may be merely identified by a number or some other code (a "sample ID") and the results of the flow cytometry assay are reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may include guidance on how to interpret the results for predicting if a subject is likely to respond to pembrolizumab, pembrolizumab variant and/or antigen-binding fragment thereof/talimogene laherparepvec combination therapy. For example, in one embodiment, if the patient's tumor is below a pre-specified threshold, the test report may indicate that the patient has a CD8+ expression score that is correlated with response or better response to treatment with pembrolizumab, pembrolizumab variant and/or antigen-binding fragment thereof/talimogene laherparepvec combination therapy, while if the CD8+ expression score is at or above a pre-specified threshold, the CD8+ expression score is correlated with no response or poor response to treatment with pembrolizumab, pembrolizumab variant and/or antigen-binding fragment thereof/talimogene laherparepvec combination therapy.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting. All patents, patent applications and references described herein are incorporated by reference in their entireties for all purposes.

EXAMPLES

Example 1. Phase 1b Clinical Trial Combining Talimogene Laherparepvec with Pembrolizumab A phase 1b trial (MASTERKEY-265; ClinicalTrials.gov Identifier: NCT02263508) was designed in patients with advanced melanoma combining the intratumoral injection of talimogene laherparepvec with the systemic administration of the anti-PD-1 antibody pembrolizumab, with baseline and repeated on-therapy biopsies, with the primary objective of testing the safety of this combination, and to explore its ability to boost inflammatory status of tumors.

Eligible patients (≥18 years) had histologically confirmed, surgically unresectable, stage IIIB-IV cutaneous melanoma, measurable disease (≥1 melanoma lesion with longest diameter ≥10 mm), and ≥1 injectable cutaneous, subcutaneous, or nodal melanoma lesion(s) that were ≥10 mm in longest diameter, either alone or in aggregate, for whom surgery was not recommended. Patients were required to have adequate performance status and hematologic, hepatic, renal, and coagulation function. Patients were excluded if they had uveal/mucosal melanoma; had been previously treated for advanced melanoma with systemic therapy, previously received talimogene laherparepvec or any prior systemic anticancer treatment for unresectable, stage IIIB-IV melanoma; Eastern Cooperative Oncology Group (ECOG) performance status ≥2; active brain metastases; active herpetic skin lesions; prior complications from herpetic infection; or required systemic anti-herpetic treatment other than intermittent topical use. All patients provided written informed consent. Study procedures were approved by an institutional ethics committee at each site.

Study Design

Figure 6A:
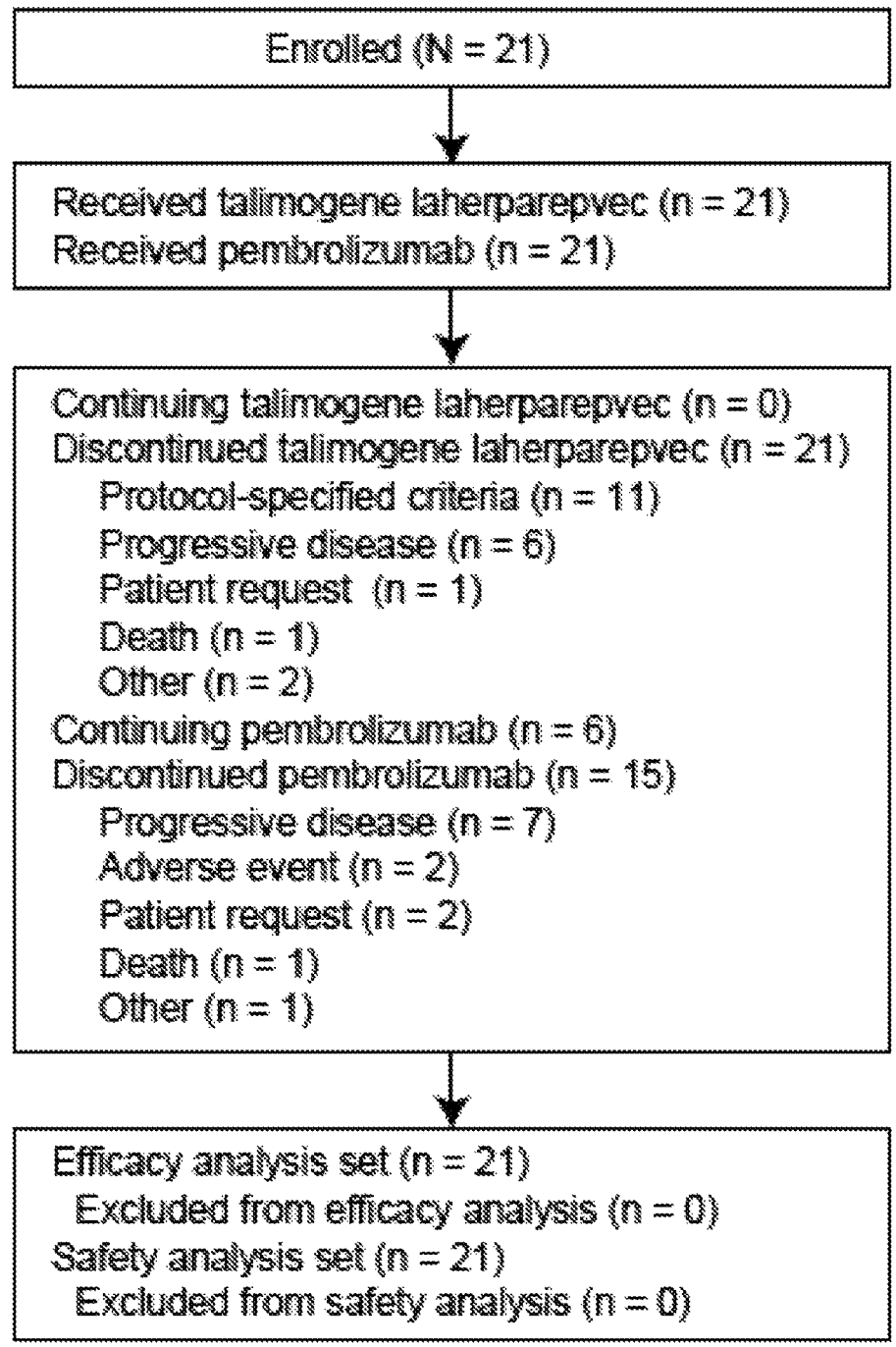
FIG. 6 depicts the disposition of patients enrolled in the study and biopsy availability for biomarker testing.
Figure 7A:
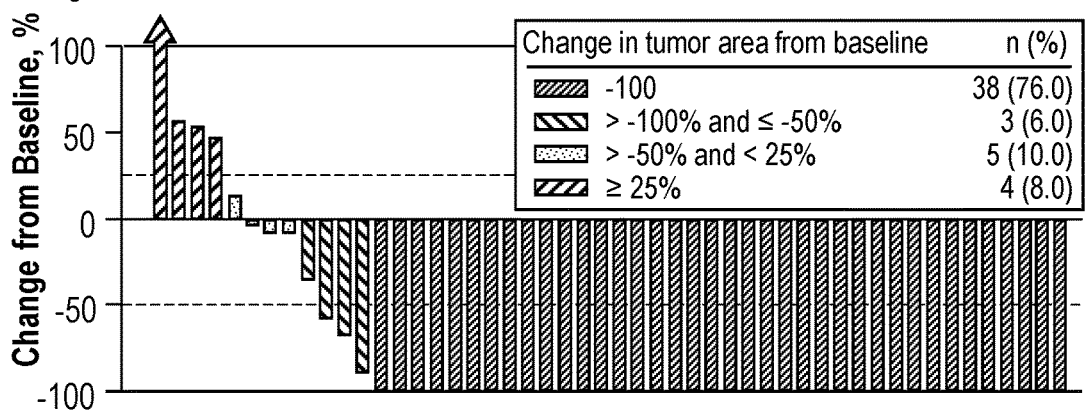
FIG. 7 depicts changes in tumor burden at the lesion level. (A) Depicts injected lesion response. (B) Depicts non-injected, non-visceral lesion response. (C) Depicts non-injected, visceral lesion response.
Figure 7B:
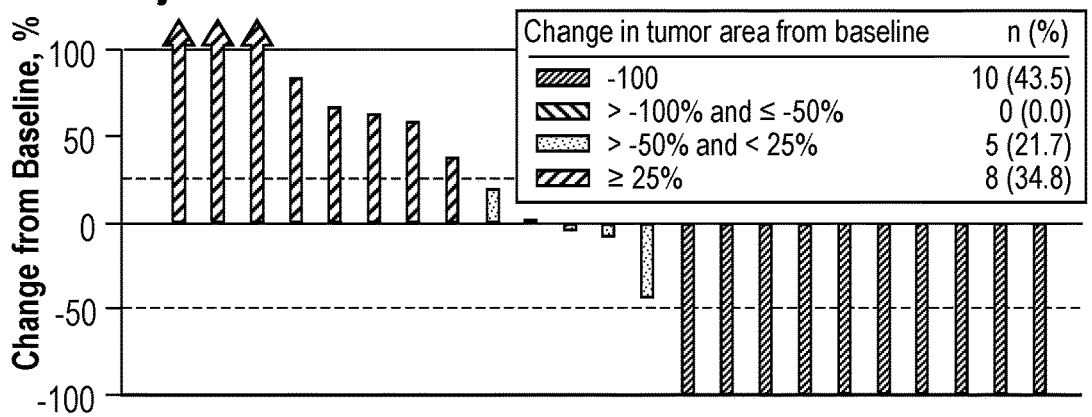
Figure 7C:
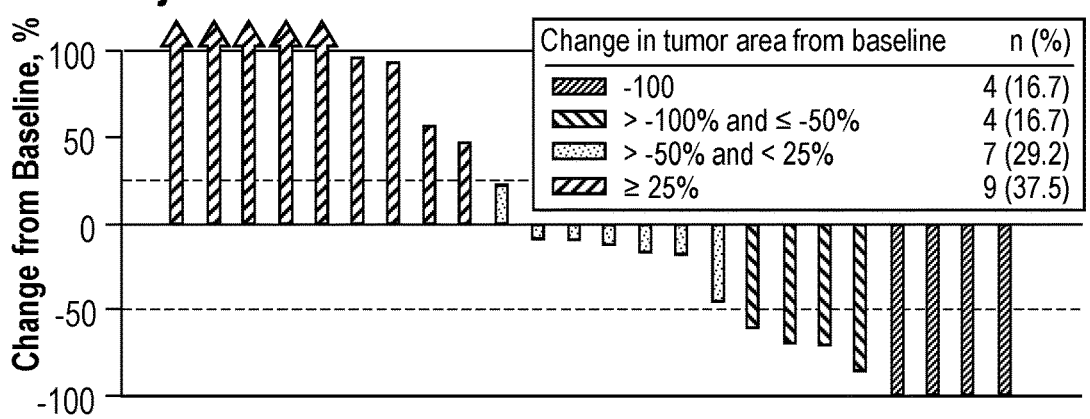

The phase 1b portion of the MASTERKEY-265 study was an open-label, multicenter, single-arm study that primarily evaluated the safety of intralesional talimogene laherparepvec in combination with intravenous pembrolizumab (FIG. 6).

Briefly, to seroconvert herpes simplex virus-negative patients, intralesional talimogene laherparepvec $10^6$ pfu/mL was administered on day 1 of study week 1. Subsequent doses of talimogene laherparepvec $10^8$ pfu/mL were administered on day 1 of weeks 4 and 6, and every 2 weeks thereafter. Up to 4 mL (total volume) of talimogene laherparepvec could be administered by intralesional injection at each treatment visit. The volume delivered to each injected lesion was contingent on the diameter of the lesion (Haffner, B., Iodice, G. M., and Gasai, E. (2016). Administration and Handling of Talimogene Laherparepvec: An Intralesional Oncolytic immunotherapy for Melanoma. Oncol Nurs Forum 43, 219-226). The injected volume per lesion ranged from 0.1 mL for lesions ≤0.5 cm to 4.0 mL for lesions >5 cm in longest diameter. Talimogene laherparepvec administration continued until disappearance of injectable lesions, complete response (CR), confirmed disease progression (PD) per modified immune-related response criteria (irRC), (Wolchok et al., 2009) treatment intolerance, 24 months from the first dose of pembrolizumab, or end of study, whichever occurred first. If toxicity occurred, talimogene laherparepvec doses could be delayed for up to 4 weeks; delays >4 weeks resulted in permanent discontinuation.

Pembrolizumab (200 mg) was administered intravenously every 2 weeks beginning on day 1 of week 6 (i.e., at the time of third dose of talimogene laherparepvec). Pembrolizumab treatment was to be continued until confirmed PD by irRC, treatment intolerance, 2.4 months from the first dose of pembrolizumab, or the end of study, whichever occurred first. Pembrolizumab could be withheld or discontinued per protocol-specified rules consistent with the US prescribing information (Kaufman, H. L., Kim, D. W., DeRaffele, G., Mitcham, J., Coffin, R. S., and Kim-Schulze, S. (2010). Local and distant immunity induced by intralesional vaccination with an oncolytic herpes virus encoding GM-CSF in patients with stage IIIc and IV melanoma. Ann Surg Oncol 17, 718-730). If pembrolizumab was withheld >12 weeks, pembrolizumab treatment was permanently discontinued.

The primary endpoint was incidence of dose limiting toxicities (DLTs) starting from when both agents were given in combination. Incidence of DLTs in the first 6 DLT-evaluable patients and additional safety data from all patients were evaluated by a dose-level review team. The combination would be declared tolerable if the incidence of DLTs was <33% during the DLT evaluation period. Secondary endpoints included confirmed objective response rate (ORR; the rate of CR plus partial response (PR)) as evaluated by investigators per irRC, (Wolchok et al., 2009) best overall response, and incidence of AEs.

DLTs were defined as any of the following treatment-related toxicities occurring during the 6-week period from the beginning of pembrolizumab treatment: grade 4 non-hematologic toxicity; grade ¾ pneumonitis; grade 3 non-hematologic toxicity lasting >3 days despite optimal supportive care (except grade 3 fatigue); grade ¾ non-hematologic laboratory value requiring medical intervention hospitalization or persisting >1 week; grade ¾ febrile neutropenia; thrombocytopenia <25×109/L if associated with a life-threatening bleeding event or bleeding event requiring platelet infusion; any grade 5 toxicity; or any toxicity requiring permanent discontinuation of talimogene laherparepvec or pembrolizumab.

Study Clinical Assessments

Adverse events occurring from week 1 to 30 days after the last dose of study treatment were recorded and graded using Common Terminology Criteria for Adverse Events version 4.0.

Tumor response was evaluated per modified irRC (Wolchok, J. D., Hoos, A., O'Day, S., Weber, J. S., Hamid, O., Lebbe, C., Maio, M., Binder, M., Bohnsack, O., Nichol, G., et al. (2009). Guidelines for the evaluation of immune therapy activity in solid tumors: immune-related response criteria. Clin Cancer Res 15, 7412-7420) by investigators. Complete response was defined as the disappearance of all lesions; PR was defined as a decrease in tumor area ≥50% relative to baseline; PD was defined as an increase in tumor area ≥25% relative to nadir; and SD was defined as any outcome not meeting the criteria for response or PD with ≥77 days elapsed after enrollment. Responses were confirmed within 4 weeks from the date of first documentation of response. Tumor assessments were performed at screening, week 6 (prior to initiation of pembrolizumab), week 18, and every 12 weeks thereafter. Radiographic imaging for assessment of lesions was performed using computed tomography, positron emission tomography, magnetic resonance imaging, or ultrasound. Clinical measurement of cutaneous, subcutaneous, and palpable nodal tumor lesions was conducted with calipers. Initial measurement of PD was confirmed by assessment of measureable/non-measureable new lesions as well as index lesions ≥4 weeks later. If clinically stable, patients continued treatment while awaiting confirmation of PD.

Biomarker Analysis

Flow Cytometry

T-cell subsets were analyzed by flow cytometry with the following markers CD45, CD3, CD4, CD8, and BD Tru-COUNT. Additionally, checkpoint markers assessed included HLA-DR, PD-1, Tim3, BMA, ICOS, OX40, 41BB, and GITR on T-cell subsets as defined by expression of CD3, CD4, CD8, CCR7 and CD45RA.

RNA Profiling and IFNγ Gene Signature

Total RNA was isolated from 5 μm think formalin-fixed paraffin-embedded (FFPE) sections fixed on positively charged slides. Percentage tumor area was first assessed and either all tissue was scraped for isolation or if <50% tumor area was present, tumor tissue was macro-dissected for isolation. RNA isolation was performed using the High Pure FFPET RNA isolation kit from Roche Diagnostics (Indianapolis, IN). NanoString gene expression profiling was conducted using 50 ng of RNA run on the nCounter Pan-Cancer Immune Profiling Panel from NanoString Technologies (Seattle, WA) per manufacturer's instructions. Normalized gene expression values from the NanoString assay were calculated by subtracting the log10 transformed raw counts for each gene from the log10 calculated mean of the housekeeping genes. An interferon gamma gene signature score was obtained using a calculation that compared the normalized value to a predefined weighted score for each gene within the signature.

Immunohistochemistry

PD-L1 expression in a tumor was assessed using IHC as described previously (Daud, A. I., Wolchok, J. D., Robert, C., Huta, W. J., Weber, J. S., Ribas, A., Hodi, F. S., Joshua, A. M., Kefford, R., Hersey, P., et al. (2016). Programmed Death-Ligand 1 Expression and Response to the Anti-Programmed Death 1 Antibody Pembrolizumab in Melanoma. J Clin Oncol 34, 4102.4109) using an investigational version of the Dako PD-L1 22C3 assay (Carpinteria, Calif).

For CD8 and granzyme B IHC analysis, a hematoxylin and eosin stain was performed and reviewed by a pathologist to verify the presence of melanoma and to define tumor areas as regions of interest for analysis. The anti-CD8 mouse monoclonal antibody clone C8/144B was used for CD8 IFIC. The anti-granzyme B mouse monoclonal antibody clone GrB-7 (Dako) was used for granzyme B IHC. Immunohistochemical detection was performed with a polymer-based detection method and a red chromogen. Slides were scanned using a ScanScope CS or AT Turbo system (Aperio, Vista, CA, USA), the region of tumor was circled, and the density of positive cells (e.g., CD8-positive cells per mm$^2$) was evaluated by automated image analysis.

Immunofluorescence

Available paired, pre- and post-treatment biopsies were evaluated using MultiOmyx™ technology to stain 12 biomarkers using a single slide. Repeated cycles of staining using a pair of antibodies directly conjugated to either Cy3 or Cy5, followed by imaging and dye inactivation were performed according to published methods (Au et al., 2016; Gerdes et al., 2013).

Quantification and Statistical Analysis

Using a 6+3 trial design, six to nine DLT-evaluable patients were required to assess the DLT profile of talimogene laherparepvec in combination with pembrolizumab, assuming a true DLT incidence; rate between 11%-33%. Additional patients were enrolled to evaluate the association between biomarkers and response.

The DLT analysis set included all DLT-evaluable patients enrolled in phase 1b who had the opportunity to be on treatment ≥6 weeks from the initial dose of pembrolizumab and who received ≥2 doses of talimogene laherparepvec and 2 doses of pembrolizumab in combination, or who experienced a DLT within 6 weeks of starting combination therapy. The safety analysis sets included all patients who received ≥1 dose talimogene laherparepvec or pembrolizumab. Predictive biomarker analyses included all patients with a baseline biomarker result; analyses of biomarker changes included all patients with a baseline biomarker result and ≥1 subsequent biomarker result.

Corresponding exact 95% confidence intervals (95% CI) for were calculated for ORR and disease control rate. PFS (time from enrollment to disease progression per modified irRC or death) and OS (time from enrollment to death) were estimated using the Kaplan-Meier method.

For cell density or H-score results from IHC, change from baseline was assessed with the sign-test of log2 ratio of post baseline over baseline (week 1) in injected and non-injected lesions separately. For flow cytometry results, change from baseline assessed with a linear mixed effects model with baseline as covariate for log10 ratio (absolute counts or MESF) or %-difference to/from baseline. For immunofluorescence-based multiparameter imaging, effects on cell density were assessed with linear mixed effects models for cube root of density with factors visit and injection status (Ribas, A. (2015), Adaptive Immune Resistance: How Cancer Protects from Immune Attack. Cancer Discov 5, 915-919).

Association with the unconfirmed best response per investigator as of August 2016 was evaluated with a logistic regression of response (CR or PR) vs. continuous biomarker results at either baseline or change from baseline at a given visit. Transformed results were used for analyses. Injected and non-injected lesions analyzed separately. Kruskal-Wallis test was also evaluated in cases of small sample size.

FDR controlled at 5% with the Benjamini-Hochberg procedure and flow cytometry analysis was stratified by a priority set of endpoints and reporting metric (Abs, MESF, %).

Data and Software Availability

Statistical analyses were conducted using SAS version 9.2 (SAS Institute, Cary, NC). Biomarker statistical analyses were conducted using Matlab R2015a (The Mathworks Inc., Natick, MA).

Example 2. Safety and Tolerability of Combining Talimogene Laherparepvec with Pembrolizumab In the phase 1b clinical trial, intratumoral talimogene laherparepvec, and intravenous pembrolizumab were administered to 21 patients with advanced melanoma who had skin lesions amenable to injection. The combination was generally well tolerated, with fatigue, fevers and chills as most common adverse events. There were no dose-limiting toxicities. One patient had pneumonitis, a known toxicity of anti-PD-1 therapy. The confirmed objective response rate was 62%, with a complete response rate of 33%. Patients who responded to the combination of talimogene laherparepvec and pembrolizumab had an increase in CD8+ T-cells in tumors after talimogene laherparepvec. After talimogene laherparepvec treatment, PD-L1 increased on multiple immune cell subsets in tumors along with interferon gamma gene expression. Response to the combination therapy was independent of the baseline infiltration by CD8+ T-cells or interferon gamma signature. These findings indicated that the intratumoral injection of talimogene laherparepvec may favorably change the tumor microenvironment by attracting T-cells into tumors, thereby facilitating the clinical activity of PD-1 blockade therapy.

The phase 1b trial included a baseline biopsy before starting on intratumoral talimogene laherparepvec injections, with a first injection of up to 4 mL×$10^6$ plaque-forming units (pfu) per mL with the goal of inducing seroconversion and a protective immune response to the oncolytic viral vector, followed three weeks later with repeated injections of the full dose of up to 4 mL×$10^8$ pfu/mL of talimogene laherparepvec every two weeks (FIG. 1A). A second tumor biopsy was performed prior to administration of the second full dose of talimogene laherparepvec and before starting on pembrolizumab given at 200 mg intravenously every 2 weeks coinciding with the next doses of talimogene laherparepvec. The run-in period with single agent talimogene laherparepvec administration was designed to analyze how intratumoral injection of talimogene laherparepvec alters the tumor microenvironment before starting on the combination therapy. A third tumor biopsy was planned during the combination therapy part of the study (FIGS. 1A and 6). The clinical trial enrolled 21 patients with advanced melanoma and peripheral lesions amenable to intratumoral injection between December 2014 and March 2015 (see Table 2 for full patient characteristics). Patients were followed up for an average of 188 months (range 17.7 to 20.7) at the time of reporting.

TABLE 2

Baseline Demographics and Clinical Characteristics

| | Talimogene laherparepvec plus pembrolizumab (N = 21) |
|---|---|
| Sex, n (%) | |
| Female | 13 (62) |
| Male | 8 (38) |
| Median (range) age, y | 58 (37-89) |
| ECOG performance status, n (%) | |
| 0 | 19 (90) |
| 1 | 2 (10) |
| Disease substage, n (%) | |
| IIIB | 1 (5) |
| IIIC | 6 (29) |
| IVM1a | 2 (10) |
| IVM1b | 4 (19) |
| IVM1c | 8 (38) |
| LDH, n (%) | |
| ≤ULN | 16 (76) |
| >ULN to 2× ULN | 5 (24) |
| >2× ULN | 0 |
| HSV serostatus, n (%) | |
| Positive | 16 (76) |
| Negative | 5 (24) |
| BRAF status, n (%) | |
| Mutant | 4 (19) |
| Wild-type | 17 (81) |
| PD-L1 status*, n (%) | |
| Positive | 17 (81) |
| Negative | 2 (10) |
| Unknown | 2 (10) |

TABLE 2-continued

Baseline Demographics and Clinical Characteristics

|  | Talimogene laherparepvec plus pembrolizumab (N = 21) |
|---|---|

ECOG, Eastern Cooperative Oncology Group;
HSV, herpes simplex virus;
LDH, lactate dehydrogenase;
PD-L1, programmed death ligand 1;
ULN, upper limit of normal.
*Cutoff for positivity was ≥1% PD-L1 by immunohistochemistry.

With the combined therapy, there were no novel or dose limiting toxicities in any of the 21 patients. The most common toxicities were fatigue (62%), chills (48%), and fever (43%), which were anticipated with the intratumoral injection of talimogene laherparepvec (Andtbacka et al., 2015). Common pembrolizumab-related adverse events were fatigue (62%), rash (33%), and arthralgia (33%), which were anticipated with this agent (Ribas et al., 2016) The only serious adverse event attributed by the study investigators potentially to the combination was grade 1 cytokine release syndrome (one patient). Serious adverse events attributed to pembrolizumab included grade 3 autoimmune hepatitis, grade 3 aseptic meningitis, and grade 4 pneumonitis (one patient each). In the patient with treatment-related aseptic meningitis, no herpes simplex virus was detected in the cerebrospinal fluid, and the patient had stopped therapy with talimogene laherparepvec and pembrolizumab one month earlier and had already switched therapy to dabrafenib and trametinib at the time of first presentation of this adverse event.

Figure 1B:
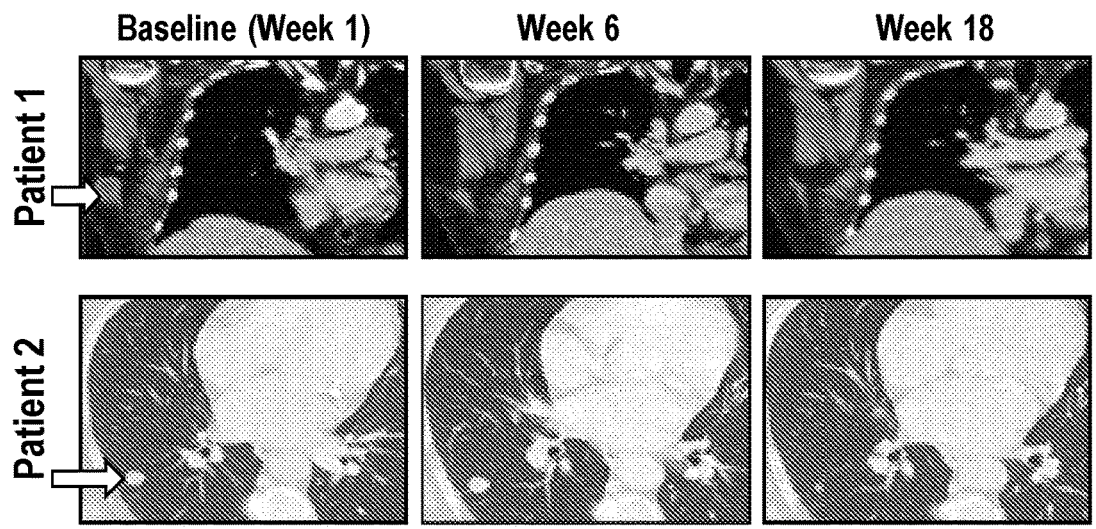
Figure 1C:
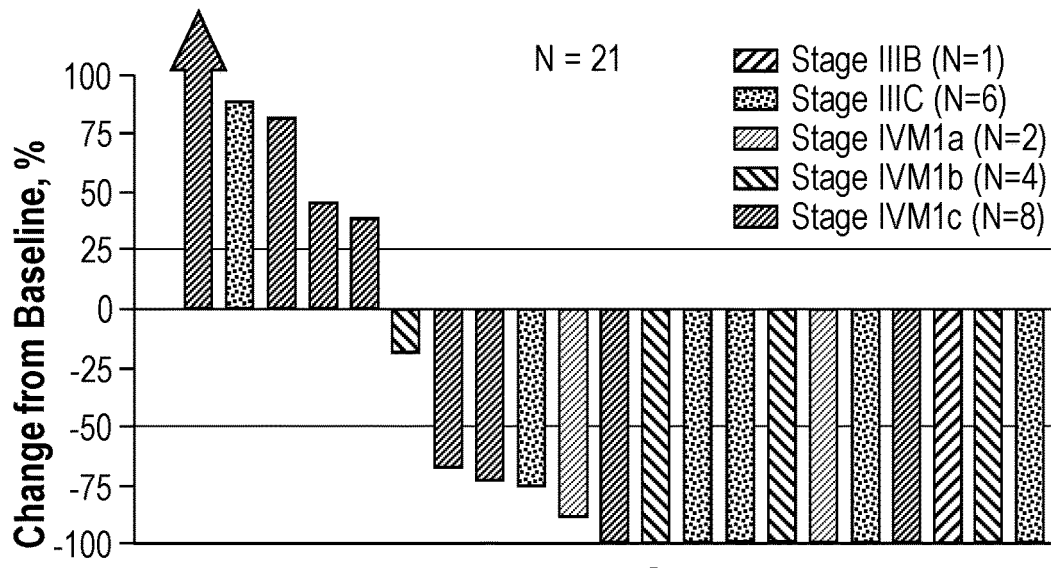
Figure 1D:
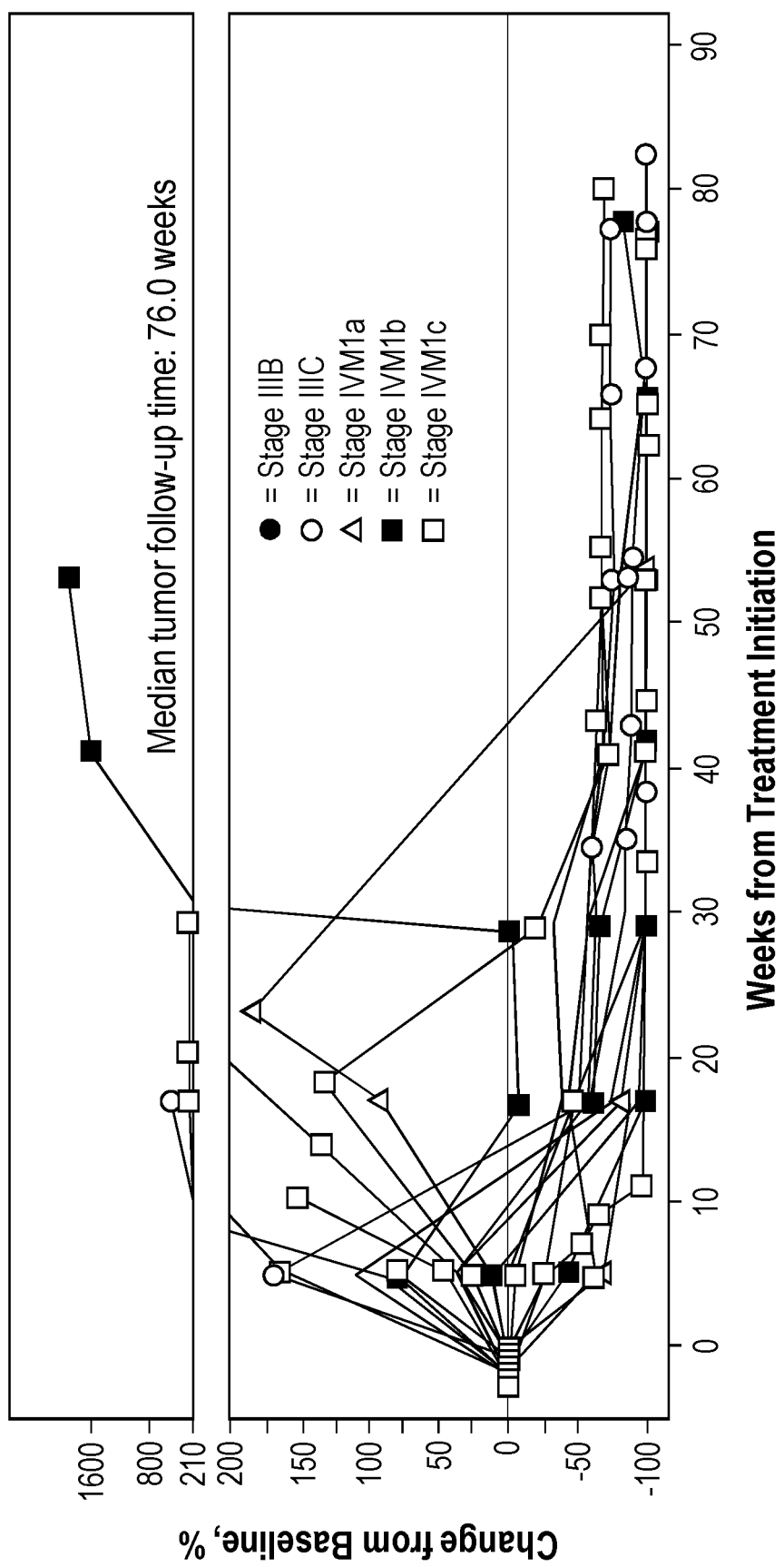
Figure 1E:
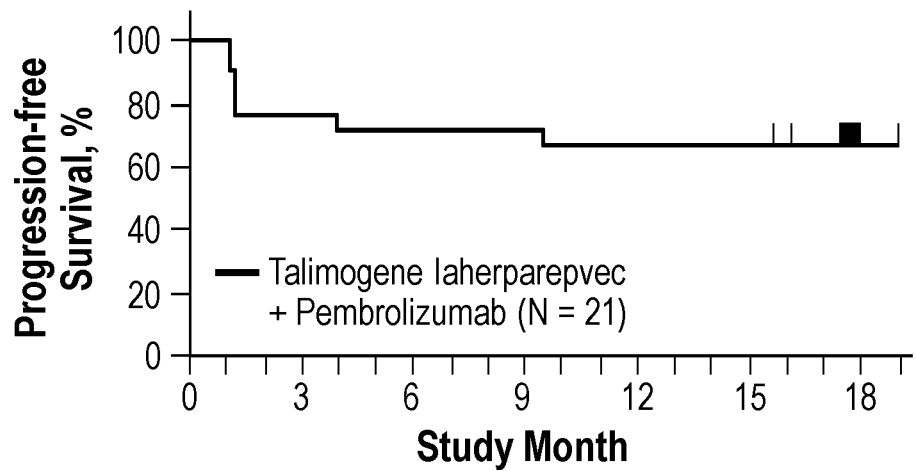
Figure 1F:
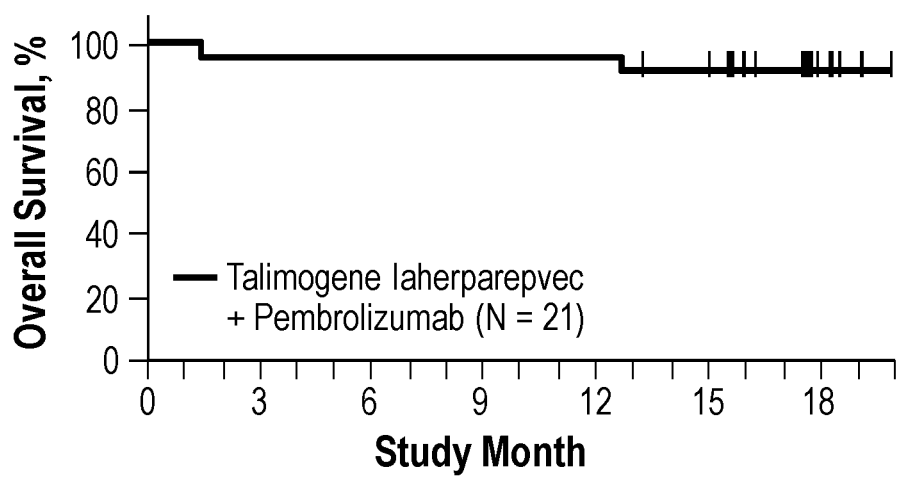

Example 3. Anti-Tumor Activity with Combined Talimogene Laherparepvec and Pembrolizumab The confirmed objective response rate per immune-related response criteria (irRC) (Wolchok et al., 2009) was 61.9% (95% CI, 38.4%-81.9%), with a confirmed complete response rate of 33.3% (95% CI, 14.6%-57.0%) (Table 3). Responses occurred across all substages of melanoma (FIGS. 1B and C). Nine patients presented a transient increase in overall tumor size during the administration of talimogene laherparepvec, in particular after the first sub-therapeutic dose and before receiving the full dose of talimogene laherparepvec together with pembrolizumab but sill these lesions responded later with the combined therapy (FIG. 1D). Median progression free survival (PFS) and overall survival (OS) were not reached at the time of last follow up (FIGS. 1E and F). The combination treatment resulted in a greater than 50% size reduction in 82% of injected, 43.5% of non-injected non-visceral, and 33.4% of non-injected visceral lesions (FIG. 6).

TABLE 3

Best Overall Response*

|  | Talimogene laherparepvec plus pembrolizumab (N = 21) | |
|---|---|---|
|  | Total§ | Confirmed§ |
| Patients with a response | 15 | 13 |
| Response rate, % (95% CI) | 71 (48-89) | 62 (38-82) |

TABLE 3-continued

Best Overall Response*

|  | Talimogene laherparepvec plus pembrolizumab (N = 21) | |
|---|---|---|
|  | Total§ | Confirmed§ |
| Best overall response, n (%) | | |
| Complete response | 8 (38) | 7 (33) |
| Partial response | 7 (33) | 6 (29) |
| Stable disease† | 1 (5) | 3 (14) |
| Progressive disease | 5 (24) | 5 (24) |
| Disease control rate, n (%) | 16 (76) | 16 (76) |

*Response was evaluated per immune-related response criteria by investigators.
†A best overall response of stable disease required an evaluation of stable disease no earlier than 77 days after enrollment.
§Responses were confirmed by a subsequent assessment at least 4 weeks later.

Figures 2A, 2B:
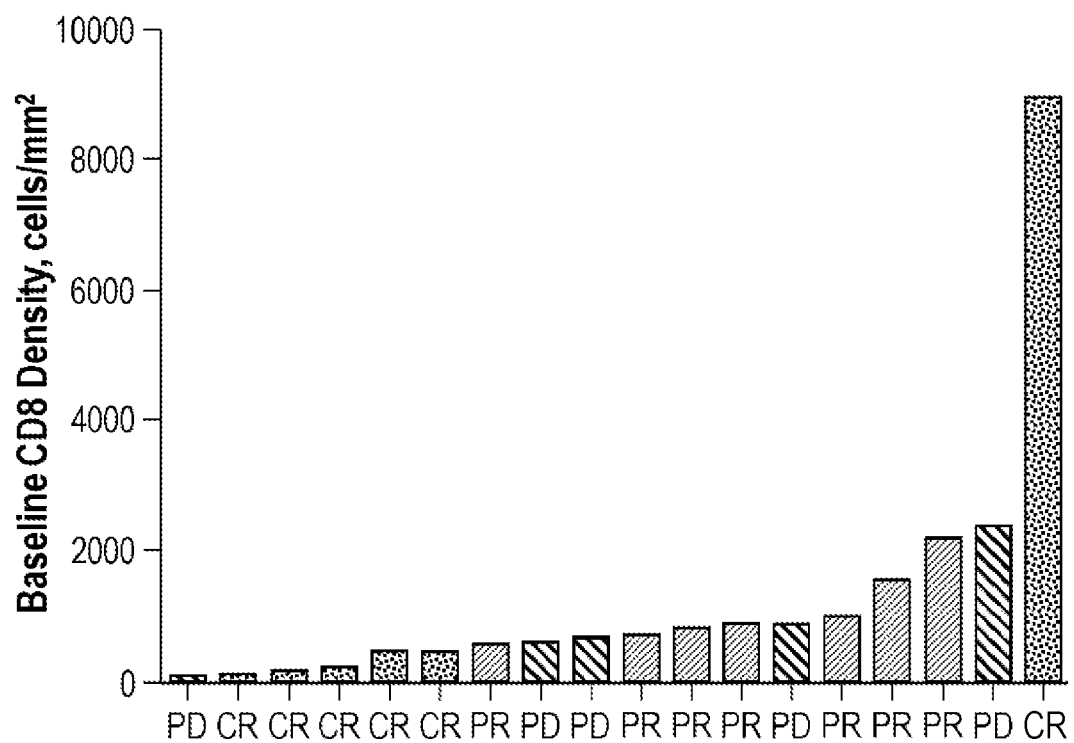
FIG. 2 illustrates that a combination of talimogene laherparepvec and pembrolizumab was effective in patients with low tumor CD8 density. (A) Depicts baseline CD8 density in tumor biopsies according to response rate. The magnitude of bars indicates baseline tumor CD8 density in each patient's baseline biopsy, and best overall response is indicated on x-axis and by bar patterns. Dots: complete response (CR); left diagonal stripes: partial response (PR), thick right diagonal stripes: progressive disease (PD). (B) Baseline PD-L1 by IHC status (1% cut off) and interferon gamma signature score by NanoString analysis is shown under each patient's CD8 result. Best overall response per investigator is shown as of cutoff date of August 2016. n.a.=result not available.

Example 4. Tumor Responses Independent of the Baseline CD8+ T-Cell Infiltration, PD-L1 Status and Interferon Signature PD-L1 is induced by interferon gamma produced by tumor-infiltrating, antigen-specific T-cells, in what is termed adaptive immune resistance allowing cancer cells to avoid the cytotoxic activity of T-cells (Pardoll, 2012; Ribas, 2015). These T-cells are then blocked by PD-1:PD-L1 interactions. Patients who respond to single agent PD-1 blockade therapy have higher densities of baseline CD8+ T-cell infiltration, interferon gamma gene expression signatures and PD-L1 expression (Herbst et al., 2014; Ribas et al., 2015; Tumeh et al., 2014). Vaseline biopsies of patients in the phase 1b clinical trial described herein were analyzed for CD8+ T-cell density, PD-L1 positivity and interferon gamma gene signature. As opposed to the prior experience with single agent pembrolizumab therapy (Ribas et al., 2015; Tumeh et al., 2014), responses in the subject clinical trial were evident in patients whose baseline biopsies had very low CD8+ T-cell infiltrates or had a negative interferon gamma gene signature or has a negative PD-L1 status. Among thirteen biopsies with a CD8+ density of less than 1,000 cells/mm$^2$, nine patients went on to respond to therapy and four patients had disease progression (FIG. 2A). Out of the five baseline biopsies with a low interferon gamma signature, three patients went on to have a complete response and two had disease progression (FIG. 2B). There was only one baseline biopsy that was scored as being PD-L1 negative, but that patient went onto have a complete response to the combined therapy (FIG. 2C).

Figure 3A:
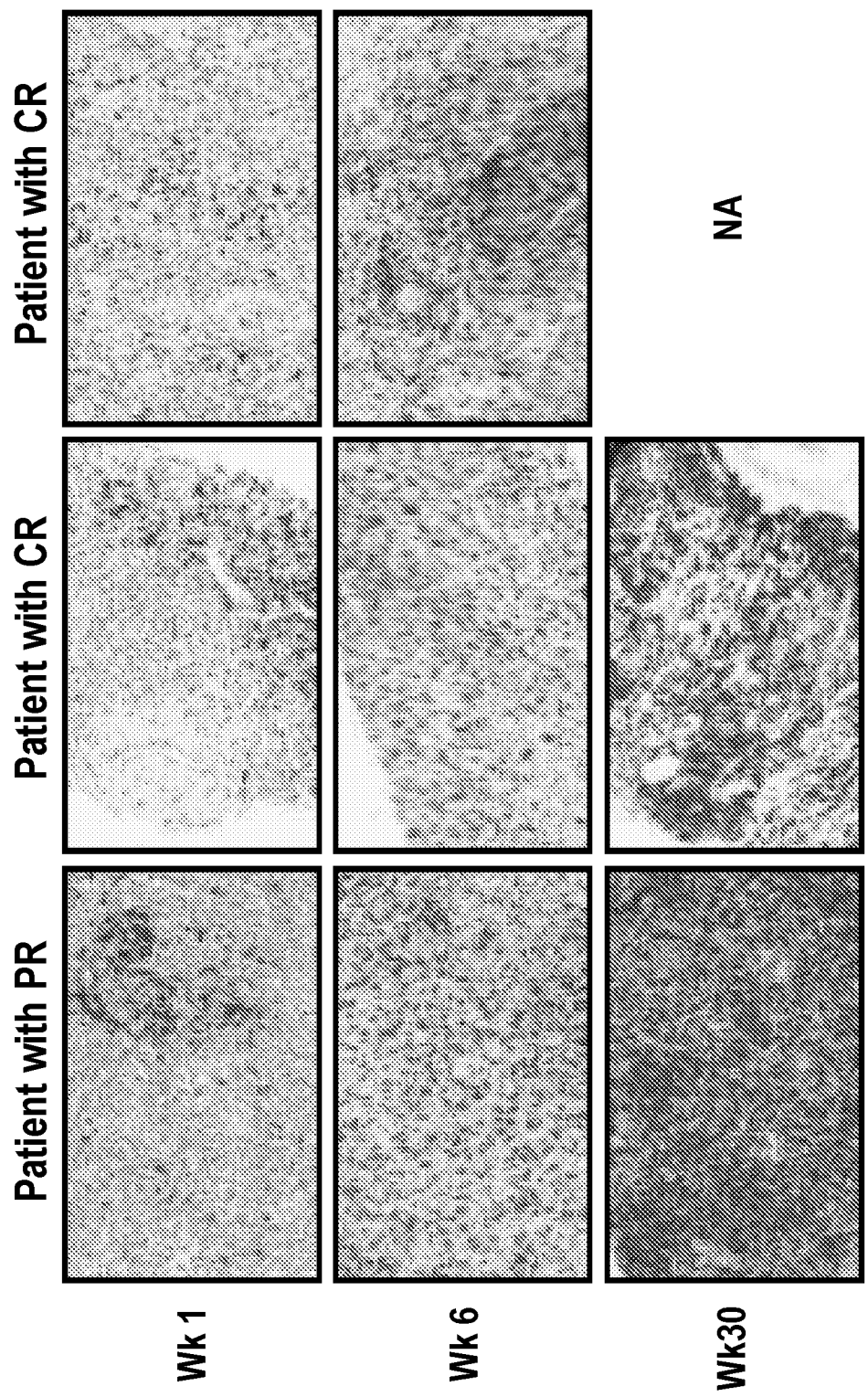
FIG. 3 shows that talimogene laherparepvec increased tumor CD8 density in patients responding to a combination of talimogene laherparepvec and pembrolizumab. (A) Depict examples of pre- (week 1) and post- (week 6) talimogene laherparepvec and talimogene laherparepvec plus pembrolizumab (week 30) CD8+ T-cell density in tumor biopsies: visualization of cells stained with CD8 antibody with red chromogen. Staining was quantified for tissue regions of interest including CD8 density in tumor as shown for talimogene laherparepvec injected tumors. (B) Depicts CD8 density, and (C) granzyme-B H-score which is shown for baseline and post baseline biopsies. The left side in each panel shows post baseline results from injected lesions and the right side in each panel shows results from non-injected lesions. Open circles and closed circles indicate results from tumor biopsies that were depleted of melanoma cells, but that had pathological features of having previously been infiltrated by melanoma cells such as melanin deposits. Response is coded with open circles or closed circles for best overall response per investigator: complete or partial response in open circles and non-response in closed circles. (D) Depicts CD8α and (E) interferon gamma normalized mRNA transcript count measured in the NanoString Pan Cancer Immune Profiling Panel.
Figure 3B:
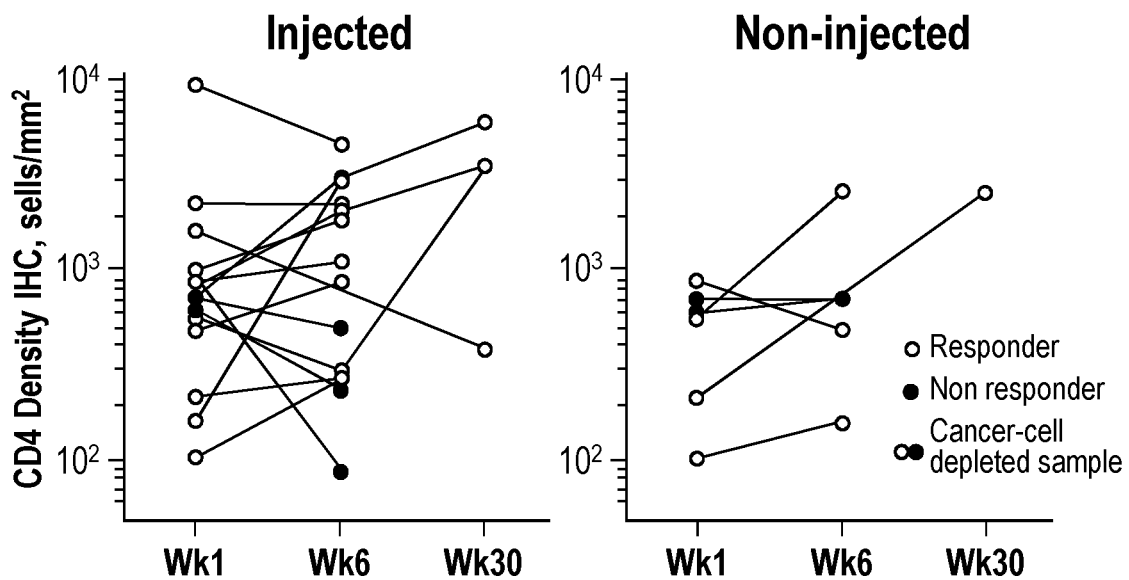
Figure 3C:
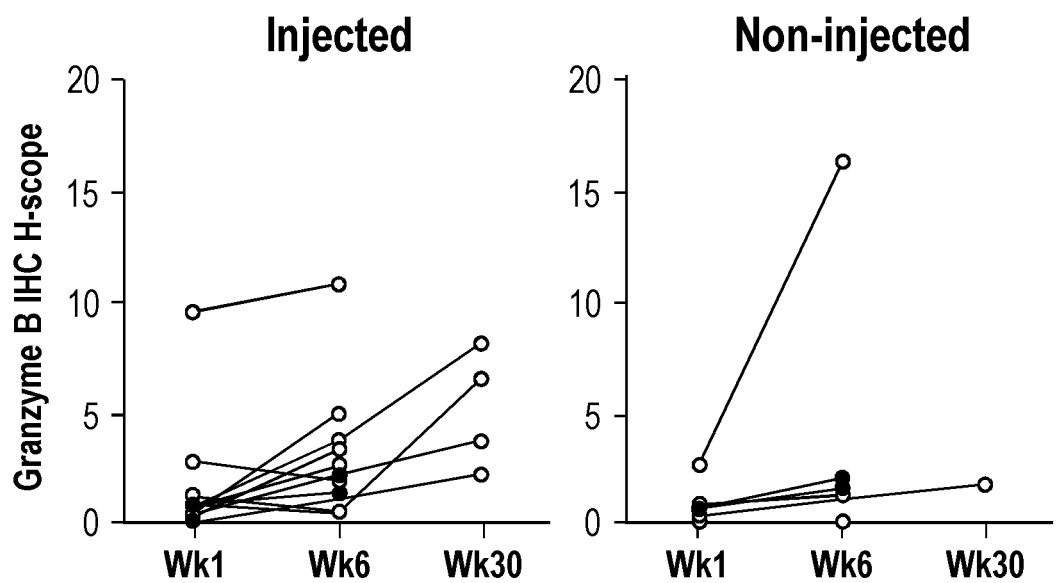
Figure 3D:
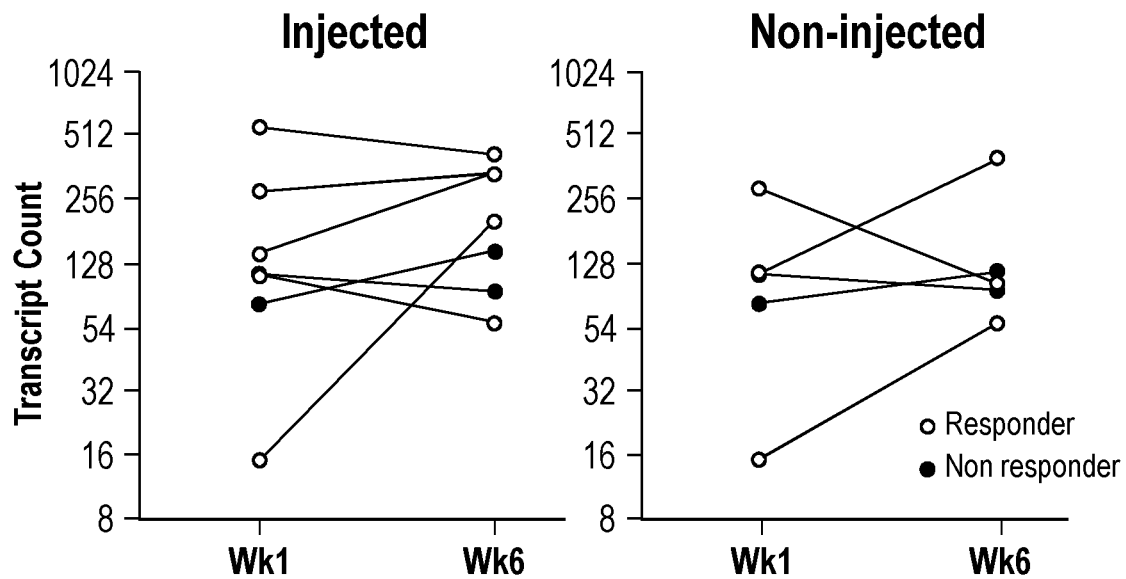
Figure 3E:
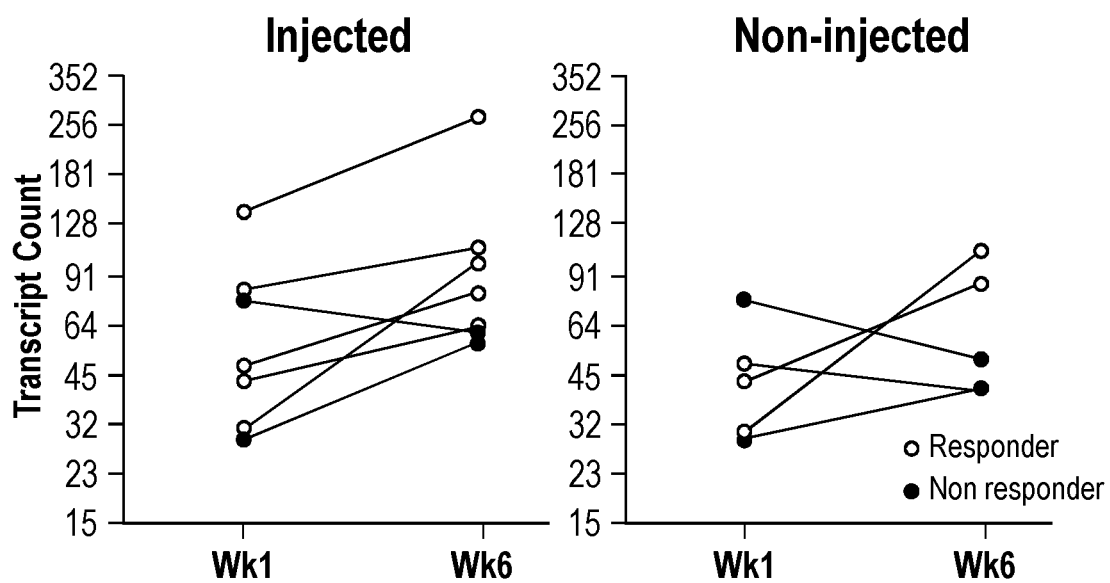
Figure 8A:
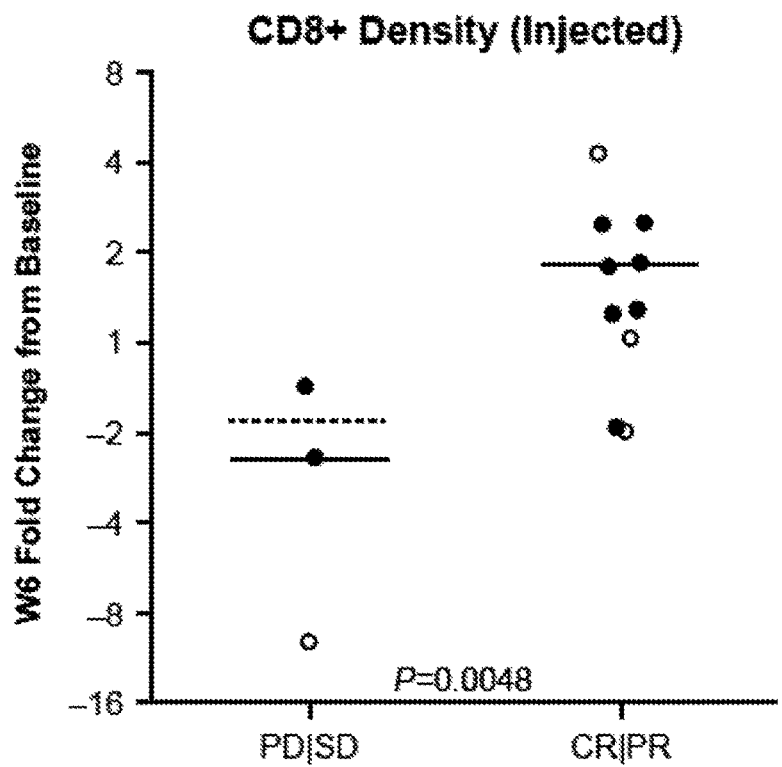
FIG. 8 shows that responders had CD8 density increases in injected lesions after talimogene laherparepvec administration. Changes from baseline (BL, week 1) in CD8 density as measured by IHC after talimogene laherparepvec treatment but before the start of combination therapy (W6) are plotted for responders and non-responders separately. The left panel shows changes in injected lesions (Inj) and the right panel shows changes in non-injected (Not Inj) lesions on a fold-change scale. Response was defined as best overall response per investigator of CR or PR, and non-response as PD or SD. Tumor-depleted samples are indicated with open circles. Median fold change is indicated with a horizontal line (solid for all samples, dashed for only those with tumor present).
Figure 8B:
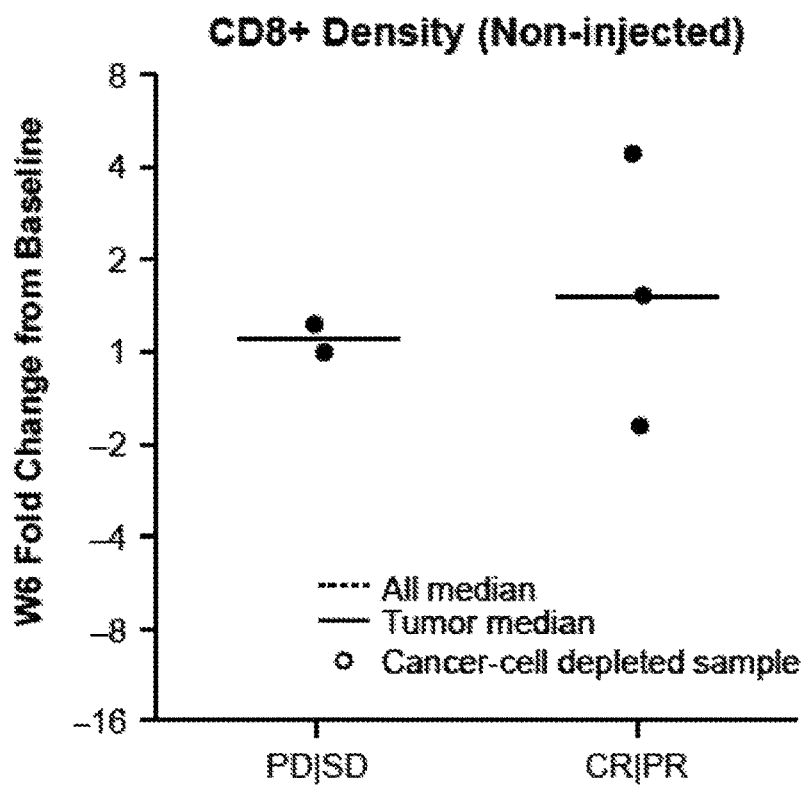

Example 5. Talimogene Laherparepvec Intratumoral Injections Increase CD8+ T-Cell Infiltration in Patients Who Respond to Combined Therapy As some patients whose baseline biopsies had relatively low CD8+ cell density and were not positive for an interferon gamma gene signature went onto have an objective response, the run-in period with single agent talimogene laherparepvec was performed to determine if talimogene laherparepvec had changed the tumor microenvironment by bringing in T-cells into metastatic melanoma lesions in patients who responded to therapy. Indeed, immunohistochemical (IHC) analysis comparing baseline biopsies with biopsies performed after talimogene laherparepvec alone showed an increase in the density of infiltrating CD8+ T-cells in eight out of twelve injected lesions available for analysis, which further increased in several of the biopsies obtained at the time of combined therapy (FIGS. 3A and B). In three patients with a response to therapy, the CD8+ density went down in the on-therapy biopsy, and one additional patient had no change in CD8+ density. The three patients without a response all had a decrease in the CD8+ density in the on-therapy biopsies. Overall, the increase in CD8+ density was most evident in the injected lesions of the patients who went on to respond to therapy (FIG. 3B), a relationship supported by logistic regression (p=0.0048, FIG. 8A). The change in CD8+ infiltration density was variable in the non-injected lesions at week 6 even in patients who later responded to therapy, with the caveat that there were only three such biopsies available for interpretation (FIG. 3B). Some biopsies were found to have low residual tumor content after treatment (as indicated by open symbols in FIGS. 3B and C), which, without intending to be bound by scientific theory, may have been due to either a complete pathological response at that site or a biopsy that missed the melanoma deposit. Four out of five responding biopsies with these tumor-depleted samples showed relatively high CD8+ T-cell density at week 6 as compared to the biopsy of a single patient with a progression included in this set. IHC was also performed for the cytotoxic granule component granzyme B (associated with a subset of CD8 T-cells and NK-cells), which has been shown to increase in tumors after PD-1 blockade (Tumeh et al., 2014). A trend suggesting increased granzyme B in tumors after talimogene laherparepvec and combination treatment was also observed in particular for the biopsies with low residual tumor content (FIG. 3C). Furthermore, on analysis of tumor gene expression data it was determined that CD8+ alpha and interferon gamma mRNAs were elevated after treatment, providing additional supporting evidence for treatment-related change in the tumor microenvironment increasing the number of interferon gamma-producing cytotoxic T-cells (FIG. 3D, 3E). CD8 alpha increased L7-fold (p=0.01) in injected lesions at week 6 compared to baseline, and 1.44-fold (p=0.0012) in non-injected lesions. Similarly, the interferon gamma increases for injected and non-injected lesions were 1.63 (p=0.0004) and 1.41 (p=0.17), respectively.

Figure 4A:
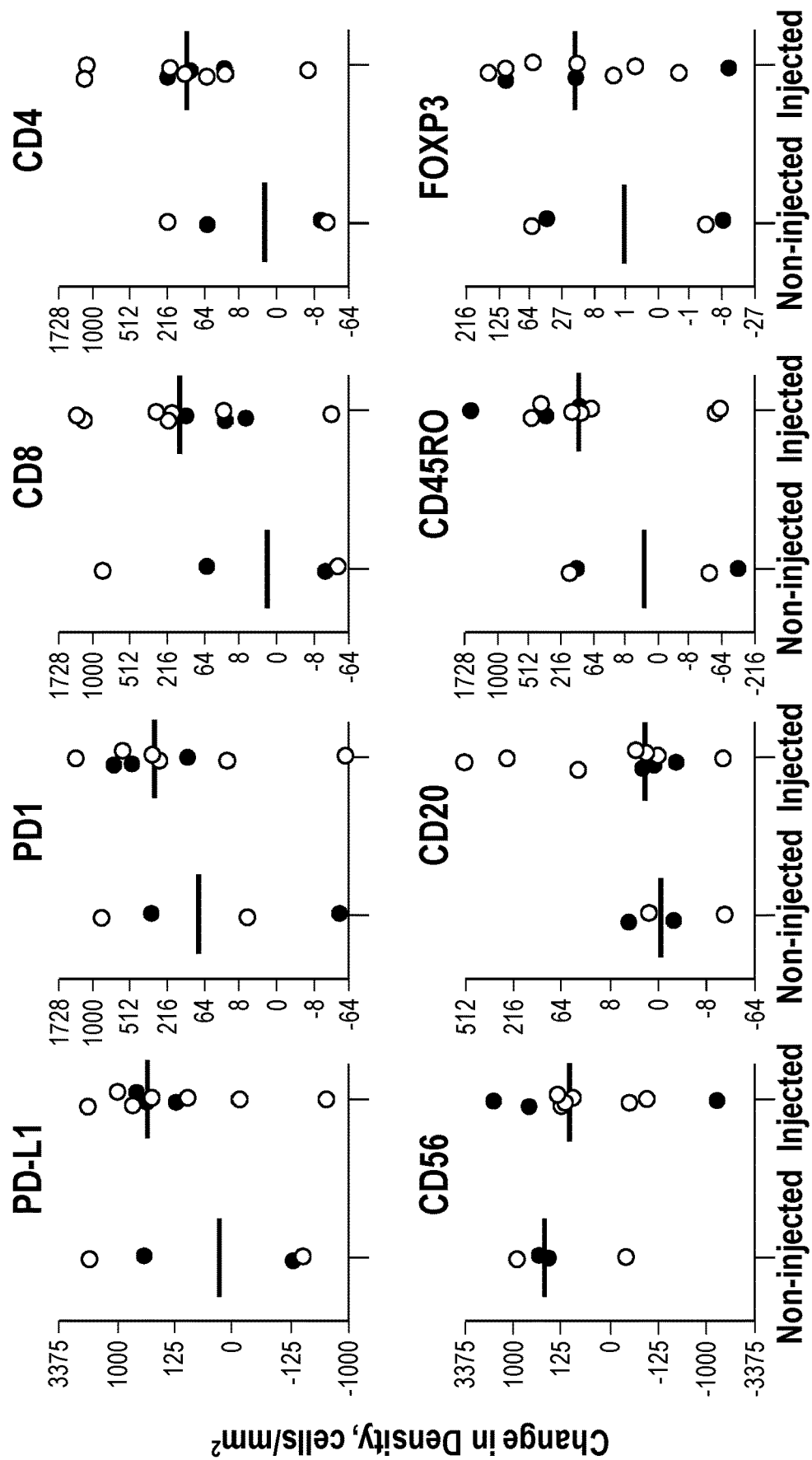
FIG. 4 shows that talimogene laherparepvec increases tumor infiltrating lymphocyte density and PD-L1 expression in tumors. Twelve color immunofluorescence staining was performed on a single slide from paired pre- and post-talimogene laherparepvec tumor biopsies from each of 13 patients. Markers evaluated included S100 (as melanoma segmentation marker), CD3, CD4, CD8, PD-1, PD-L1, CTLA-4, CD45RO, Foxp3, CD56, CD68 and CD20. (A) Depicts a subset of changes at week 6 from baseline in marker cell positive cell density for results with statistical significance (PD-L1, PD-1, CD8, CD4, CD56, CD20, CD45RO and Foxp3) are graphed for non-injected samples (left) and injected samples (right). Median change for each subset is shown with a horizontal line. Response is coded with open circles or closed circles for best overall response per investigator: complete or partial response in open circles and non-response in closed circles. (B) Shows an example of the combination of S100, CD8 and PD-L1 staining shown at low (top row) and high (bottom row) magnification for a baseline biopsy from a patient who went onto have a partial response (week 1), week 6 after injection of talimogene laherparepvec, and at week 30 after long term treatment with the combination of talimogene laherparepvec and pembrolizumab. NI: biopsy of a non-injected metastasis; I: biopsy of an injected metastasis.
Figure 4B:
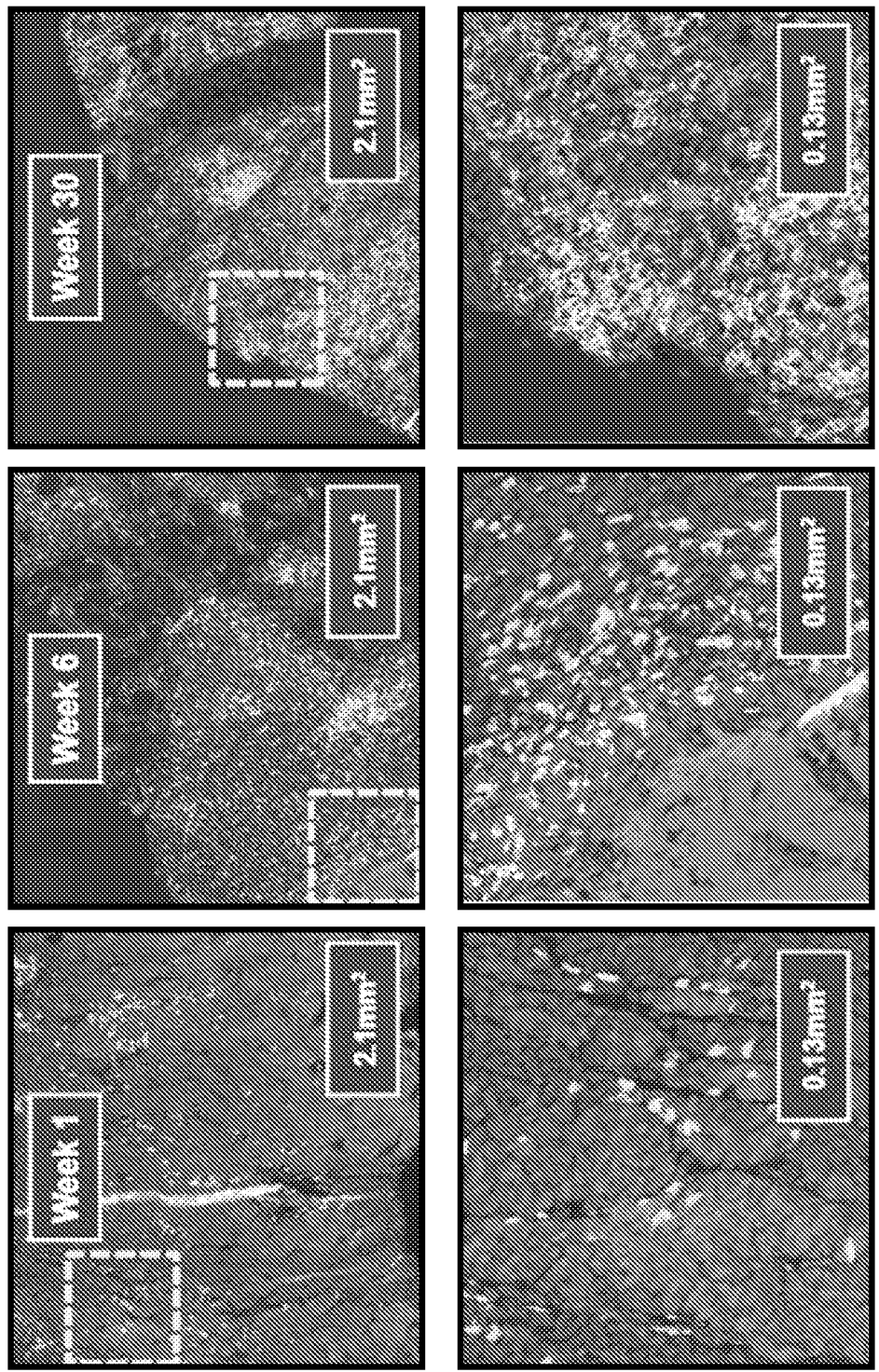
Figure 9:
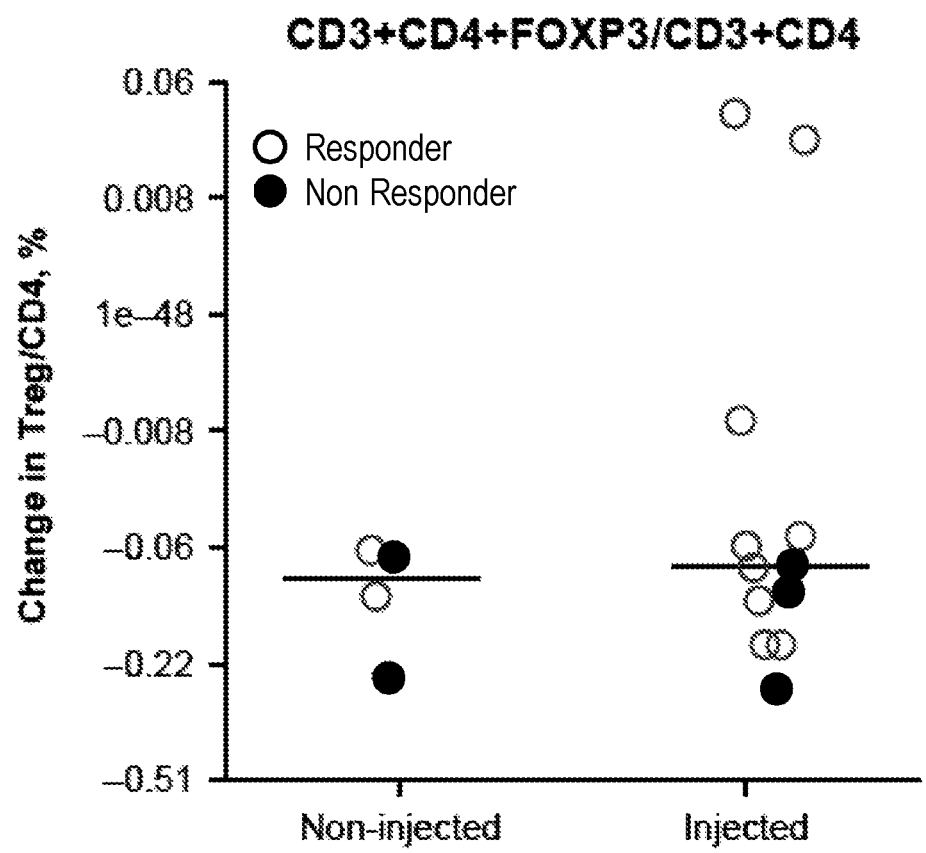
FIG. 9 shows that talimogene laherparepvec decreases Treg fraction of CD4 T-cells in tumors. Twelve color immunofluorescence staining was performed on a single slide from paired tumor biopsies at pre- and post-talimogene laherparepvec from each of 13 patients. Markers evaluated included S100 (as melanoma segmentation marker), CD3, CD4, CD8, PD-1, PD-L1, CTLA-4, CD45RO, Foxp3, CD56, CD68 and CD20. Changes from baseline in Treg fraction of CD4 T-cells at week 6 are graphed for non-injected samples (left) and injected samples (right). Median change for each subset is shown with a horizontal line. Response is coded with open circles or closed circles for best overall response per investigator: complete or partial response in open circles and non-response in closed circles.
Figure 10B:
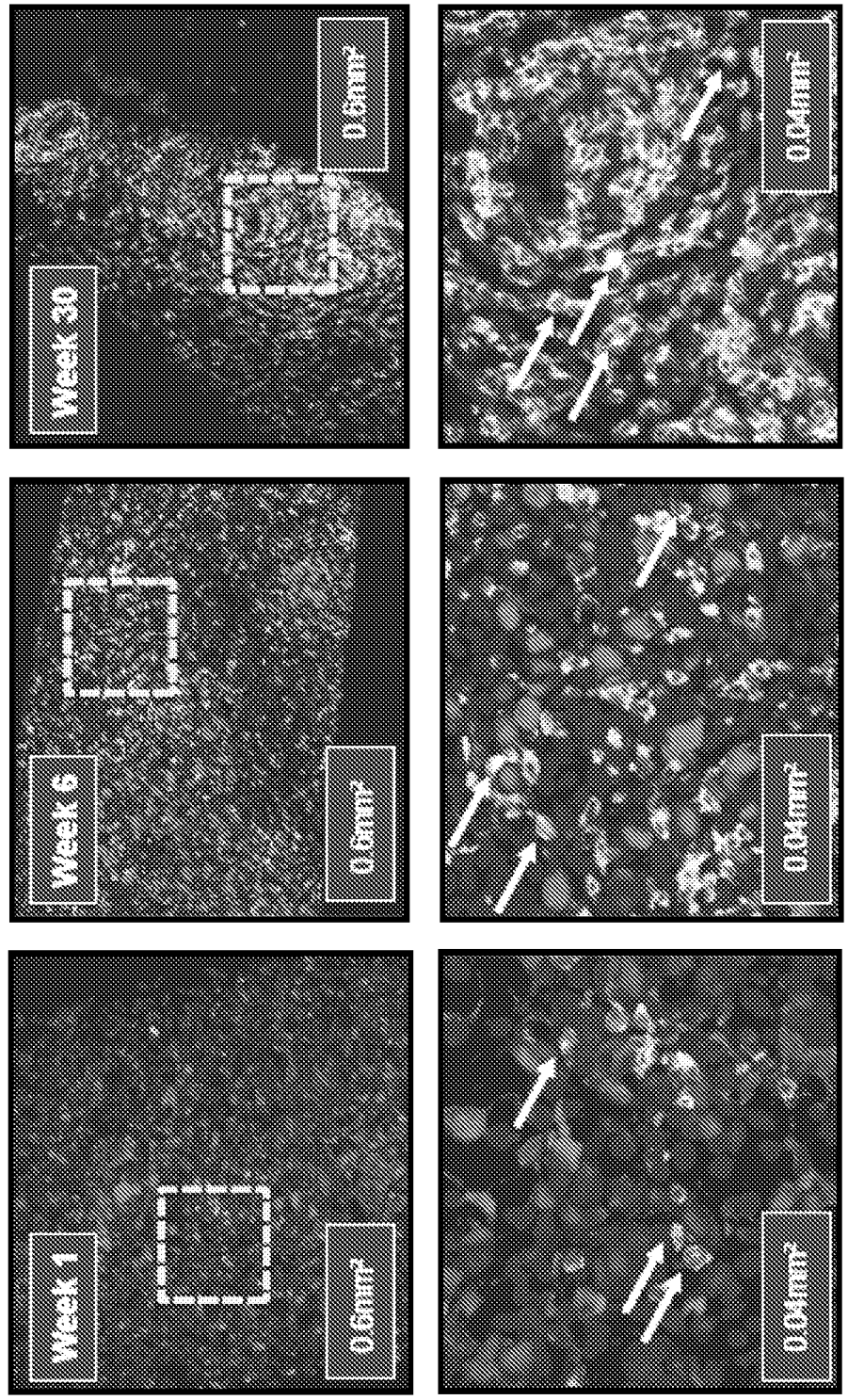
FIG. 10 depicts additional multi-parameter imaging (MultiOntyx™ platform) examples from a patient with a partial response to therapy are shown for (A) the combination of S100, CD8 and PD-L1 (0.6 mm$^2$ and 0.04 mm$^2$ image area) at baseline (week 1), week 6 after injection of talimogene laherparepvec, and at week 30 after long term treatment with the combination of talimogene laherparepvec and pembrolizumab, (B) Depicts S100, CD3, CD4 and Foxp3 staining (0.6 mm$^2$ and 0.04 mm$^2$ image area) for an additional patient.

Example 6. Characterization of Changes in Immune Cell Infiltrates in Talimogene Laherparepvec Injected and Non-Injected Lesions To further characterize the changes in tumors, multiplexed immunofluorescence staining of a subset of paired biopsies at different time points from 13 patients was performed. Broad changes in tumor inflammation were observed after talimogene laherparepvec treatment at week 6, including increased infiltration by immune cells and a clear increase in cells expressing PD-L1 in the eight out of ten of injected tumors and in two out of four non-injected tumors (FIG. 4A). The immune infiltrate included influx of a large proportion of CD4+ and CD8+ T-cells, many co-expressing PD-1, as well as CD56 expressing cells and CD20 positive B-cells in the on treatment biopsies from some patients. Increases were also observed in the density of cells expressing the memory T-cell marker CD45RO and in cells expressing the regulatory T-cell (Treg) marker Foxp3 (FIG. 4A). The magnitude of effector T-cell (Teff) increases, however, was much larger relative to Treg, resulting in an overall decrease in the Treg to Teff ratio in tumors after talimogene laherparepvec (FIG. 9) consistent with previous reports (Kaufman et al., 2010). The full set of immunofluorescence analyses in biopsies is reported in Table 4, which additionally shows that there was no apparent increase in the density of macrophages based on CD68 staining. An example of increased CD8+ and PD-L1 density (by immunofluorescence) at weeks 6 and 30 relative to baseline is shown in FIG. 4B. At weeks 6 and 30, tumor cells co-staining for S100 (grey) and PD-L1 staining (dark) are evident along with CD8 T-cells (white) showing co-expression of PD-L1. The biopsy taken during combined therapy of a responding patient was nearly completely infiltrated by CD8+ T-cells. Additional representative images are depicted in FIG. 10.

TABLE 4

Cell subset changes within the tumor between injected lesions at week 6 and baseline lesions (week 1).

| Cell subset | Baseline density mean [cells/mm$^2$]$^a$ | Week 6 density ratio to baseline† | p-value‡ |
| --- | --- | --- | --- |
| CD3 | 204.21 | 2.57 | $2.28 \times 10^{-23}$ |
| CD4 | 68.96 | 2.73 | $7.56 \times 10^{-21}$ |
| CD8 | 126.15 | 2.47 | $3.70 \times 10^{-20}$ |
| FOXP3 | 32.53 | 1.70 | $1.38 \times 10^{-8}$ |
| PD1 | 202.24 | 2.27 | $1.57 \times 10^{-17}$ |
| PD−L1 | 172.28 | 2.73 | $1.99 \times 10^{-16}$ |
| CD68 | 71.01 | 1.09 | 0.41 |
| CD45RO | 204.57 | 1.56 | $6.86 \times 10^{-6}$ |
| CD56 | 339.99 | 1.31 | $1.30 \times 10^{-3}$ |
| CD20 | 1.58 | 5.33 | $2.03 \times 10^{-9}$ |
| CTLA | 22.49 | 0.77 | 0.09 |
| CD3CD8 | 89.82 | 2.64 | $3.85 \times 10^{-20}$ |
| CD3CD8PD1 | 61.69 | 2.40 | $1.97 \times 10^{-15}$ |
| CD3CD4 | 68.96 | 2.73 | $7.56 \times 10^{-21}$ |
| CD3CD4PD1 | 32.57 | 2.76 | $9.26 \times 10^{-20}$ |
| CD3CD4FOXP3 | 13.00 | 1.90 | $1.46 \times 10^{-7}$ |
| CD68PD_L1 | 10.61 | 2.35 | $4.97 \times 10^{-9}$ |
| CD3+CD4+PD_L1 | 8.43 | 4.74 | $1.70 \times 10^{-20}$ |
| CD3+CD4+CD45RO | 29.72 | 2.02 | $4.53 \times 10^{-8}$ |
| CD3+CD8+CD45RO | 40.52 | 1.94 | $1.49 \times 10^{-7}$ |
| CD3+CD8+PD-L1 | 9.43 | 4.19 | $1.37 \times 10^{-16}$ |
| CD3_CD8+CD56 | 1.01 | 3.34 | $2.53 \times 10^{-6}$ |
| CD3+CD8+CD56+PD_L1 | 0.06 | 5.31 | $5.19 \times 10^{-5}$ |
| CD3+CD4+PD1 | 32.57 | 2.76 | $9.26 \times 10^{-20}$ |
| CD3+CD8+PD1 | 61.69 | 2.40 | $1.97 \times 10^{-15}$ |
| CD3−CD20+ | 1.58 | 5.33 | $2.03 \times 10^{-9}$ |
| CD3−CD20+PD-L1 | 0.16 | 6.35 | $1.15 \times 10^{-7}$ |

Figure 5A:
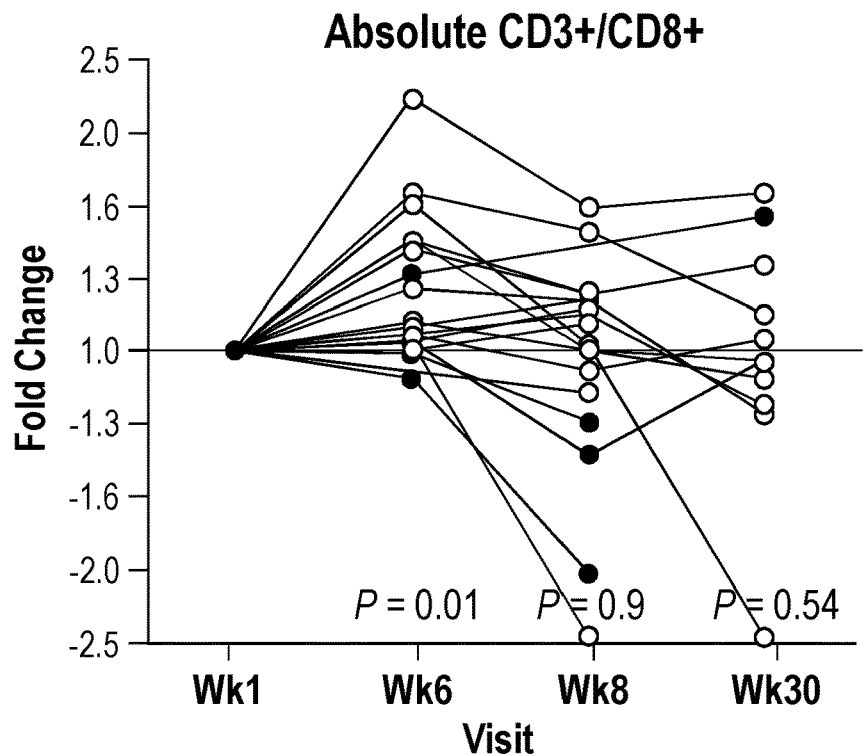
FIG. 5 depicts circulating T-cell subsets and expression of activation markers. Peripheral blood cells obtained from baseline, week 1, week 6, week 8, and week 30 were analyzed by flow cytometry. (A) Fold-change in absolute CD3+/CD8+ cells. (B) Depicts fold-change in absolute CD3+/CD4+ cells. (C) Depicts percent change in Ki67+ (CD3+/CD8+) cells. (D) Depicts percent change in PD-1+ (CD3+/CD8+) cells at week 1 and week 6 only, as after starting on pembrolizumab the staining antibody competed for the same epitope. (E) Depicts percent change in TIM3+ (CD3+/CD8+) cells. (F) Depicts percent change in BTLA+ (CD3+/CD8+) cells. P-values for comparison to baseline are shown below data for each post-baseline visit, based on contrasts from linear mixed effects modeling. Response is coded with open circles or closed circles for best overall response per investigator: complete or partial response in open circles and non-response in closed circles.
Figure 5B:
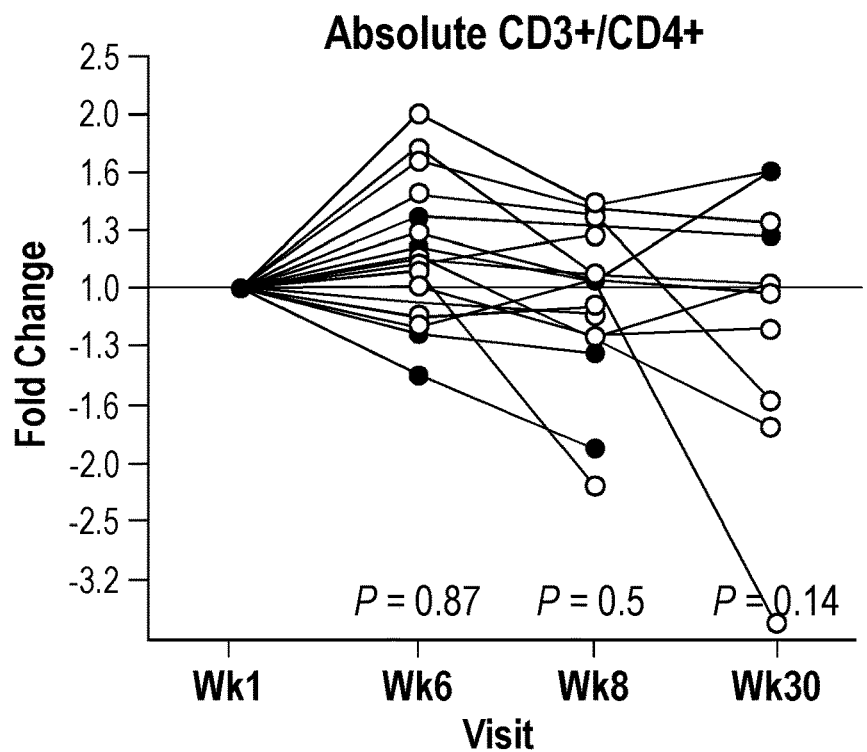
Figure 5C:
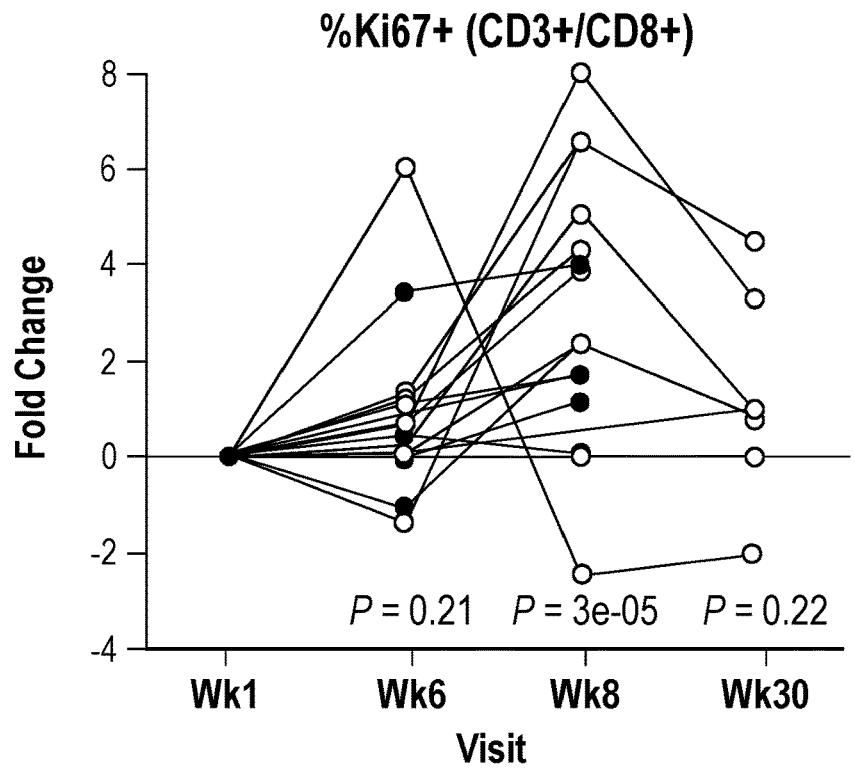
Figure 5D:
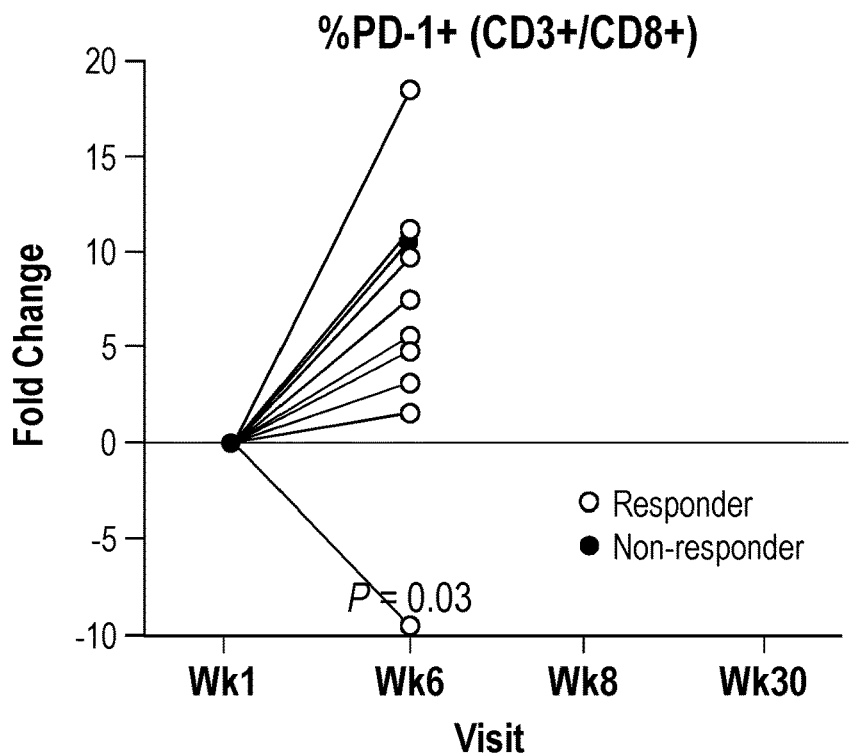
Figure 5:
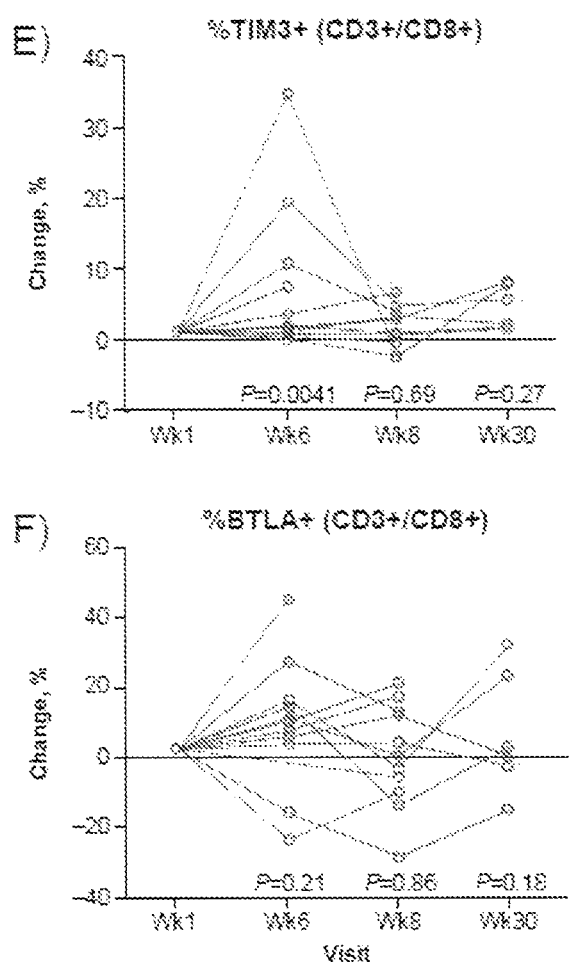

Example 7. Changes in the Functional Phenotype of Circulating T-Cells with Combined Therapy Changes in immune cells were also analyzed in peripheral blood as a potential pharmacodynamic effect of the single agent and combined therapy. After talimogene laherparepvec single agent therapy, the majority of patients had an increase in the number of circulating CD8+ and CD4+ T-cells in peripheral blood, which did not increase further when adding pembrolizumab (FIGS. 5A and B). However, the addition of pembrolizumab tended to increase the number of dividing CD8 T-cells in circulation as indicated by increase in Ki67+CD3+CD8+ T-cells (FIG. 5C). Analysis of the expression of different immune checkpoint receptors in the circulating CD3+ CD8+ T-cells revealed an increase in PD-1 and TIM-3 with single agent talimogene laherparepvec therapy (FIGS. 5D and E), while there was no change in BTLA (FIG. 5F). No associations of response with baseline cell levels or changes over time passed our false discovery controls, Example 8. Discussion This first-in-human combination immunotherapy clinical trial demonstrates a high overall and complete response rate in patients with advanced melanoma, which is mediated by changes in tumor biopsies that are mechanistically correlated with the hypothesis that the injection of the oncolytic virus talimogene laherparepvec would change the tumor microenvironment by attracting T-cells that may induce a systemic response in distant metastases after subsequent blocking of PD-1 with pembrolizumab. Indeed, during the run-in period of the study with single agent talimogene laherparepvec intratumoral administration there was evidence of a systemic increase in circulating CD4 and CD8 T-cells and increased CD8 T-cell infiltration into tumors. These T-cells expressed PD-1 and the tumor cells expressed PD-L1, likely limiting the anti-tumor activity of single agent talimogene laherparepvec, which benefitted from blocking PD-1 resulting in an increased clinical activity beyond what would be expected with either therapy alone. The benefit of increased responses was achieved with a low rate of toxicities, most of which were expected toxicities with the use of single agent talimogene laherparepvec or pembrolizumab (Andtbacka, R. H., Kaufman, H. L, Collichio, F., Amatruda, T., Senzer, N., Chesney, J., Delman, K. A., Spitler, L. E., Puzanov, I., Agarwala, S. S., et al. (2015). Talimogene Laherparepvec Improves Durable Response Rate in Patients With Advanced Melanoma. J Clio Oncol 33, 2780-2788; Ribas, A., Hamid, O., Daud, A., Hodi, F. S., Wolchok, J. D., Keffird, R., Joshua, A. M., Patnaik, A., Hwu, W. J., Weber, J. S., et al. (2016). Association of Pembrolizumab With Tumor Response and Survival Among Patients With Advanced Melanoma. JAMA 315, 1600-1609).

PD-1 blockade therapy with pembrolizumab or nivolumab leads to an objective response of approximately 35-40% for treatment nave patients with metastatic melanoma without prior therapy (Ribas et al., 2016; Robert, C., Long, G. V., Brady, B., Dutriaux, C., Maio, M., Mortier, L., Hassel, J. C., Rutkowski, P., McNeil, C., Kalinka-Warzocha, E., et al. (2015a), Nivolurnab in previously untreated melanoma without BRAF mutation. N Engl J Med 372, 320-330; Robert, C., Schachter, J., Long, G. V., Arance, A., Grob, J. J., Mortier, L., Daud, A., Carlino, M. S., McNeil, C., Lotem, M., et al. (2015b). Pembrolizurnab versus Ipilimumab in Advanced Melanoma, N End. J Med 372, 2521-2532). Without intending to be bound by scientific theory, even considering that the need to select patients that had injectable lesions may have skewed the population of patients in this study, an overall response rate of 62% and a complete response rate of 33% is unlikely to be a result of administering anti-PD-1 therapy alone. In a study of 655 patients treated with pembrolizumab, there were 34 patients who had only skin and nodal metastases (stage M1a), and the overall response rate in this group of patients was 38% (Ribas et al., 2016). A randomized phase 3 clinical trial to further demonstrate that the combination is more effective than either single agent pembrolizumab or talimogene laherparepvec is currently ongoing comparing systemic administration of pembrolizumab with intralesional injection of talimogene laherparepvec or placebo (NCT 02263508).

Patients whose baseline biopsies had low densities of CD8+ T-cells, lack of significant interferon gamma expression, and low PD-L1 expression are unlikely to respond to single agent anti-PD-1 therapy (Ribas, A., Robert, C., Hodi, F. S., Wolchok, J. D., Joshua, A. M., Hwu, W. J., Weber, J. S., Zarour, H. M., Kefford, R., Loboda, A., et al. (2015). Association of response to programmed death receptor 1 (PD-1) blockade with pembrolizumab (MK-3475) with an interferon-inflammatory immune gene signature. J Clin Oncol 33, abstr 3001; Tumeh, P. C., Harview, C. L, Yearley, J. H., Shintaku, I. P., Taylor, E. J., Robert, L., Chmielowski, B., Spasic, M., Henry, G., Ciobanu, V., et al. (2014). PD-1 blockade induces responses by inhibiting adaptive inunune resistance. Nature 515, 568-571). Therefore, the combination therapy described herein should increase the intratumoral infiltration by CD8+ T-cells, which may attract enough T-cells with tumor specificity that may reverse the primary resistance to PD-1 blockade therapy (Chen, P. L., Roh, W., Reuben, A., Cooper, Z. A., Spencer, C. N., Prieto, P. A., Miller, J. P., Bassett, R. L., Gopalakrishnan, V., Wani, K., et al. (2016). Analysis of Immune Signatures in Longitudinal Tumor Samples Yields Insight into Biomarkers of Response and Mechanisms of Resistance to Immune Checkpoint Blockade. Cancer Discov 6, 827-837; Ribas, A. (2015). Adaptive Immune Resistance: How Cancer Protects from Immune Attack, Cancer Discov 5, 915-919). The data presented herein demonstrate that talimogene laherparepvec can provide this combinatorial effect. In the series presented herein, the number of patients whose tumors had low baseline CD8+ density and low interferon gamma signature and still went onto have an objective response to the combined therapy was apparently higher compared to prior experience with single agent pembrolizumab (Ribas et al., 2015; Tumeh, P. C., Harview, C. L., Yearley, J. H., Shintaku, I. P., Taylor, E. J., Robert, L. Chmielowski, B., Spasic, M., Henry, G., Ciohanu, V., et al. (2014). PD-1 blockade induces responses by inhibiting adaptive immune resistance. Nature 515, 568-571).

Evidence that local administration of talimogene laherparepvec was contributing to a systemic anti-tumor effect was provided by the increases in inflammation observed in tumors not injected with talimogene laherparepvec prior to introduction of pembrolizumab. Roughly, two out of the four week 6 non-injected lesions showed increased CD8+ density and PD-L1 (by immunofluorescence), and three out of five for increased interferon gamma mRNA.

The lack of requirement for baseline tumor infiltration will be further evaluated in the ongoing phase 3 study of the talimogene laherparepvec phis pembrolizumab combination, which is currently accruing 655 patients, half receiving the combination and half pembrolizumab with intratumoral placebo in the control arm (ClinicalTrials.gov, NCT02263508). Also, to further evaluate systemic effects of talimogene laherparepvec, a separate biomarker study is ongoing to evaluate baseline and post-talimogene laherparepvec uninjected tumors from over 100 patients (NCT02366195). This will enable follow-up on findings from the small set of tumor biopsies not injected with talimogene laherparepvec in the subject series, many of which showed increased tumor inflammation.

In conclusion, the high response rate in this phase 1 clinical trial and the mechanistic changes documented in patient biopsies indicates that the combination of talimogene laherparepvec, and pembrolizumab can overcome some of the limitations of pembrolizumab or talimogene laherparepvec monotherapy and provide responses in patients beyond what would be expected with either talimogene laherparepvec or pembrolizumab administered alone.

Figure 12:
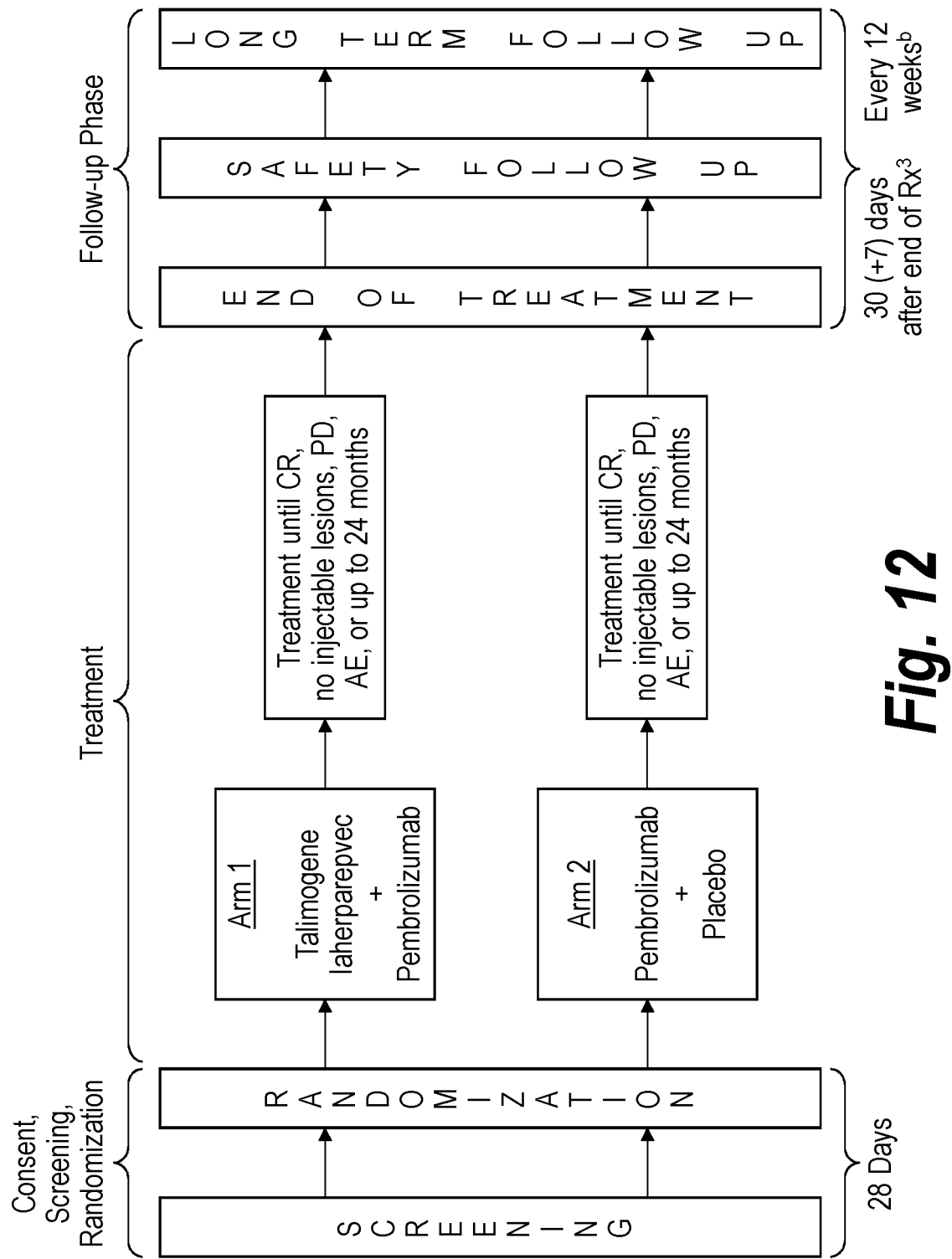
FIG. 12 depicts a schematic of a phase 3 study design and treatment schema in which subjects are treated with talimogene laherparepvec plus pembrolizumab (arm 1) or placebo plus pembrolizumab (arm 2) until 24 months from the date of the first dose of pembrolizumab or until the end of treatment due to disappearance of injectable lesions, complete response, disease progression per irRC-RECIST or intolerance of study treatment (AE). AE, Adverse Event requiring permanent discontinuation of study treatment; CR, Complete Response; PD, Progressive Disease; Rx, treatment; T-VEC, talimogene, laherparepvec. $^a$Subjects will be followed-up for serious adverse events until 90 (+7) days after the last dose of talimogene laherparepvec or the last dose of pembrolizumab, whichever is later. $^b$Long-term follow-up will be performed every 12 weeks (±28 days) until approximately 60 months after the last subject enrolled in phase 3.

Example 9. Phase 3 Clinical Trial Combining Talimogene Laherparepvec with Pembrolizumab A phase 3 trial is being conducted in patients with previously untreated, unresectable, stage IIIB to IVM1c melanoma to evaluate the efficacy of talimogene laherparepvec with pembrolizumab versus placebo with pembrolizumab, as assessed by Progression-Free Survival (PFS) (response evaluation by blinded independent central review using modified Response Evaluation Criteria in Solid Tumors 1.1 (RECIST)) and overall survival (OS) (FIG. 12). Subjects are randomized 1:1 to receive the following: (1) Arm 1: talimogene laherparepvec plus pembrolizumab; and (2) Arm 2: placebo plus pembrolizumab.

The secondary objectives of the phase 3 trial include (1) evaluation of the efficacy of talimogene laherparepvec with pembrolizumab versus placebo with pembrolizumab as assessed by complete response rates, OS in subjects excluding Stage IVM1c, overall response rates, best overall response, durable response rate, and disease control rate; (2) evaluation of the safety of talimogene laherparepvec with pembrolizumab versus placebo with pembrolizumab; and (3) evaluation of Patient Reported Outcomes (PRO) in phase 3 as assessed by the European Organization for Research and Treatment of Cancer (EORTC) Quality of Life Questionnaire Core 30 (QLQ-C30) Global Health Status/Quality of Life (GHS/QoL) subscale.

Randomization is stratified by stage of disease: less advanced stages (IIIB, IIIC, and IVM1a) versus more advanced stages (IVM1b and IVM1c) and by prior BRAF inhibitor therapy: no prior BRAF inhibitor versus BRAF inhibitor with or without MEK inhibitor.

Key inclusio, criteria include: Male or female age ≥18 years with histologically confirmed diagnosis of melanoma and stage IIIB to IVM1c for whom surgery is not recommended. Subjects should have measurable disease and be a candidate for intralesional therapy administration into cutaneous, subcutaneous, or nodal lesions. Subjects should have Eastern Cooperative Oncology Group (ECOG) performance status of 0 or 1, and adequate hematologic, hepatic, renal, and coagulation function. Subjects should be treatment-naïve (should not have received any prior systemic anticancer treatment consisting of chemotherapy, immunotherapy or targeted therapy) given in a non-adjuvant setting. Subjects with BRAF mutation tumors may receive treatment with BRAF inhibitors either alone or in combination with MEK inhibitor as their only prior systemic therapy.

Key exclusion criteria include: No active cerebral metastases and or carcinomatous meningitis, subjects should not have uveal or mucosal melanoma. Subjects should have no history of immunodeficiency states. Subjects should not have received prior treatment with talimogene laherparepvec, any other oncolytic viruses, pembrolizumab, or any other inhibitor of PD-1, PD-L1 or programmed cell death ligand 2 (PD-L2). Subjects should not have a history of evidence of symptomatic autoimmune diseases. Subjects should not have active herpetic skin lesions or prior complications of herpetic infection and should not require intermittent or chronic treatment with an anti-herpetic drug.

Tahmogene Laherparepvec/Placebo Treatment

The first cycle of talimogene laherparepvec or placebo is 21 (+3) days. Subsequent cycles should be given every 2 weeks (±3) days until week 9 and every 3 weeks (±3) days thereafter. On day 1 of cycle 1, the first dose of talimogene laherparepvec is up to 4.0 mL of $10^6$ PFU/mL or placebo. The second injection of up to 4.0 mL of $10^8$ PFU/mL should be administered 21 (+3) days after the initial injection (i.e., no sooner than day 22 but should not be delayed more than 3 days after the 21-day time point). Talimogene laherparepvec/placebo should be administered until disappearance of injectable lesions, complete response, documented confirmed progressive disease by iRC-RECIST, intolerance of study treatment, 24 months from the date of the first talimogene laherparepvec/placebo, or end of study, whichever occurs first. The treatment cycle interval may be increased due to toxicity. When talimogene laherparepvec or placebo injections and pembrolizumab are administered on the same day, talimogene laherparepvec or placebo should be administered first, if possible.

Pembrolizumab Treatment

Pembrolizumab at a dose of 200 mg is administered intravenously every 3 weeks (±3 days). The second dose of pembrolizumab is administered 21 (+3) days after the initial dose. The treatment cycle interval may be increased due to toxicity. When talimogene laherparepvec and pembrolizumab are administered on the same day, talimogene laherparepvec should be administered first, if possible. Pembrolizumab dosing is continued until confirmed Progressive Disease (PD) per irRC-RECIST, intolerance to treatment, 24 months from the date of the first dose of pembrolizumab, or the end of study, whichever occurs first. Discontinuation of treatment may be considered for subjects who have attained a confirmed Complete Response (CR) that have been treated for at least 24 weeks with pembrolizumab and had at least 2 treatments with pembrolizumab beyond the date when the initial CR was declared.

Example 10. Phase 1b Clinical Trial Combining Talimogene Laherparepvec and Pembrolizumab in Patients with Recurrent or Metastatic Squamous Cell Carcinoma of the Head and Neck A Phase 1b trial (MASTERKEY232; CiinicalTrials.gov Identifier: NCT02626000) was designed in patients with recurrent or metastatic squamous cell carcinoma of the head and neck (SCCHN) to receive combination therapy of intralesional injection of talimogene laherparepvec with systemic administration of pembrolizumab. The primary objective was to assess the safety of this combination and secondary objectives included immune-related tumor responses.

Eligible patients, 18 years or older, had histologically confirmed metastatic or recurrent SCCHN of the oral cavity, oropharynx, hypopharynx, or larynx, and the disease was considered unresectable and not amenable to curative radiotherapy, and measurable disease suitable for intralesional injection (>1 cutaneous, subcutaneous, or nodal SCCHN tumor >10 mm, in longest diameter, either alone or in aggregate). Eligible patients had disease progression or recurrence after treatment with a platinum-containing therapy. Patients were required to have adequate performance status and hematologic, renal, hepatic, and coagulation function. Patients were excluded if they had active CNS metastases and/or carcinomatous meningitis, primary nasopharyngeal carcinoma, or were at risk of a compromised airway due to swelling/inflammation post-injection of the tumor, previously received talimogene laherparepvec, pembrolizumab, or other anti-PD-1 therapy. All patients provided written informed consent. Study procedures were approved by an institutional ethics committee at each site.

Study Design

This phase 1b study was an open label, multicenter, single arm study that primarily evaluated the safety of intralesional talimogene laherparepvec in combination with intravenous pembrolizumab. Thirty-six patients received talimogene laherparepvec and pembrolizumab, of which the first 16 patients were part of the DLT analysis.

The first dose of intralesional talimogene laherparepvec, up to 8.0 mL of $10^6$ PFU/mL, was administered on day 1, week 1. Following doses, up to 8.0 mL of $10^8$ PFU/mL, were given every 3 weeks. Up to 4 mL (total volume) of talimogene laherparepvec could be administered by intralesional injection at each treatment visit. The volume delivered to each injected lesion was contingent on the diameter of the lesion. The injected volume per lesion ranged from 0.1 mL for lesions ≤0.5 cm to 4.0 mL for lesions >5 cm in longest diameter. Talimogene laherparepvec administration continued until disappearance of injectable lesions, complete response (CR), confirmed disease progression (PD) per immune-related response evaluation criteria in solid tumors (iRECIST), treatment intolerance, 24 months from the first dose of pembrolizumab, or end of study, whichever occurred first. Pembrolizumab (200 mg) was administered intravenously ever 3 weeks beginning on day 1, week 1 (following the initial dose of talimogene laherparepvec on the same day). Pembrolizumab treatment was to be continued until iCR was achieved, confirmed iPD, intolerance to treatment, 24 months from the date of the first dose of pembrolizumab, or end of the study, whichever occurred first. The primary endpoint was the patient incidence of dose limiting toxicities (DLTs) starting from when both agents were given in combination. Incidence of DLTs in the first 16 evaluable patients and additional safety data was reviewed by a dose level review team (DLRT). The DLT evaluation period was 6 weeks from the initial dosing of both study treatments. To be considered in the DLT evaluation, patients needed to receive 2 doses of talimogene laherparepvec and 2 doses of pembrolizumab in combination or had a DLT after at least 1 dose of talimogene laherparepvec and pembrolizumab in combination. The secondary endpoints included the following immune-related tumor responses per the investigator using irRECIST; objective response rate (TORR; complete response+partial response), complete response rate (iCRR), best overall response (iBOR), duration of response (iDOR), disease control rate (iDCR), and progression free survival (iPES).

The primary analysis for the phase 1b clinical trial was the tumor response assessment which was completed when the last subject enrolled had the opportunity to complete the 9-week response assessment, Baseline Demographics and Characteristics In the phase 1b clinical trial, 36 patients with recurrent or metastatic squamous cell carcinoma of the head and neck were administered intratumoral talimogene laherparepvec and intravenous pembrolizumab. The baseline demographics and clinical characteristics are listed in Table 5.

TABLE 5

Baseline Demographics and Clinical Characteristics.

| | Talimogene Laherparepvec + Pembrolizumab (N = 36) |
|---|---|
| Sex - n(%) | |
| Male | 29 (80.6) |
| Female | 7 (19.4) |
| Median (range) age, y | 62 (35-77) |
| ECOG performance status, n(%) | |
| 0 | 9 (25) |
| 1 | 27 (75) |
| Baseline HSV Status, n (%) | |
| Negative | 5 (13.9) |
| Positive | 22 (61.1) |
| Unknown | 9 (25.0) |
| Primary tumor site, n(%) | |
| Oropharynx | 9 (25.0) |
| Larynx | 4 (11.1) |

TABLE 5-continued

Baseline Demographics and Clinical Characteristics.

| | Talimogene Laherparepvec + Pembrolizumab (N = 36) |
|---|---|
| Oral Cavity | 20 (55.6) |
| Hypopharynx | 3 (8.3) |
| PD-L1 status - n (%) | |
| Positive | 28 (77.8) |
| Not positive | 3 (8.3) |
| Indeterminate | 3 (8.3) |
| Missing | 2 (5.6) |

Dose Limiting Toxicity. Safety and Tolerability Combining Talimogene Laherparepvec with Pembrolizumab Sixteen patients were included in the dose limiting toxicity phase of the 1b trial. Of these 16 patients, one (6.3%) DLT was observed, a grade 5 (fatal) arterial hemorrhage. This DLT rate of 6.3% supported the enrollment of an additional 20 patients in the phase 1b part of the trial.

Thirty-six patients in the phase 1b trial received at least one dose of intratumoral tahmogene laherparepvec and at least one dose of intravenous pembrolizumab in combination. There were no unexpected safety findings and the adverse events were consistent with those observed with the single talimogene laherparepvec and pembrolizumab mon-therapies. Grade 3 or higher treatment emergent adverse events were reported in 5 (13.9%) patients considered related to talimogene laherparepvec and 3 (8.3%) of patients related to pembrolizumab. Of these grade 3 or lighter treatment emergent adverse events, 2 (5.6%) led to discontinuation of talimogene laherparepvec and 1 (2.8%) led to the discontinuation of pembrolizumab. Seven deaths were reported during the study including the DLT patient (arterial hemorrhage) which was considered related to talimogene laherparepvec and zero deaths were considered related to pembrolizumab. The most common treatment emergent adverse events were pyrexia (36.1%), dyspnea (33.3%), and fatigue (25.0%).

Anti-Tumor Activity with Combined Tatimogene Laherparepvec and Pembrolizumab

The primary analysis of the phase 1b trial was triggered when the last subject enrolled had the opportunity to complete the 9-week response assessment. The primary efficacy endpoints were objective response rate (iORR), complete response rate (iCRR), best overall response (iBOR), duration of response (iDOR), and disease control rate (iDCR) (response evaluation by investigator using immune-related response evaluation criteria in solid tumors [irRECIST]). Per irRECIST, observations of iCR, iPR, and iPD require a confirmatory scan no less than 28 days from the original observation of the response in order to be considered confirmed in the response analysis.

Of the 36 enrolled patients, 28 (77.8%) had confirmed PD-L1 positive tumors, 5 (13.9%) were HPV positive, and 13 (36.1%) were HPV negative, with 18 (50%) unknown (Table 6). The unconfirmed objective response rate (complete and partial responses) per iRECIST was 16.7% (95% CI, 6.4%-3:2.8%) with a confirmed iORR of 11.1% (95% CI, 3.1%-26.1%). The unconfirmed and confirmed disease control rate (complete, partial, and stable disease) per iRECIST was 38.9% (95% CI, 23.1%-56.5%). Long term follow-up was still ongoing at the time of the primary analysis.

TABLE 6

Best Overall Response.

Talimogene Laherparepvec and Pembrolizumab

| Best Overall Response (iBOR) | Unconfirmed (N = 36) n(%) | Confirmed (N = 36) n(%) |
|---|---|---|
| iORR (iCR/iPR) | 6 (16.7) | 4 (11.1) |
| 95% CI[b] | (6.4, 32.8) | (3.1, 26.1) |
| iCR | 0 (0.0) | 0 (0.0) |
| iPR | 6 (16.7) | 4 (11.1) |
| iSD | 8 (22.2) | 10 (27.8) |
| iPD | 11 (30.6) | 6 (16.7) |
| iUE | 1 (2.8) | 6 (16.7) |
| ND | 10 (27.8) | 10 (27.8) |
| iDCR (iCR/iPR/iSD) | 14 (38.9) | 14 (38.9) |
| 95% CI[b] | (23.1, 56.5) | (23.1, 56.5) |

[a]Per irRECIST, observations of iCR, iPR, and iPD require a confirmatory scan no less than 28 days from the original observation of the response in order to be considered confirmed in the response analysis.
[b]Binomial proportion with exact 95% confidence interval (CI).

---

What is claimed is:

1. A method of treating a tumor in a subject, wherein said tumor was non-responsive to previous adjuvant therapy with pembrolizumab or said subject failed to achieve a sustained response to previous adjuvant therapy with pembrolizumab, said method comprising:
   administering talimogene laherparepvec to the subject; and
   administering pembrolizumab to the subject,
   wherein the tumor is melanoma.

2. A method of treating a tumor in a subject, wherein said tumor progressed during previous adjuvant therapy with pembrolizumab, said method comprising:
   administering talimogene laherparepvec to the subject; and
   administering pembrolizumab to the subject,
   wherein the tumor is melanoma.

3. A method of rendering a tumor in a subject sensitive to pembrolizumab,
   wherein said tumor is resistant to adjuvant therapy with pembrolizumab, and
   wherein said method comprises contacting the tumor with talimogene laherparepvec and administering pembrolizumab to the subject,
   wherein the tumor is melanoma.

4. The method of claim 1, wherein the melanoma is recurrent, metastatic, advanced, or unresectable melanoma.

5. The method of claim 1, wherein:
   talimogene laherparepvec and pembrolizumab are administered to the subject after surgery, or
   talimogene laherparepvec and pembrolizumab are administered to the subject prior to, during, or after radiation therapy.

6. The method of claim 1, wherein:
   talimogene laherparepvec is administered before administration of pembrolizumab;
   talimogene laherparepvec is administered after administration of pembrolizumab; or
   talimogene laherparepvec is administered concurrently with pembrolizumab.

7. The method of claim 2, wherein the melanoma is recurrent, metastatic, advanced, or unresectable melanoma.

8. The method of claim 2, wherein;
   talimogene laherparepvec and pembrolizumab are administered to the subject after surgery, or
   talimogene laherparepvec and pembrolizumab are administered to the subject prior to, during, or after radiation therapy.

9. The method of claim 2, wherein:
   talimogene laherparepvec is administered before administration of pembrolizumab; or
   talimogene laherparepvec is administered after administration of pembrolizumab; or
   talimogene laherparepvec is administered concurrently with pembrolizumab.

10. The method of claim 3, wherein the melanoma is recurrent, metastatic, advanced, or unresectable melanoma.

11. The method of claim 3, wherein talimogene laherparepvec is administered to the subject prior to, during, or after radiation therapy.

12. The method of claim 3, wherein:
    talimogene laherparepvec is contacted with the tumor before administration of pembrolizumab; or
    talimogene laherparepvec is contacted with the tumor after administration of pembrolizumab; or
    talimogene laherparepvec is contacted with the tumor concurrent with the administration of pembrolizumab.

13. The method of claim 1, wherein pembrolizumab is administered at a dose of 200 mg once every three weeks.

14. The method of claim 1, wherein talimogene laherparepvec is administered in an initial dose of $10^6$ plaque forming units (PFU)/mL and one or more secondary doses of $10^8$ PFU/mL.

15. The method of claim 2, wherein pembrolizumab is administered at a dose of 200 mg once every three weeks.

16. The method of claim 2, wherein talimogene laherparepvec is administered in an initial dose of $10^6$ plaque forming units (PFU)/mL and one or more secondary doses of $10^8$ PFU/mL.

17. The method of claim 3, wherein pembrolizumab is administered at a dose of 200 mg once every three weeks.

18. The method of claim 3, wherein talimogene laherparepvec is administered in an initial dose of $10^6$ plaque forming units (PFU)/mL and one or more secondary doses of $10^8$ PFU/mL.

* * * * *